(12) United States Patent
Jones et al.

(10) Patent No.: US 7,461,658 B2
(45) Date of Patent: Dec. 9, 2008

(54) METHODS FOR TREATING EYE CONDITIONS

(75) Inventors: Jeffrey W. Jones, Robertson, WY (US); Marcia Angela Van Valen, Aliso Vielo, CA (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

(21) Appl. No.: 11/973,056

(22) Filed: Oct. 4, 2007

(65) Prior Publication Data

US 2008/0033407 A1  Feb. 7, 2008

Related U.S. Application Data

(62) Division of application No. 11/413,590, filed on Apr. 26, 2006.

(51) Int. Cl.
  *A61B 19/00* (2006.01)
(52) U.S. Cl. .......................... 128/898; 606/4
(58) Field of Classification Search ............... 606/4–6, 606/10–12; 128/898; 607/88, 89; 351/205–212
See application file for complete search history.

(56) References Cited

U.S. PATENT DOCUMENTS

| | | | |
|---|---|---|---|
| 6,149,643 A * | 11/2000 | Herekar et al. | 606/5 |
| 6,263,879 B1 * | 7/2001 | Lin | 128/898 |
| 6,575,962 B2 * | 6/2003 | Hohla | 606/5 |
| 6,824,540 B1 | 11/2004 | Lin | |
| 2003/0220630 A1 | 11/2003 | Lin | |
| 2005/0043722 A1 | 2/2005 | Lin | |

FOREIGN PATENT DOCUMENTS

WO  200236029 A  5/2002

OTHER PUBLICATIONS

International Search Report, Dec. 18, 2006, PCT/US06/16066.
Written Opinion, Dec. 18, 2006, PCT/US06/16066.
Supplementary European Search Report, Jul. 9, 2008, EP 06 75 1364.

* cited by examiner

*Primary Examiner*—Ahmed M Farah
(74) *Attorney, Agent, or Firm*—Stout, Uxa, Buyan & Mullins, LLP

(57) ABSTRACT

Architectures and techniques for treating conditions of the eye, such as presbyopia, utilize sources of treatment energy, such as electromagnetic energy emitting devices, to implement non-corneal manipulations. According to these devices and methods, the sources of treatment energy are activated to direct energy onto parts of the eye, such as the conjunctiva and sclera, to treat presbyopia. The treatments can affect at least one property of the eye and enhance an accommodation of the eye.

34 Claims, 21 Drawing Sheets

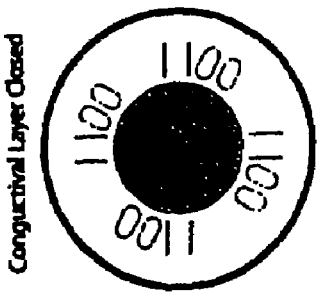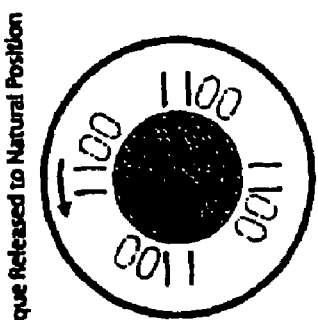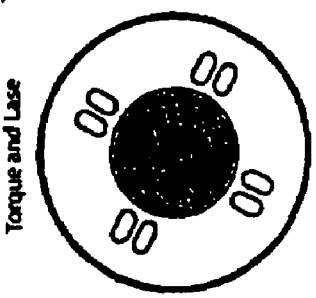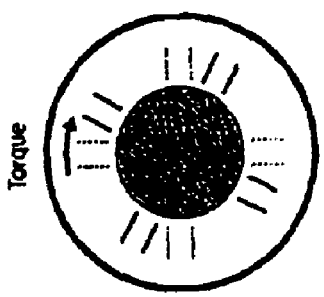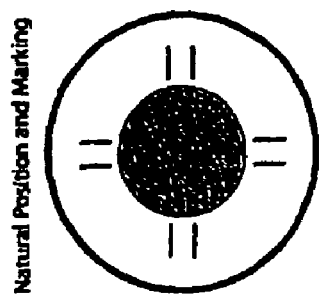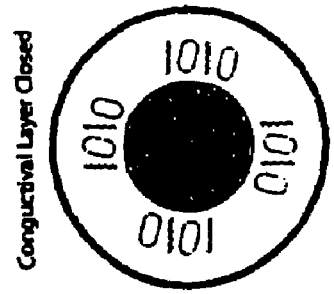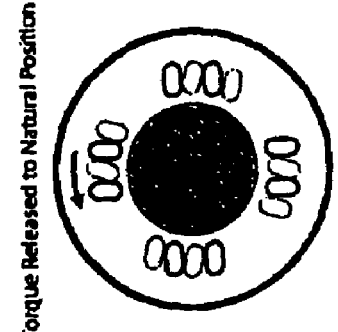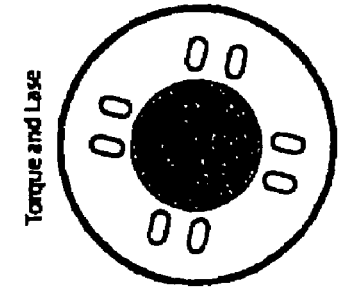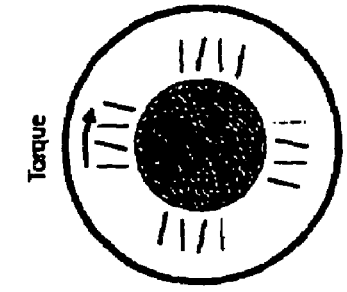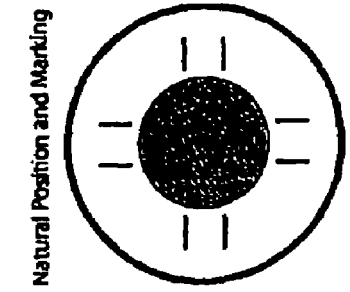

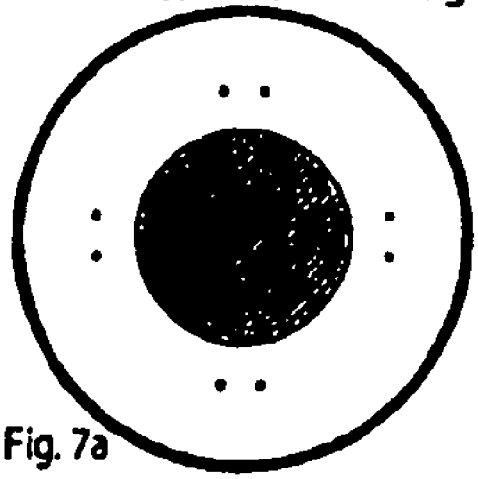
Fig. 7a — Natural Position and Marking
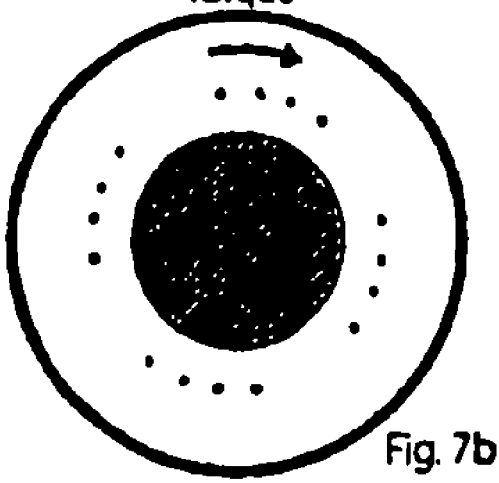
Fig. 7b — Torque
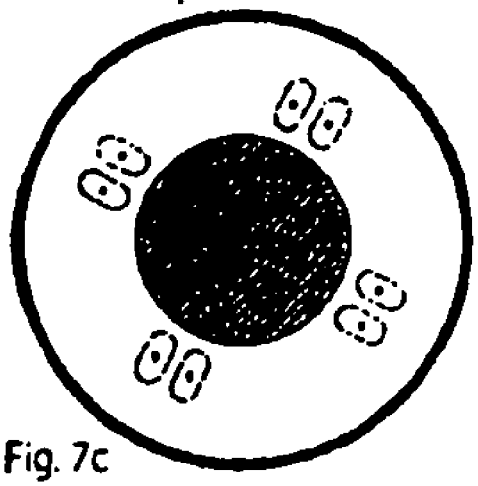
Fig. 7c — Torque and Lase
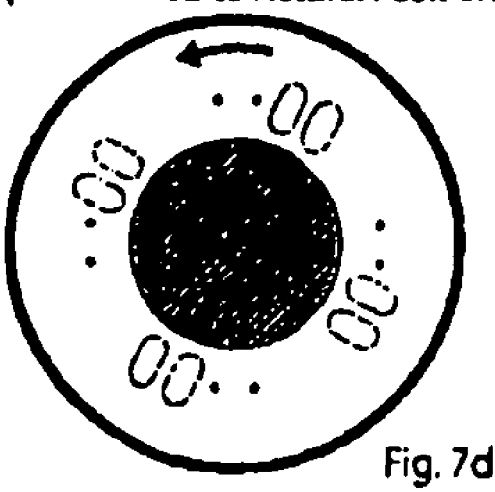
Fig. 7d — Torque Released to Natural Position

Natural Position and Marking

20-30° Torque

20-30° Torque and Lase

Torque Released to Natural Position

Natural Position and Marking

Torque

Torque and Lase

Torque Released to Natural Position

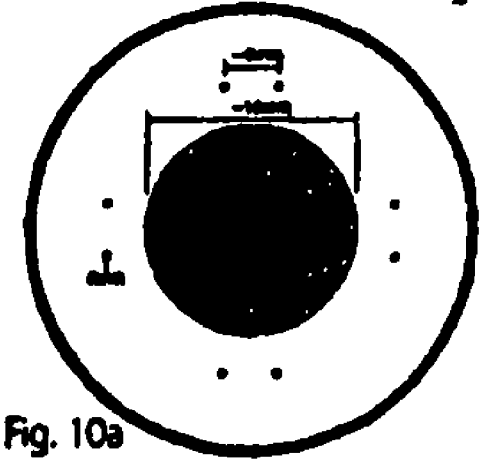
Fig. 10a — Natural Position and Marking
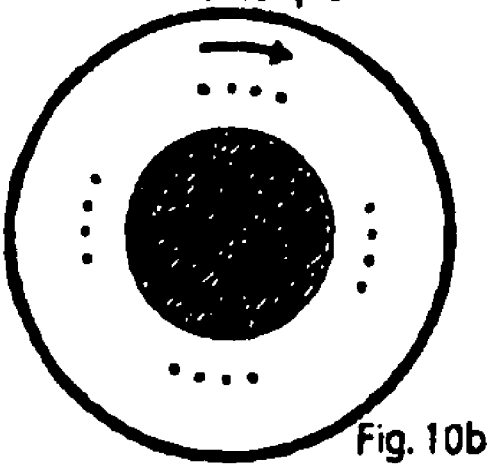
Fig. 10b — 7-12° Torque
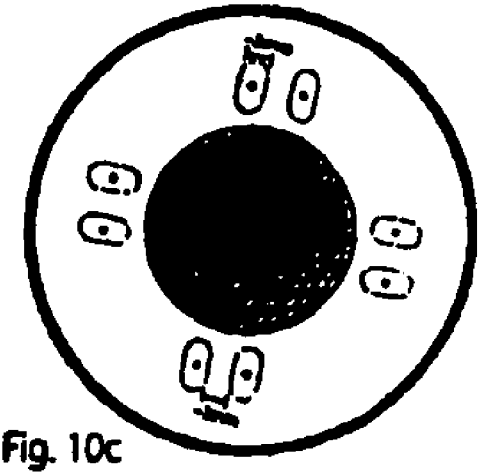
Fig. 10c — 7-12° Torque and Lase
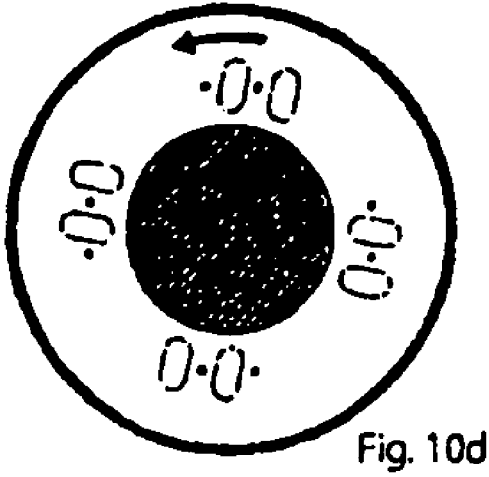
Fig. 10d — Torque Released to Natural Position

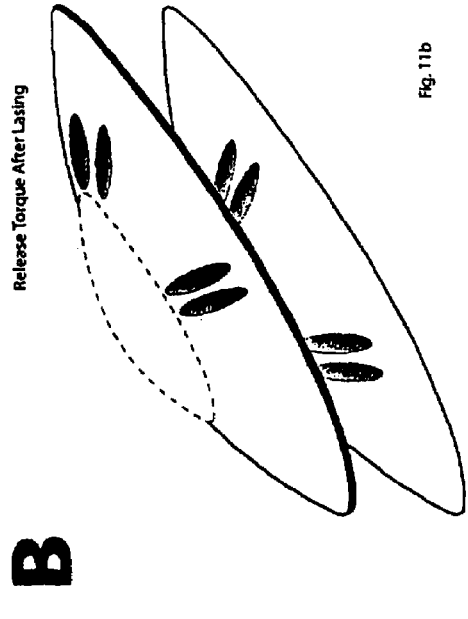
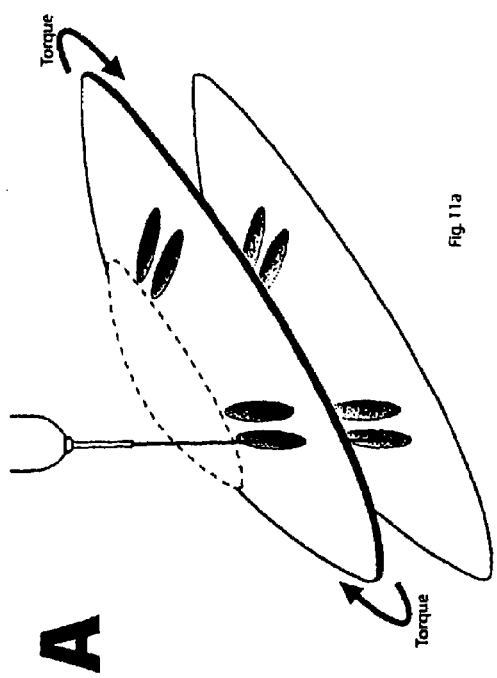
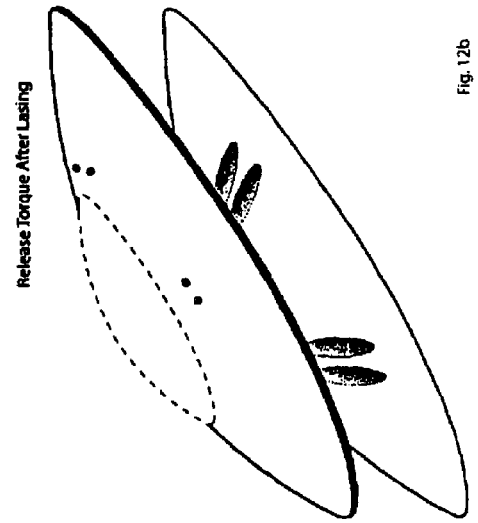
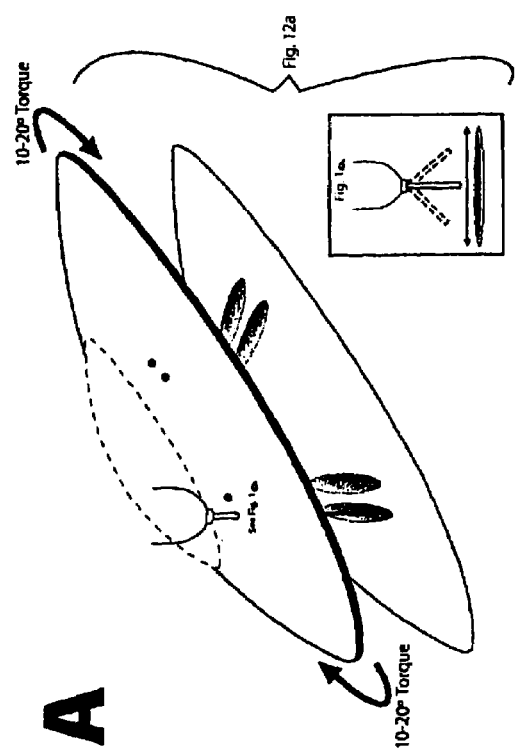

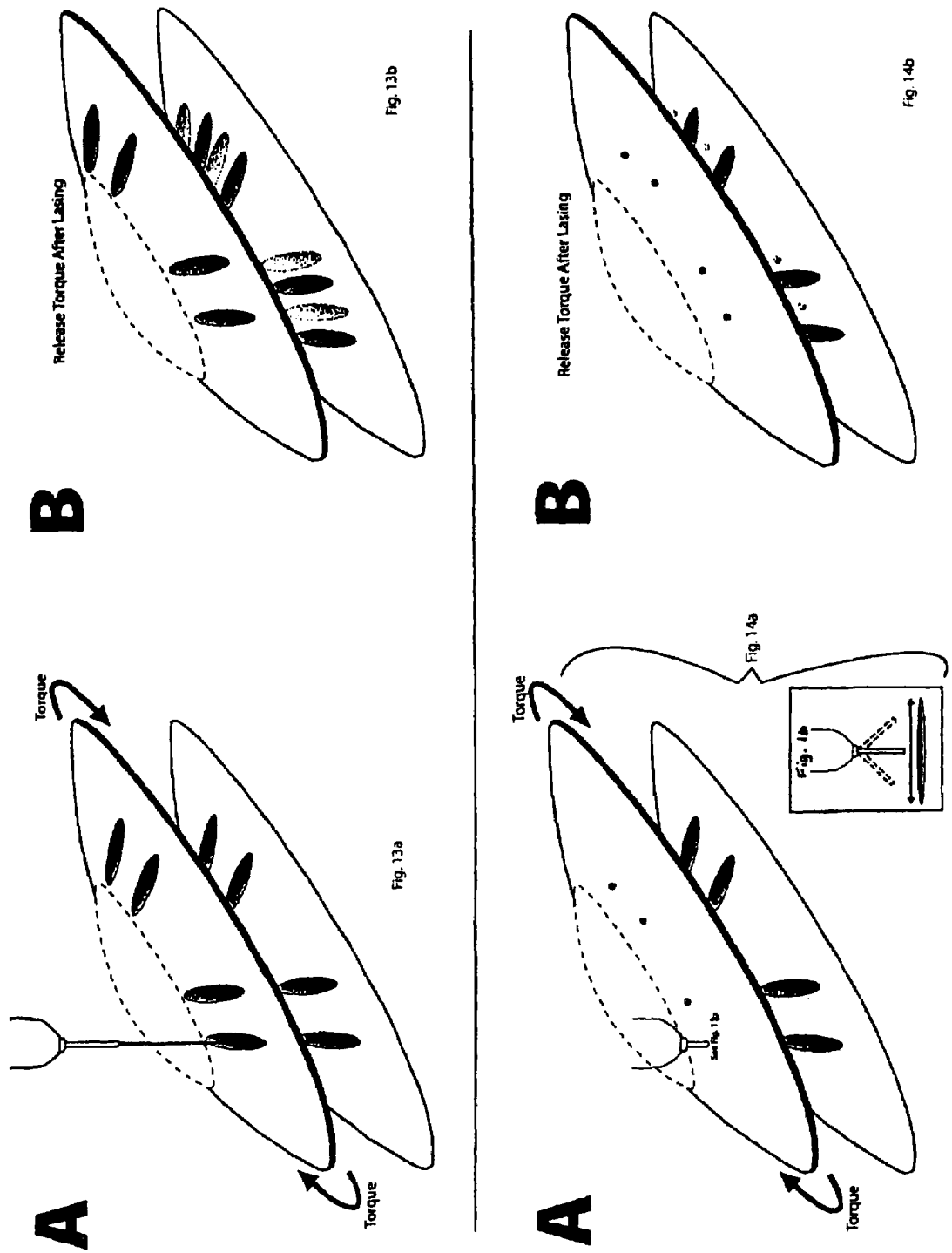

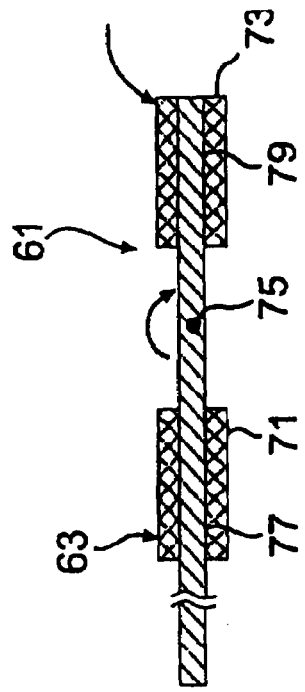
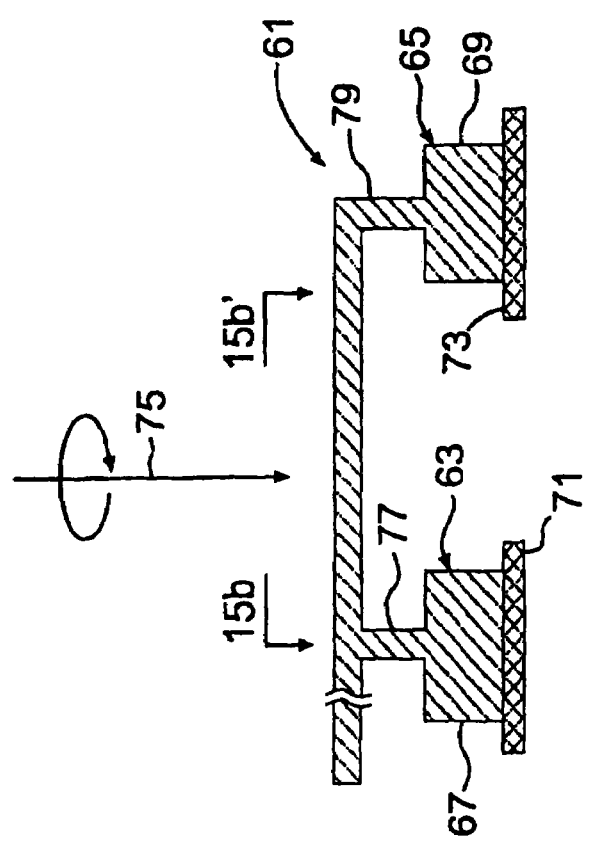
Fig. 15b
Fig. 15a

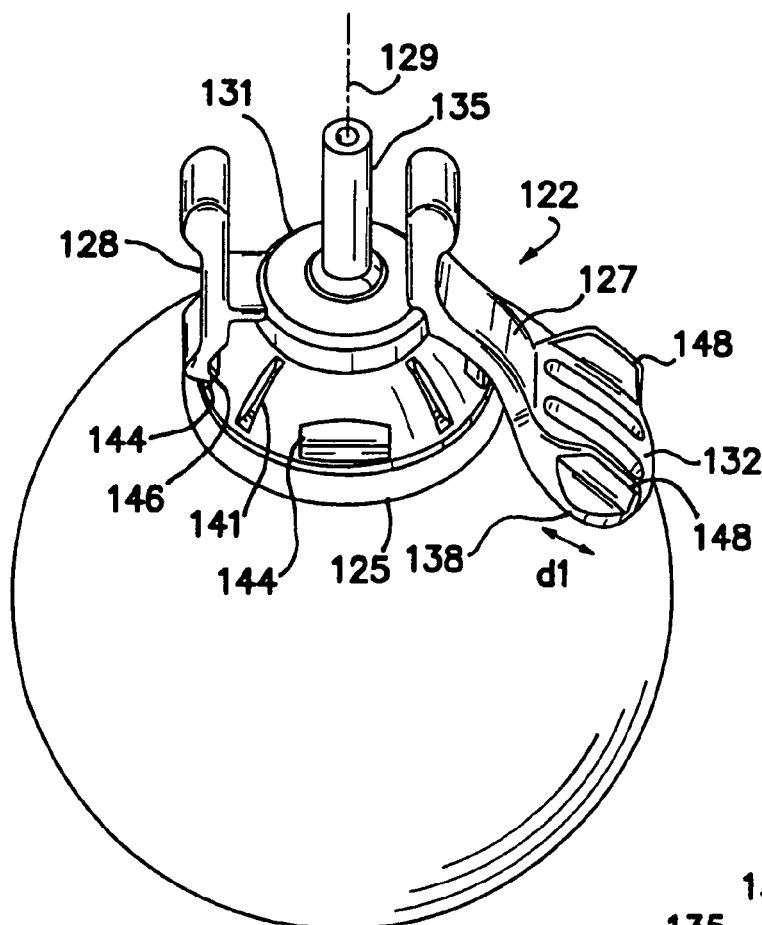
FIG. 19A
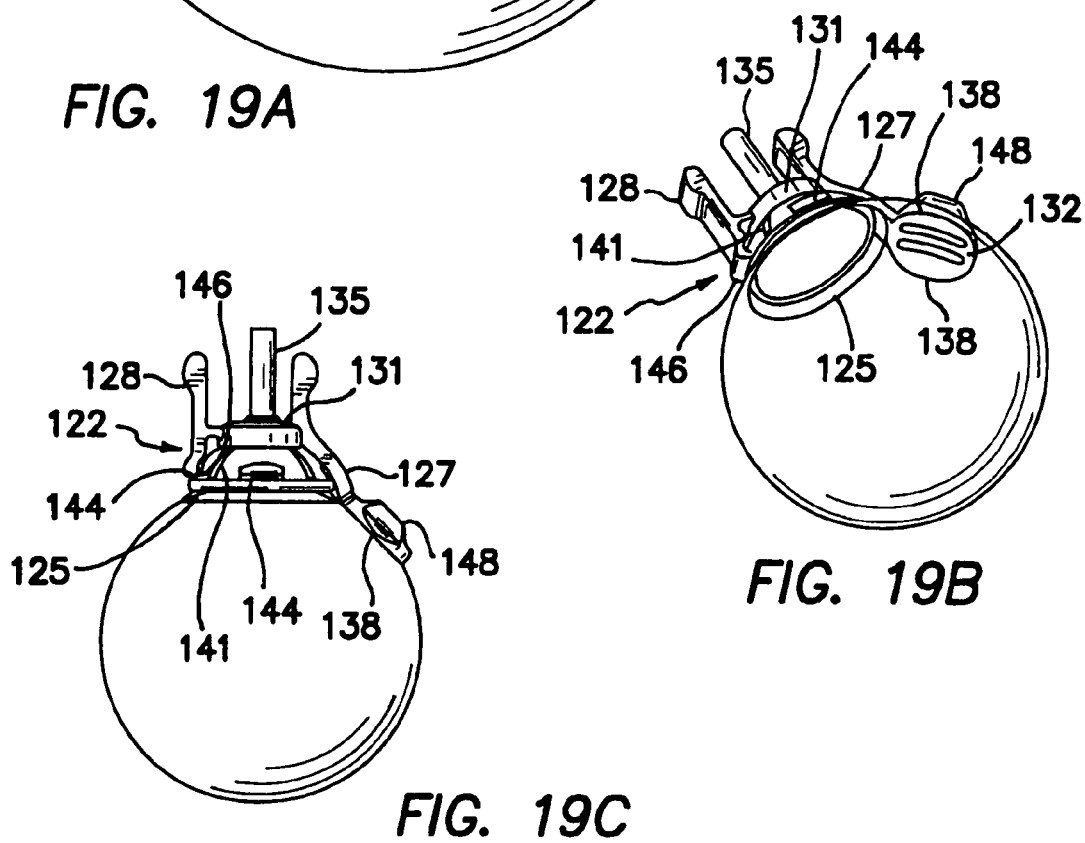
FIG. 19B
FIG. 19C

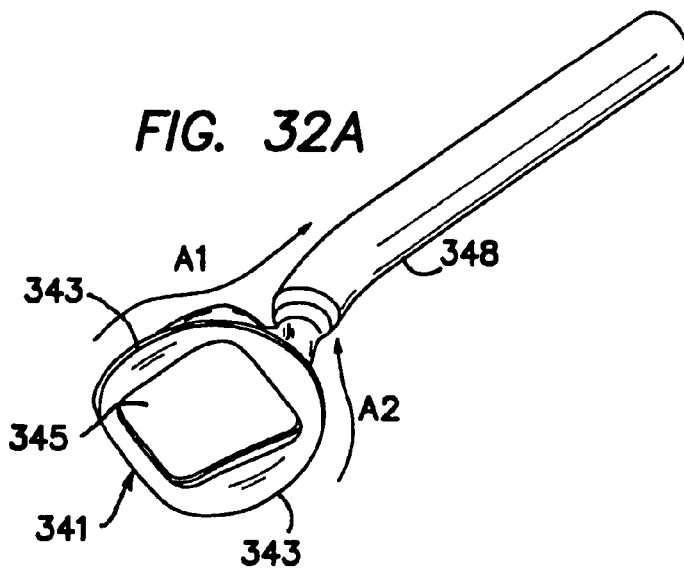
FIG. 32A
FIG. 32B
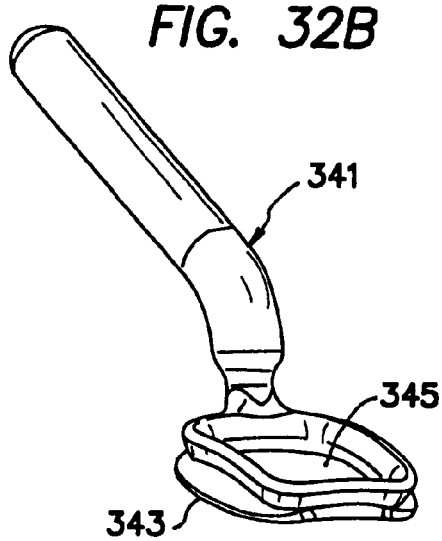
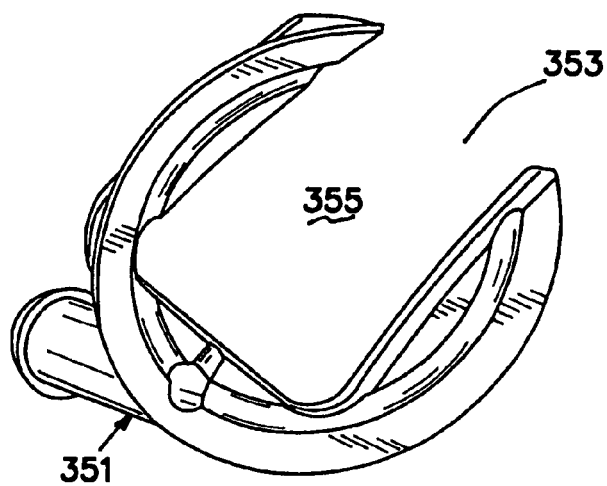
FIG. 33A
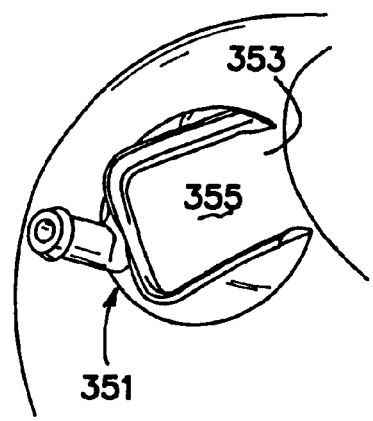
FIG. 33B

METHODS FOR TREATING EYE CONDITIONS

CROSS-REFERENCE TO RELATED APPLICATIONS

This application is a divisional of U.S. Application Ser. No. 11/413,590, filed Apr. 26, 2006 and entitled METHODS FOR TREATING EYE CONDITIONS, the entire contents of which are hereby incorporated by reference.

BACKGROUND OF THE INVENTION

1. Field of the Invention

The present invention relates generally to medical treatments and, more particularly, to methods and apparatus for treating eye disorders such as presbyopia using energies including infrared laser, ultrasound and radio-frequency.

2. Description of Related Art

Two common opthalmologic conditions relating to focusing disorders are known as myopia and hyperopia. Myopia, or nearsightedness, relates to an eyesight refractive abnormality whereby distant objects appear blurred as a result of rays of light entering the eye being brought to focus in front of the retina. Hyperopia, or farsightedness, on the other hand, relates to an eyesight refractive abnormality whereby near objects appear blurred or fuzzy as a result of light rays being brought to focus behind the retina.

One variation of hyperopia is presbyopia, which typically is associated with a person's lack of capacity to focus at near distances and which tends to develop and progress with age. Regarding this progression, presbyopia is thought to advance as the eye progressively loses its ability to accommodate or focus sharply for near vision with increasing age of the person. Accordingly, the condition of presbyopia generally signifies a universal decrease in the amplitude of accommodation of the affected person.

Myopia and hyperopia can be treated surgically using techniques including corneal interventions, such as reshaping a surface curvature of the cornea located inside of the limbus area, and non-corneal manipulations, such as altering properties of the sclera (which is located outside of the limbus area), ciliary muscle, zonules, or lens. An example of the former treatment can comprise ablating the surface of the cornea itself to form a "multifocal" arrangement (e.g., distance vision in one eye and reading vision in another eye according to a treatment plan referred to as monovision) facilitating viewing by a patient of both near and far objects, and an example of the latter treatment can comprise introducing kerfs into portions of the sclera to thereby increase accommodation. Non-corneal interventions typically comprise temporarily removing or pulling-back the patient's conjunctiva, using forceps and scissors and/or one or more of scalpels, cautery, plasma, and laser methods, followed by the actual non-corneal manipulations (e.g., forming kerfs in the sclera). After completing the kerfs, the conjunctiva is then typically sutured back into position.

SUMMARY OF THE INVENTION

Devices and methods of the present invention for treating conditions of the eye, such as presbyopia, utilize sources of treatment energy, such as electromagnetic energy emitting devices, to implement non-corneal manipulations. According to the architectures and techniques of the present invention, the sources of treatment energy can be activated to direct energy onto parts of the eye, such as the conjunctiva and sclera, to treat presbyopia, wherein the energy affects at least one property of the eye and results in an enhancement in an accommodation of the eye.

The source of treatment energy can comprise a source of electromagnetic energy, such as a laser. In certain implementations, the laser is an Erbium based, pulsed laser which emits optical energy into the sclera of the eye. Introduction of the treatment energy into the sclera can increase or facilitate an increase in accommodation of the eye, thereby mitigating the effects of presbyopia.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

BRIEF DESCRIPTION OF THE FIGURES

FIGS. 5-14 are schematic illustrations corresponding to types of procedures that can be implemented to treat an eye according to second aspects of the present invention;

FIG. 15 is a structural diagram showing a device which can be used to treat an eye according to certain aspects of the present invention;

FIGS. 19A-20 are schematic illustrations corresponding to types of structures and corresponding processes that can be implemented to treat an eye according to fourth aspects of the present invention;

FIGS. 32A and 32B are schematic illustrations corresponding to types of structures and corresponding processes that can be implemented to treat an eye according to tenth aspects of the present invention; and FIGS. 33A and 33B are schematic illustrations corresponding to types of structures and corresponding processes that can be implemented to treat an eye according to eleventh aspects of the present invention.

DETAILED DESCRIPTION OF THE INVENTION

Figure 1:
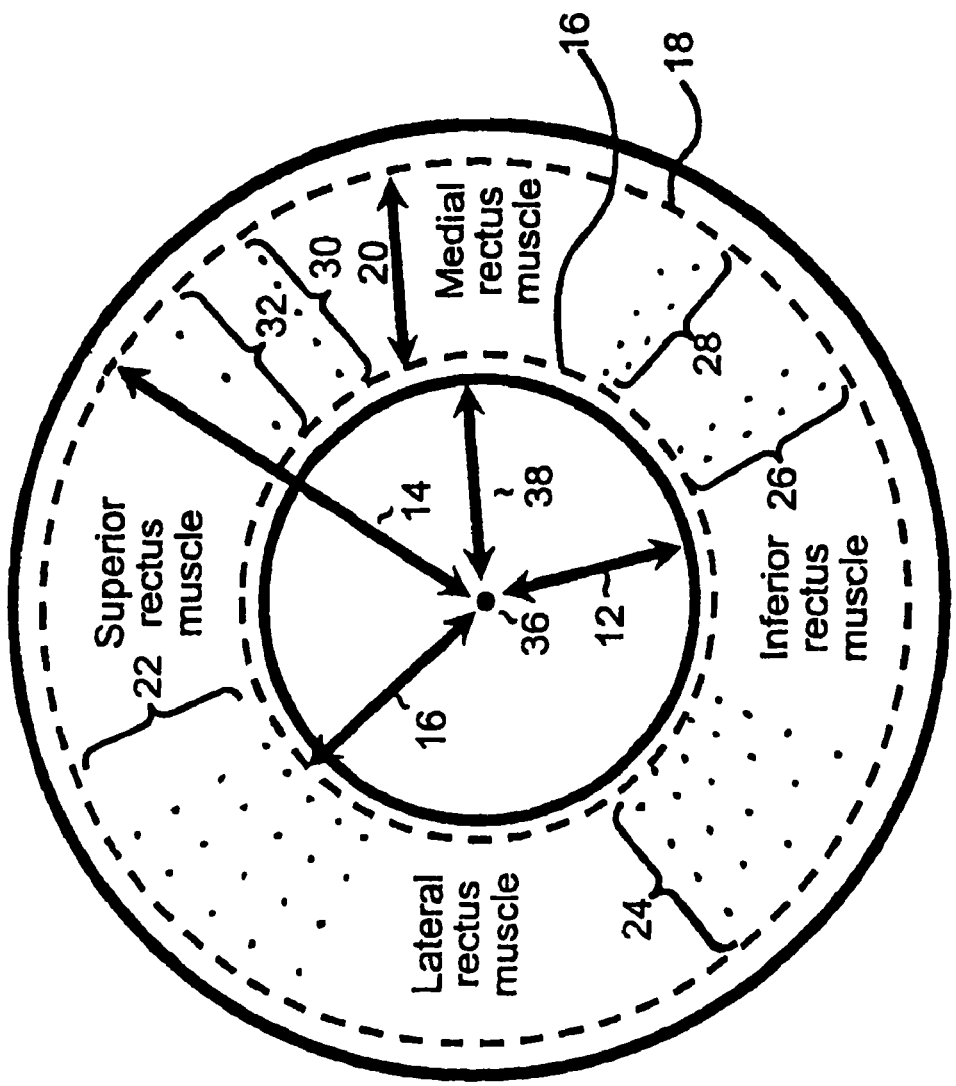
FIGS. 1-4 are schematic illustrations corresponding to types of procedures that can be implemented to treat an eye according to first aspects of the present invention.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by any appended additional disclosure (e.g., in claims format). It is to be understood and appreciated that the process steps and structures described or incorporated by reference herein do not cover a complete process flow for the implementations described herein. The present invention may be practiced in conjunction with various medical devices that are conventionally used in the art, and only so much of the commonly practiced method steps are included herein as are necessary to provide an understanding of the present invention.

Any feature or combination of features described herein are included within the scope of the present invention provided that the features included in any such combination are not mutually inconsistent as will be apparent from the context, this specification, and the knowledge of one of ordinary skill in the art.

As used herein, "accommodation" refers to the ability to change focus from distant objects to near objects, which ability tends to diminish with age.

As used herein, "choroid" refers to the highly vascular layer of the eye beneath the sclera.

As used herein, "ciliary muscle" refers to a muscular ring of tissue located beneath the sclera and attached to the lens via zonules.

As used herein, "conjunctiva" refers to the thin, transparent tissue covering the outside of the sclera.

As used herein, "cornea" refers to the clear central front tissue of the eye which can be considered to be a key component of the focusing system.

As used herein, "cornea epithelium" refers to the outermost skin or layer of the cornea.

As used herein, "limbus" refers to the boundary where the cornea meets the sclera.

As used herein, "retina" refers to the light-sensitive layer of tissue that lines the back of the eyeball and sends visual impulses through the optic nerve to the brain.

As used herein, "sclera" refers to the outer supporting structure, or "the white," of the eye.

As used herein, "vitreous body" refers to the clear colorless transparent jelly that fills the eyeball posterior to the lens and that is enclosed by a delicate hyaloid membrane.

As used herein, "zonules" refers to a circular assembly of radially directed collagenous fibers that are attached at their inner ends to the lens and at their outer ends to the ciliary muscle.

An inability of the eye to focus sharply on nearby objects, called "presbyopia," is associated with advancing age and typically entails a decrease in accommodation. Introduction of treatment energy (e.g., laser ablation), according to any of the implementations described herein, may increase or facilitate an increase in accommodation, thereby mitigating effects of presbyopia. In typical embodiments, introduction of treatment energy to the sclera tissue can increase the accommodation of the ciliary body to thereby allow the presbyopic patient to see both near and far.

In accordance with various aspects of the present invention, an accommodation can be augmented via introduction of a plurality of "tissue treatments," meaning apertures (e.g., in the form of spots) or pits formed (e.g., via ablation), or tissue areas otherwise contacted with treatment energy to visibly or non-visibly affect the tissue areas, in one or more of, for example, the cornea, limbus, conjunctiva, sclera, ciliary muscle, lens, and/or zonules. The tissue treatments may be formed by directing treatment energy from an external location toward the eye and/or may be formed by way of introducing an endoscopic device into an intraocular vicinity of the eye to thereby deliver treatment energy. The delivered treatment energy may facilitate formation of tissue treatments as described herein.

Regarding augmentation of accommodation via formation of tissue treatments in, for example, the lens, the lens may be treated (e.g., lased or drilled) with tissue treatments (e.g., micro-apertures), taking care to attenuate or avoid a distortion of optical characteristics of the lens in the process. In an exemplary implementation, sizes, arrangements, depths, and/or other characteristics of tissue treatments (e.g., micro-apertures) can be adjusted so as, for example, to increase an accommodation (e.g., flexibility) of the lens. Following treatment, the lens may be better able to change shape and focus. For instance, according to certain implementations, relatively small perforations ranging from about 1 micron to about 5 microns may be created with, for example, a micro-drill, laser, or needle. In other instances, alternative or additional tissue treatments (e.g., micro-apertures having spot shapes) may be either similarly formed in the lens or formed using means different from that used to form the mentioned tissue treatments, in the same or different locations, at the same or other points in time, and/or with the same or different sizes.

In modified embodiments, any of the tissue treatments may have sizes (e.g., maximum diameters) the same as or smaller than about 1 micron and/or larger than about 5 microns (e.g., ranging up to about 50 microns, or up to about 100 microns, or more, in certain implementations). It may be observed that, and/or measures may be taken to attenuate or avoid a possibility that, with very small diameters (e.g., about 1 micron to about 5 microns) walls of the perforations may tend to collapse on themselves. Laser characteristics can be adjusted according, for example, to a depth and diameter of desired cuts. For example, apertures formed with depths of a few microns may be generated with relatively high power densities and/or may have relatively small diameters.

Micro-apertures may be formed in the lens by, for example, directing relatively unfocused treatment energy through the pupil or iris with a focal point of the treatment energy being targeted on the lens, or they may be generated endoscopically. According to certain implementations, the focal point can be moved (e.g., advanced distally in a direction toward the retina) as the depth of the cut increases into the lens, in which case conically-shaped apertures may result, as just one example, which exemplary formations may be beneficial in certain cases. In modified embodiments, micro-apertures may be formed in the lens endoscopically. Endoscopic access may be achieved through, for example, the limbus. Entry also can be accomplished, for example, adjacent to or about 1 mm from the limbus.

In certain implementations, micro-apertures may be formed in the lens adjunctive to, for example, a scleral procedure, which may involve, for example, formation of tissue treatments in the sclera as described herein. The tissue treatments (e.g., micro-apertures in the lens) also may be treated, in accordance with another aspect of the present invention, to affect at least one property of the tissue of the tissue treatment. For example, calcification of the lens may be removed in a vicinity of the walls and floor of a tissue treatment. Removal of calcium deposits from the lens may, for example, augment an elasticity of the lens and accordingly enhance an accommodation of the lens.

Low-level laser or light therapy or biostimulation of one or more parts of the eye (e.g., the lens), further, may be performed to rejuvenate tissues thereof. In a case of the lens, an elasticity, for example, of the lens may be increased to thereby enhance an accommodation of the lens. In such instances, the lens can be considered a target chromoform (i.e., target tissue). Generally, a wavelength of applied light energy can be aligned with a tissue type of the lens.

A type of low-level laser or light therapy or photo dynamic therapy (PDT) may be used, as another example, on or in a vicinity of (e.g., on tissue adjacent to) the ciliary muscle to rejuvenate the muscle and thereby facilitate, for example, an accommodation of the eye. Light wavelengths of, for example, 670, 795, 819 and 980 nm may be employed in typical embodiments. A variety of light sources may be used, including low-level lasers and light-emitting diodes (LEDs). Continuous-wave (CW) energy or pulsed energy having a relatively high peak energy may be useful in such ciliary muscle treatments. The ciliary muscle may be stimulated in some cases with, for example, CW energy gated, for example, on for about 200 ms and off for about 200 ms. The stimulation may restore the ciliary muscle to a relatively more youthful stage. The above low-level applications may also be applied to scleral tissues according to modified embodiments, such as, for example, low-level laser therapy being applied to the sclera for scleral rejuvenation.

Scanning can be performed with for example a relatively small spot size. A joystick may be provided to facilitate any of the scanning implementations described herein. In other instances, a larger spot size can be used without scanning. Low-level light therapy may be beneficially applied to treatment of a larger portion (e.g., a relatively large or entire area) of the sclera. Treatment power densities may be relatively low, being similar, for example, to power densities used in treatments of, e.g., tennis elbow, temporomandibular joint (TMJ), or tendonitis, and in representative embodiments having characteristics less than the following: a power density at the surface of the tissue being treated of about 1.47 W/cm$^2$, a power density within the tissue of about 0.39 W/cm$^2$, a dose of energy of about 23.6 J/cm$^2$ (for a 60 second laser exposure), and/or an energy of about 9 J within and about 33.5 J at the surface of the tissue being treated.

In one implementation, a type of low-level laser or light therapy or photo dynamic therapy (PDT) may be used to increase an efficacy of or tighten the zonules. Zonules may be treated endoscopically, for example, to effectively shorten their lengths. Entry may be through a peripheral corneal or limbal area using an endoscopic laser. An anterior insertion or posterior site can be lased to cause a more direct effect on the ciliary body. One procedure in accordance with the present invention may comprise lasing the ciliary process (e.g., a portion of the ciliary muscle that connects to the zonules) in order to make the zonules more taut. According to one embodiment, the zonules can be stained, making them a target chromoform, thereby resulting in selective treatment of the zonules when exposed to optical energy.

According to a broad aspect of the present invention, one or more of the tissue treatments may be implemented as described herein using various forms of treatment energy, such as one or more of electromagnetic radiation (e.g., ablating optical energy, thermal optical energy, low level therapeutic optical energy, or radio frequency energy), ultrasound, and magnetism, alone or in combination with acupuncture or other therapeutic interventions. Low-level therapeutic optical energy applications are described in co-pending U.S. Provisional Application No. 60/687,256, filed Jun. 3, 2005 and entitled TISSUE TREATMENT DEVICE AND METHOD, the entire contents of which are expressly incorporated herein by reference. Embodiments may employ, as examples, laser acupuncture, light acupuncture, laser/RF acupuncture, and the like. In modified embodiments, any of the tissue treatments described herein may be formed with a cutting or piercing tool, such as a needle or scalpel, alone or in combination with any of the aforementioned tissue-treatment generating implements. Typically, acupuncture may be performed once a meridian or trigger point is identified. Magnets and/or magnetism applied in conjunction with the herein discussed techniques or ultrasound may be beneficial as well. In particular, tissue rejuvenation may employ ultrasound, RF, laser, light, and/or magnets applied individually or in combination. Ultrasound applied to the eye, e.g., by varying a frequency of the ultrasound applied to eye tissue, may serve to recondition the eye.

In certain implementations of methods of the present invention, first tissue treatments (e.g., micro-apertures placed in the lens) may be formed (e.g., lased) in one or more parts of the eye according to the disclosure herein, as an adjunct to, for example, other (e.g., differing) forms of refractive treatment or surgery. Such other forms, or form, of refractive treatment or surgery may comprise, for example, second treatments (e.g., second tissue treatments) formed in other ways and/or formed as described herein but in ways differing at least in part from, for example, one or more of the devices, methods, or timing used to form the first tissue treatments. For example, a non-laser form of refractive treatment or surgery may comprise application of radio-frequency (RF) energy to the cornea lens and/or may comprise conductive keratoplasty (CK). The CK, which may be appropriate for treatment of mild cases of presbyopia, may, for example, introduce a small amount of myopia into one eye so that the treated eye can be used for reading without corrective glasses. For instance, the temperature of the lens may be raised, and edges of the cornea may be manipulated to reshape the lens. Such methods may result in softening of the lens so that an ability to change a shape of the lens may be restored. Foldable lenses, also known as hinge lenses, may also or alternatively be inserted, as another exemplary implementation.

According to another broad aspect of the present invention, tissue treatments can be introduced into the sclera and/or ciliary muscle. In exemplary implementations, each of the tissue treatments comprises a shape, which may resembles a dot, spot, a short dash, or other object. That is, the shape may in certain embodiments not take a form of an elongated arc or a line. For instance, a maximum length dimension of a tissue treatment can range from about 0.01 mm to about 1 mm, a maximum width dimension can range from about 0.01 mm to about 1 mm, and a maximum depth dimension can range from about 0.01 mm up to about 5 mm (or, alternatively, up to about 1.0 mm). The shapes and locations may be dependent on the "mapping" of the eye wherein, for example, there are rigidly locations depicted by the scleral structure or the ciliary body structure. The eye muscles may also play a role in determining shapes and/or locations of the tissue treatments that may be required.

In certain embodiments, tissue treatments may be formed to have maximum diameters of about 1 micron to about 100 microns, and in particular implementations having maximum diameters of about 20 microns to about 50 microns. In other implementations, which may or may not consist of or comprise the application of ablating optical energy to the sclera, other definitions or meanings for the term "tissue treatments" may apply.

One or more of the tissue treatments may be implemented using various forms of treatment energy, such as one or more of electromagnetic radiation (e.g., ablating optical energy, thermal optical energy, low level therapeutic optical energy, or radio frequency energy), ultrasound, and magnetic implementations.

Regarding formation of tissue treatments using treatment energies, typical systems for providing treatment energies may comprise one or more of an electromagnetic source such as a laser (e.g., a diode laser) having a predetermined wavelength, an ultrasound device with a predetermined pulse, a cautery device with a predetermined setting that interacts with desired parts of the eye to form tissue treatments, a radiofrequency module, an ultrasonic component, and combinations thereof. Electromagnetic energy devices may comprise, for example, lasers having all wavelengths, such as lasers having wavelengths ranging, for example, from about 0.15 microns to about 3.2 microns. Exemplary laser beam spot sizes can range from about 0.001 mm up to about 1.0 mm (or, alternatively, up to about 2.0 mm), and exemplary laser energy per pulse values can range from about 0.1 mJ to about 50 mJ depending on, for example, the pulse duration and the laser beam spot size. Typical pulse laser widths may range from about 100 nanoseconds to about 1000 microseconds. The areas to be treated can be pre traced with a vascular laser or even the long pulse Er, Cr:YSGG, or long pulse Er:YAG, to minimize any bleeding.

Particular implementations of lasers for use on, for example, the sclera may comprise Er:YAG, Er:YSGG, Er, Cr:YSGG, or CTE:YAG lasers operated at exemplary wavelengths ranging from about 2.69 microns to about 2.8 microns, and about 2.94 microns; XeCl excimer lasers operated at an exemplary wavelength of about 308 nm; frequency-shifted solid state lasers operated at exemplary wavelengths of about 0.15 microns to about 3.2 microns; excimer lasers of ArF operated at an exemplary wavelength of about 93 nm; harmonic generations of Nd:YAG or Nd:YAL or Ti:sapphire lasers operated at exemplary wavelengths of about 190 nm to about 220 nm; CO lasers operated at a wavelength of, for example, about 6.0 microns and carbon dioxide lasers operated at a wavelength of, for example, about 10.6 microns; diode lasers operated at exemplary wavelengths of about 0.8 microns to about 2.1 microns; gas lasers operated at exemplary wavelengths of about 2.6 microns to about 3.2 microns; and other gas or solid state lasers including flash-lamp and diode-laser pumped lasers operated at exemplary wavelengths of about 0.5 microns to about 10.6 microns; and optical parametric oscillation (OPO) lasers operated at exemplary wavelengths of about 2.6 microns to about 3.2 microns.

An ultrasound device with irrigation and aspiration can be used, and may be accompanied, for example, by a chamber maintainer, for forming or facilitating the formation of tissue treatments. The purpose of the chamber maintainer is to assure that proper pressure is maintained in the eye so that a prolapse or a perforation does not occur during formation of the tissue treatments. Irrigation may include air in addition to fluids. Fluids may comprise one or more of sterile water, an anti-bacterial composition, an anti-viral composition, and combinations thereof. Fluids may be steroidal, or anesthesia based. Cautery devices can also be used at predetermined settings to form or aid in formation of tissue treatments.

According to exemplary implementations of applying energy (e.g., ablating optical energy) to tissues (e.g., the conjunctiva or sclera), any of the phrases "plurality of tissue treatments," "tissue treatments," "treatments," "tissue treatments" or "markings" can in certain embodiments refer to tissue treatment groupings and/or tissue treatment markings corresponding to tissue treatment groupings. Any of these phrases can, in the same exemplary implementations and embodiments or in others, refer to two or more tissue treatments arranged in a non-linear and non-arcuate grouping (e.g., pattern) on the tissue, and/or arranged in a plurality of non-linear and non-arcuate groupings (e.g., patterns) on the tissue. Tissue treatments or groupings of tissue treatments may comprise random line shapes, (straight, curved, or otherwise), or may comprise line shapes (straight, curved, or otherwise) formed in a pattern that is pre-determined based on a treatment customized to an area.

In other implementations, which may or may not consist of or comprise the application of ablating optical energy to the sclera, other definitions or meanings may apply. Typical embodiments can comprise grid-like groupings of tissue treatments, wherein for example the individual tissue treatments can be arranged in rows and columns in a staggered or non-staggered fashion. Other typical embodiments can comprise grid-like groupings, and/or other uniform or substantially uniform groupings, of tissue treatments. Still further embodiments can comprise non-uniform groupings of tissue treatments. The groupings may be formed manually and/or with the aid of automated devices such as computer controlled or aided scanners known to those skilled in the art.

Regarding formation by manual means, an output, such as, for example, a fiber optic tip in cases where the treatment is electromagnetic energy, may be used to focus electromagnetic (e.g., optical) energy onto for example the conjunctiva and/or sclera in order to form tissue treatments to depths of, for example, about 60% to about 99% of the sclera thickness (i.e., about 500 microns to 700 microns) and, in exemplary embodiments, depths between about 90% and 99% of the sclera thickness. An exemplary implementation can comprise an Er, Cr:YSGG laser with a 600 micron quartz or sapphire (contact) tip operated at 1.25 W and 2.78 microns, wherein for example incisions may expand up to 2 mm width after laser energy is imparted with exemplary lengths of incision being about 4 mm. In such exemplary implementations, distance between incisions may be marked at 2.5 mm but may measure 2 mm post-laser treatment, and depths can be varied depending on, for example, the patient's scleral rigidity and thickness. In other embodiments, a surgical scalpel (e.g., diamond blade) may be used to form tissue treatments having depths as previously discussed in connection with fiber optic tip embodiments. In further embodiments, plasma technology can be used.

Regarding formation by automated scanning, typical optical systems for providing treatment energies may comprise ablative lasers having predetermined wavelengths and being focused by, for example, a lens which is directed, for example, onto a scanner for patterning (e.g., using a mirror) onto the patient's eye. The scanner may comprise motorized mirrors and/or a refractive optical means such that laser energy is delivered (e.g., scanned) to the eye in predetermined patterns. The scanner thus can automatically direct laser energy over, for example, the conjunctiva and/or sclera of the eye to generate predetermined patterns and thereby form tissue treatments to depths of, for example, about 60% to about 99% of the sclera thickness (i.e., about 500 to 700 microns) and, in certain exemplary embodiments, depths between about 90% and 99% of the sclera thickness. Operating parameters for the laser can be 0.75 watts to 2.0 watts with a repetition rate of 0 to 100 Hz. Cautery device parameters can be technique specific, and can depend upon the use and desired application. However, depths of penetration in excess of 90% may remain constant. Furthermore, the output can vary depending upon the manufacturer of the cautery device.

One or more of various advantages may be realized through implementations of scanners in the context of many of the presently described embodiments, such advantages including precision, repeatability, predictability of results, uniformity of tissue treatment sizes and/or shapes, uniformity of spacings between and/or relative positions of tissue treatments, and speed. Moreover, scanners may be implemented to determine surface topographies and thicknesses of various layers of the eye, as known to those skilled in the art. In addition, embodiments implementing scanners may further provide a benefit of modifiability of treatments to a given patient. For instance a grouping or groupings may be formed during only a single procedure on the patient's eye (e.g., one surgical procedure during one patient visit) and, subsequently, should a need be presented, one or more follow-up procedures (e.g., implemented over multiple patient visits) may be performed on the patient's eye. These procedures may be performed in any order and/or sequence of sub groupings.

Precision and efficacy of tissue treatments may be enhanced when the depth or depths of the tissue(s) being affected (e.g., depth into sclera) is/are accurately determined and controlled. In the contexts of manual generation of tissue treatments, a surgeon may observe a color change of, for example, the sclera tissue being treated to determine when the tissue-treatment depth reaches a desired level. In the context of procedures on the sclera, the surgeon may, for example, cease the forming or cutting of a tissue treatment when a hue (which may be more pronounced in the context of optical ablating rather than scalpel cutting) begins to change at the bottom of the tissue treatment being formed. A darkening of hue (e.g., to a blue, violet, or dark brown) as tissue is affected (e.g., removed) at the bottom of the tissue treatment may indicate, for example, less remaining sclera and a greater exposure of the underlying layer (e.g., the vascularized choroid and/or ciliary muscle), at which time the surgeon may decide to slow or stop altogether formation of that tissue treatment or to stop formation altogether.

When scanners or other automated or semi-automated systems are used in connection with generation of tissue treatments, the patient's sclera thickness can be measured, for example, pre-operatively and the tissue-treatment depth controlled accordingly. In representative implementations, a scanning laser, or any other known tissue layer thickness measuring device, can be used to determine and subsequently control this depth. For example, the scanning laser may work with another optical or ultrasound device to detect the depth. Magnetic devices also may be used to the same purpose. As another alternative, a sensor may determine depth by automatically detecting, for example, a change in hue while lasing. Generally, a device such as, e.g., an optical detector, a calorimeter, an ultrasound probe, a device for generating and detecting electric and magnetic fields, and a tonometer can be used to measure depth of cut. In particular, a tonometer can check pressure, and hence flexibility, providing real-time feedback of an estimate of depth. Although the depth measurement determined with a tonometer may not be exactly the same as that measured post-healing, the two measurements may be highly correlated. Other methods of depth estimating include monitoring a bottom of a kerf or other topography while looking for bulging. Temperature changes also may provide an indication of depth, with a drastic change in temperature being an indication that an endpoint of the incision or kerf has been reached.

Figure 21:
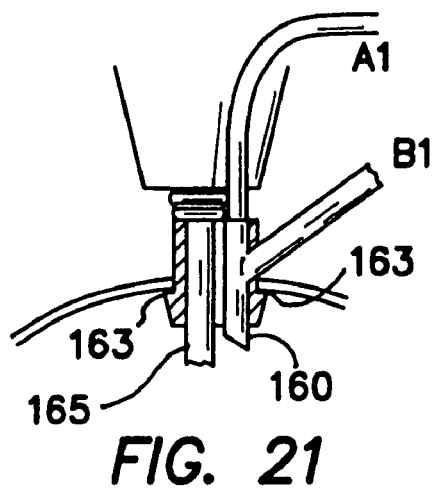
FIGS. 21-23 are schematic illustrations corresponding to types of devices and methods that can be implemented to treat an eye according to fifth aspects of the present invention.
Figure 22:
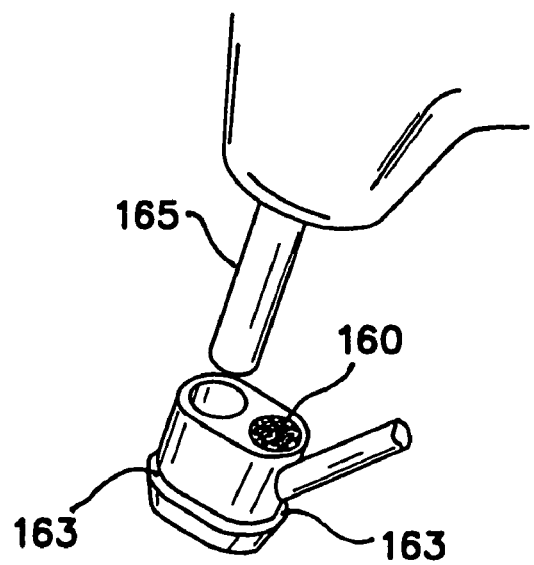
Figure 23:
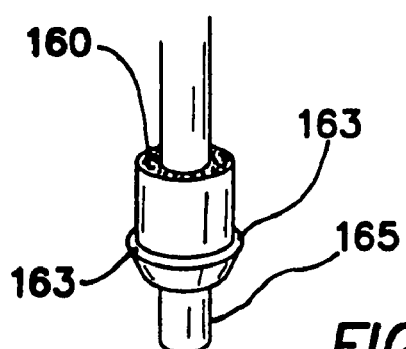

With reference to FIGS. 21, 22 and 23, according to certain examples, a camera 160, such as, for example, an intraocular fiber optic camera, may be incorporated. The camera 160 may be used, for example, to provide optical aid in conjunction with the operating site and/or to provide, for example, a determination of the incision depth in relation to the choroid. A change of color in the ocular structure, for example, can facilitate a determination of when the incisional appropriate penetration level has been reached. In other embodiments, the camera 160 (e.g., intraocular or extraocular) may be configured to facilitate viewing of tissue-treatment formations, real-time or post-procedure, or to facilitate automated or semi-automated control of, for example, a procedure for forming tissue treatments. A real-time viewing example may comprise, for example, use of an intraocular camera to facilitate real-time subconjunctival visualization during formation of tissue treatments (e.g., via laser ablation) in the sclera. While monitoring the formation of a tissue-treatment using a camera, a change in color may be automatically detected and/or visually detected by a user. A bleb or perforation may occur if the level of penetration exceeds that of the choroid structure, so it can be imperative in certain implementations that an "endpoint" method be established to avoid the possibility of hypotony or a reduction in intraocular pressure.

In exemplary embodiments, the camera 160 may be secured, for example, to an output tip of a system (e.g., a laser system), which provides treatment energy, such as shown in FIGS. 21, 22 and 23, through a fiber optic tip 165. In FIG. 21, the output tip can comprise barbs 163 for facilitating insertion of the output tip through the conjunctiva with relative ease but resisting removal of the barbed output tip from within the conjunctiva once inserted. The fiber optic camera 160 can be integrated into the handpiece such as depicted at A1 or can branch from the output tip such as shown at B1. Similar constructions can be implemented into an oval shaped output tip, as depicted in FIG. 22. Other similar constructions can comprise a fiber optic camera or fiber optic camera lens 160 surrounding the fiber optic tip 165. According to any of the embodiments described herein, the camera 160 may comprise a visualization fiber optic leading to a remotely disposed (e.g., not on the output tip) camera. The fiber optic may be disposed in a cannula, which further may contain one or more of a treatment-energy waveguide (e.g., a fiber optic tip), a visualization light source, a fluid output and an aspiration source (e.g., a calibrated aspiration source). Fluids, such as liquids (e.g., water) and/or air, can be directed over a lens of the intraocular camera and/or across a field of view of the intraocular camera to create a better viewing area and/or aspiration can be applied for removing fluids from a vicinity of the lens or field of view. In addition to or as an alternative to the discussed fluid and aspiration structures and techniques for use in combination with, for example, an intraocular camera lens, water repelling coatings (e.g., Rain-X® Original Glass Treatment, made by SOPUS Products of Houston, Tx.) can be applied to the lens for enhanced visual clarity.

According to one embodiment, washing the output tip with water operates to clean the coated, or non-coated, intraocular camera lens. In output-tip washing or other lens cleaning embodiments and/or any other water (e.g., sterile water) embodiments described herein, a gelled water or viscoelastic gel (e.g., a viscous water based gel, such as Viscasil®, available at www.viscasil.com), which can be transparent, may be used alone or in combination with water or other fluids or liquids. Any of the mentioned embodiments implementing fluid (e.g., water) for lens cleaning may incorporate any of the methods and structures described herein for adding fluid (e.g., water).

Tonometric techniques of depth measurement may comprise measuring pressure at a plurality (e.g. three or four) of locations on the sclera before a procedure is initiated. Pressure measured during the procedure then may be interpreted according to the initial pressure, with the interpretation providing an estimate of depth. A similar method may be applied to techniques for depth measurement using electric fields, magnetic fields, and chemical sensing. Mechanically, a Q-tip multi-wavelength laser device may be employed to detect depth at a bottom of a cut. For example, one wavelength (i.e., color) may indicate depth; another color may indicate vascularization related to cancer growth. Black light may be useful in identifying whites, so one approach is to continue cutting until whites can no longer be seen. In other embodiments, a UV light may be placed for ease of use in determining the area to be treated while viewing the appropriate depth. Alternatively, if a wavelength is chosen that makes blue visible, then cutting may continue until a blue hue is observed. Summarizing, different wavelengths of light may be sensitive to different characteristics of, for example, the sclera. These differing sensitivities may be exploited to determine a condition of a tissue being treated (e.g., the sclera) during a procedure, the condition being different at different layers of tissue.

Alternatively, a doctor may form a test perforation through the conjunctiva and into the sclera (i.e. extract a core sample), the test providing an indication of elasticity, rigidity, and depth of the sclera. This indication may be used to determine and refine a treatment procedure (i.e. type of ablation, number of ablations, their locations and depths). Strictures in the sclera may relate to elasticity of the sclera while colors may aid in identifying components of the sclera. A combination of the above tools including, in one example, an olfactory detector (e.g., sniffer), can be used to determine locations and appropriate times for performing a procedure. In certain embodiments, applied in addition to as an alternative to any of the above features, patterns of tissue treatments can be determined by a device, which can mark and/or apply the tissue treatments in areas based upon a rigidity theory wherein the tissue treatments are imparted into the sclera (using, e.g., a scanning laser) in the determined areas.

In addition to pre-operative measurements of depths of the layer or layers being affected, depths of remaining tissue layers at the bottoms of tissue treatments may be measured during formation of the tissue treatments (e.g., in real-time), with one or more operating parameters such as remaining tissue-treatment formation (e.g., cutting) time, pulse width, repetition rate, average power, coolant, etc., being adjusted in accordance with the results of the real-time depth measurement. For instance, a pre-operative scanning measurement may determine a sclera thickness to be about 700 microns, and ½ second into the formation of a tissue treatment a real-time depth measurement may indicate a remaining depth of the sclera at the bottom of the tissue treatment being formed to be about 325 microns. It may be determined (e.g., automatically determined) at that time to continue formation of the tissue treatment for another ½ second. This iterative process may be repeated, wherein for example a subsequent real-time measurement of remaining-depth of about 100 microns may be detected ¼ second later thus triggering, for example, a decision to continue formation for another ⅛ second.

Various combinations and implementations of depth analysis, cutting type, speed control, and feedback algorithms, among other parameters, may be implemented in various combinations, for monitoring and controlling tissue-treatment formation depths and formation characteristics, for obtaining, among other things, one or more of greater monitoring control and tissue-treatment formation accuracy. For example, the laser may have a tip of 600 microns and enter the "treatment tissue" to a predetermined depth as seen by ultrasound technology, artemis technology, confocal microscopy, tonometry, laser, or UV light. The power will be in the range of 1.25 watts and the repetition rate of 35 Hz, but will vary with other manufacturer specifications for their device.

Also, when scanners are used, initial steps comprising, for example, determining one or more reference points of the eye (e.g., a center of the pupil, one or more points on the patient's retina, triangulated unique points on the patient's iris, and/or tissue treatments or other markings formed on the patient's eye at an early stage of a procedure for the purpose of, for example, those tissue treatments being used as reference points) may be implemented so that locations of tissue treatments may be defined and/or recorded relative to the one or more reference points for use during the initial formation of the tissue treatments and/or for use during follow-up procedure(s) wherein tissue treatments may be modified and/or additional tissue treatments may be formed. In accordance with one aspect, tissue treatments formed during an initial or earlier procedure are used as reference points during remaining steps of the initial procedure and/or for the forming of additional tissue treatments during follow-up procedures. For example, rigidity mapping may be implemented wherein ultrasound is used to facilitate detection of tissue features such as a surface topography (e.g., locations of previously formed tissue treatments) for use as reference points. Also, depths of previously formed tissue treatments may be detected to provide an option of, for example, augmenting depths of one or more tissue treatments according to desired protocols. A topography unit will map the rigidity of the scleral tissue and form a grid. The grid will be placed over the eye with the "tissue treatment" sites marked and then lased or treated by a method of removing scleral tissue.

Figure 2:
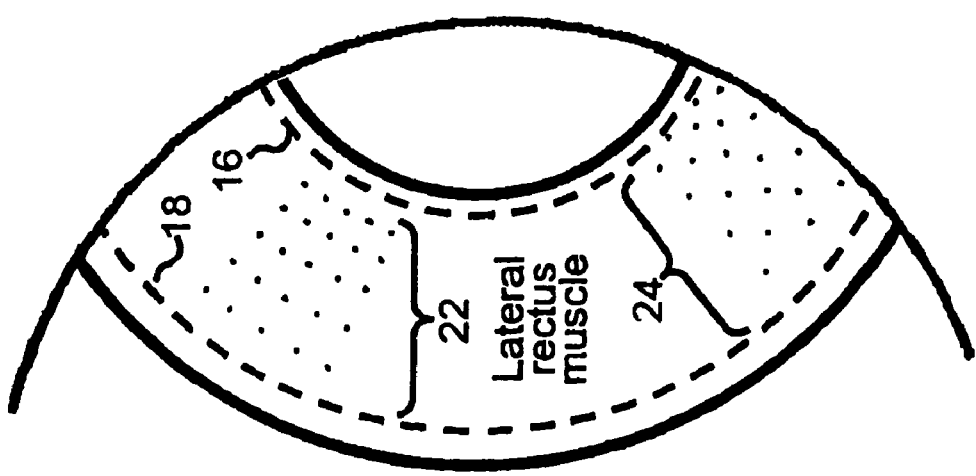

Referring more particularly to the drawings, FIG. 1 shows a schematic plan view of the right eye of a patient, and FIG. 2 is a side-elevation view of the eye depicted in FIG. 1. In accordance with an aspect of the present invention, tissue treatments (e.g., groupings of tissue treatments) may be applied to portions of, for example, surface areas of the sclera disposed between the superior rectus muscle, medial rectus muscle, inferior rectus muscle, and lateral rectus muscle. A few exemplary groupings of tissue treatments, shown as point perforations in the illustrated examples, are shown in FIGS. 1 and 2, wherein the exemplary groupings are described in accordance with a polar coordinate system. Regarding the polar coordinate system, for reference, a center point 36 of the eye is designated as the pole and a line 38 is designated as the polar axis (e.g., zero degrees).

In the illustrated embodiment of FIGS. 1 and 2, tissue treatments are applied in a form of perforations in a treatment zone that is defined between an inner radial dimension 12, denoted by phantom boundary 16, and an outer radial dimension 14, denoted by phantom boundary 18. The inner radial dimension may coincide, for example, with the limbus of the eye in typical embodiments. In representative procedures, the inner radial dimension 12 and the outer radial dimension 14 are disposed on the sclera. According to typical implementations of the present invention, a distance 20 between the inner radial dimension 12 and the outer radial dimension 14 can range from about 5 mm to about 8 mm.

A portion of interest on the sclera is located approximately 3 mm from the limbus and extends to the lens. This portion typically is 450 to 700 mm in thickness, and the perforations may be randomly delivered to this portion. The scleral tissue above four rectus muscles (superior, medial, inferior and lateral) may or may not be treated, but the scleral areas between adjacent pairs of the muscles are areas that according to certain implementations will always be treated. A first exemplary grouping 22 is depicted disposed between the superior rectus muscle and the lateral rectus muscle, and comprising 5 angularly-fixed groupings wherein each angularly-fixed grouping comprises 4 tissue treatments with each being disposed at about the same angle relative to the polar axis 38 but at a different radial distance from the center point 36 of the eye.

Tissue treatments of adjacent angularly-fixed groupings are not staggered. In the present and following examples, the particular distributions, locations and numbers of tissue treatments (e.g., 5 angularly-fixed groupings each comprising 4 tissue treatments) are selected for illustration purposes and are not intended to limit the present invention. For example, fewer numbers of tissue treatments, such as about 5 to about 30 tissue treatments per eye, or substantially greater numbers of tissue treatments, such as about 50 to about 500 tissue treatments per eye, may be implemented. The tissue treatments may be disposed in accordance with any predetermined or real-time generated groupings or patterns, and/or may be randomly grouped or relatively evenly distributed in a random or patterned fashion, using treatment energies (e.g., from a scanning laser), according to desired preferences or patient needs.

A second exemplary grouping 24 is depicted disposed between the lateral rectus muscle and the inferior rectus muscle, and comprising 5 angularly-fixed groupings wherein each angularly-fixed grouping comprises 4 tissue treatments with each being disposed at about the same angle relative to the polar axis 38 but at a different radial distance from the center point 36. In this embodiment, tissue treatments of adjacent angularly-fixed groupings are staggered, so that corresponding tissue treatments in adjacent angularly-fixed groupings are disposed at different radial distances from the center point 36.

Third and fourth exemplary groupings 26 and 28, respectively, are shown between the inferior rectus muscle and the medial rectus muscle, each comprising 2 angularly-fixed groupings with each angularly-fixed grouping comprising 4 tissue treatments disposed at about the same angle but at different radial distances from a center point 36 of the eye. In these embodiments, the tissue treatments of adjacent angularly-fixed groupings are staggered, so that tissue treatments in corresponding positions of adjacent angularly-fixed groupings are disposed at different radial distances from the center point 36.

According to certain aspects of the present invention wherein multiple procedures (e.g., implemented over multiple patient visits) are implemented to apply the tissue treatments, an initial procedure or procedures may comprise, for example, formation of one or more relatively sparsely-populated grouping(s) of tissue treatments, whereby during one or more subsequent procedures additional tissue treatments may be introduced to more densely populate (and/or to change a shape of) the one or more relatively sparsely-populated groupings of tissue treatments. For example, in one implementation the third grouping 26 may be formed during an initial procedure followed by formation of the fourth grouping 28 in a subsequent or follow-up procedure. A determination may be made before the follow-up procedure that an efficacy of the third grouping 26 is sub-optimal and/or that the patient may stand to benefit from the introduction of additional tissue treatments, after which determination the fourth grouping 28 may be formed in a follow-up procedure. Following formation of the fourth grouping 28, another evaluation may be made as to whether the patient may stand to benefit from the introduction of even further tissue treatments, and so on.

In this and other examples, the initial and follow-up groupings of tissue treatments may share parts or all of the same boundaries as distinguished from groupings having different boundaries similar to those exemplified by the third and fourth groupings 26 and 28. For instance, first parts of the third grouping 26 and fourth grouping 28 may be formed during an initial procedure followed by formation of second parts of the third grouping 26 and fourth grouping 28 in a subsequent or follow-up procedure. A determination may be made before the follow-up procedure that an efficacy of the first parts is sub-optimal and/or that the patient may stand to benefit from the introduction of second parts, after which determination the second parts of the third grouping 26 and the fourth grouping 28 may be formed in a follow-up procedure to yield, in one example, the full shapes and distributions of the third and fourth groupings 26 and 28 depicted in FIG. 1.

According to yet another example, following formation of the second parts, yet another evaluation can be conducted to determine whether the patient may benefit from the introduction of for example third parts of the third grouping 26 and fourth grouping 28, and so on.

In various embodiments, the various groupings may take on a wide variety of different configurations, including different shapes, distributions, and/or densities of tissue treatments. Moreover, in further embodiments, the parts, such as the first parts and second parts, may comprise different configurations, such as different shapes, distributions, and/or densities of tissue treatments. In one implementation, the first part may comprise a configuration similar to that shown by reference numeral 32 and the second part when added to the first part may yield a grouping such as indicated by reference numeral 30. A third part may comprise, for example, a grouping similar to that shown by reference numeral 30 or by reference numeral 32, so that the sum of the first, second and third parts may generate one or more groupings resembling one or more of, for example, the third grouping 26 and the fourth grouping 28.

The first grouping 22, second grouping 24, third grouping 26 and fourth grouping 28 may be modified, combined or duplicated, in whole or in part, in various ways, to cover portions of, as presently illustrated with reference to FIGS. 1 and 2, the sclera between the superior rectus muscle, medial rectus muscle, inferior rectus muscle, and lateral rectus muscle. For example, a procedure may comprise the placement of a first grouping 22 between each of the open areas formed between the superior rectus muscle, medial rectus muscle, inferior rectus muscle, and lateral rectus muscle. As another example, a procedure may comprise the placement of a third grouping centered in each of the 4 open areas defined between the superior rectus muscle, medial rectus muscle, inferior rectus muscle, and lateral rectus muscle.

Figure 3:
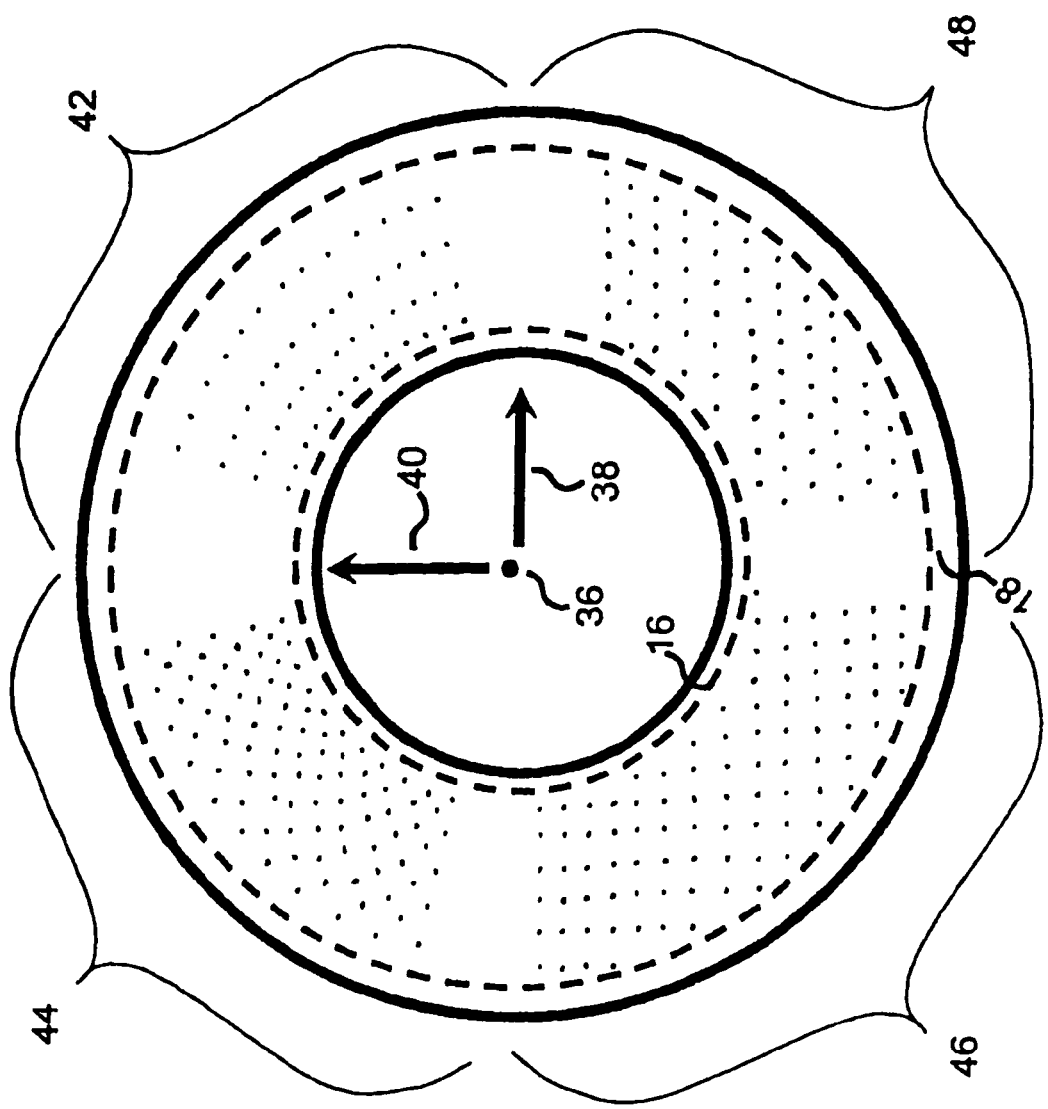

In accordance with an aspect of the present invention, tissue treatments (e.g., groupings of tissue treatments) may be applied to all or substantially all of, for example, a surface area (e.g., treatment area) of the sclera, as shown in FIG. 3. According to yet another aspect of the present invention, tissue treatments (e.g., groupings of tissue treatments) may be applied to portions of the sclera overlapping the superior rectus muscle, medial rectus muscle, inferior rectus muscle, and lateral rectus muscle, as elucidated in FIG. 4. Exemplary groupings of tissue treatments, shown as point perforations, are shown in FIGS. 3 and 4 with the exemplary groupings of FIG. 3 being described in accordance with polar coordinates (cf. center point 36 and polar axis 38) and Cartesian coordinates (cf. polar axis 38 representing an x-axis and y-axis 40) and with the exemplary groupings of FIG. 4 being described using polar coordinates (cf. center point 36 and polar axis 38).

Referring more particularly to FIG. 3, all or substantially all of a surface area of, for example, a treatment area of the sclera is provided with tissue treatments. In one representative embodiment, the treatment area is a treatment zone as described above in connection with FIGS. 1 and 2. The tissue treatments covering the treatment area may comprise a wide variety of different configurations, including different shapes, distributions, and/or densities of tissue treatments. Four exemplary distributions, any of which may be used to cover parts or all of the treatment area, in any permutation, combination or degree of duplication, are elucidated in FIG. 3. The exemplary distribution 42 corresponds in pattern to the first grouping 22 (FIGS. 1 and 2), and the exemplary distribution 44 corresponds in pattern to the second grouping 24 (FIGS. 1 and 2). The exemplary distribution 46 comprises tissue treatments disposed in rows substantially parallel to the x-axis 38 and columns substantially parallel to the y-axis 40, wherein tissue treatments of the rows and columns are not staggered. The exemplary distribution 48, on the other hand, comprises tissue treatments disposed in rows substantially parallel to the x-axis 38 and columns substantially parallel to the y-axis 40, wherein tissue treatments of the rows and columns are staggered.

Figure 4:
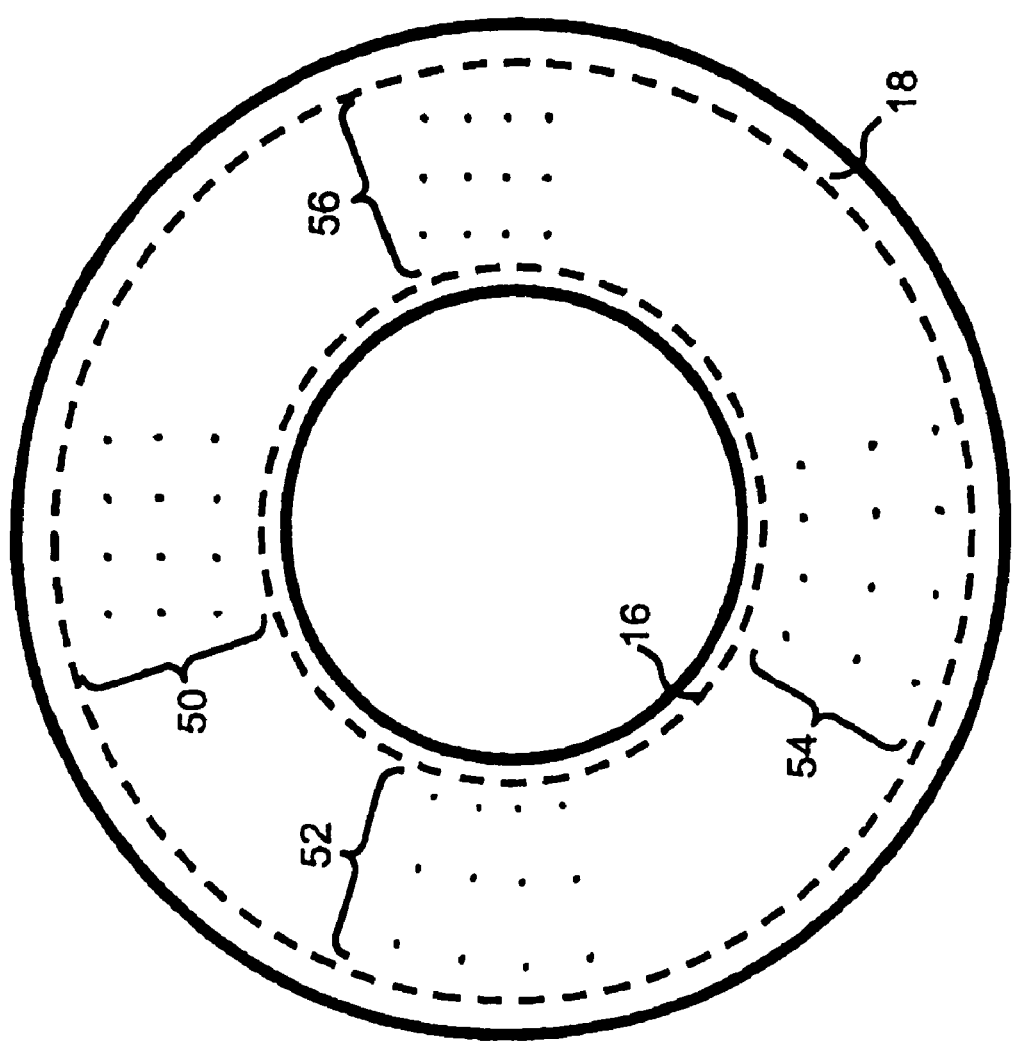

The tissue treatments 50, 52, 54 and 56 shown in FIG. 4 are applied to treatment areas of the sclera or the conjunctiva and sclera simultaneously, overlapping the superior rectus muscle, medial rectus muscle, inferior rectus muscle, and lateral rectus muscle.

The conjunctiva is the first tissue that will be perforated completely, whereas the sclera will be penetrated to a depth that allows the treatment to be ended upon detecting (e.g., viewing) the blue/brown of the choroids as previously described. Such treatments may vitalize, condition or provide other benefits to those muscles and/or to adjoining structures. For example, in embodiments wherein tissue treatments penetrate through or substantially into one or more of the superior rectus muscle, medial rectus muscle, inferior rectus muscle, and lateral rectus muscle, removed or affected areas of those muscles may be infiltrated, at least in part, with components introduced by the surgeon and/or the body.

While the tissue treatments 50, 52, 54 and 56 covering the superior rectus muscle, medial rectus muscle, inferior rectus muscle, and lateral rectus muscle may comprise, in accordance with various embodiments, a wide variety of configurations, including different shapes, distributions, and/or densities of tissue treatments, those shown in FIG. 4 correspond in pattern to the first grouping 22 (FIGS. 1 and 2).

In accordance with modified embodiments, any part or all of any of the groupings 22, 24, 26, 28, 30, 32, 42, 44, 46, 48, 50, 52, 54 or 56, may be formed to have non-linear (e.g., curved) or asymmetric properties or arrangements of tissue treatments. For instance, with respect to the first grouping 22, the exemplary 4 tissue treatments (of one or more of the exemplary 5 angularly-fixed groupings) may, instead of being disposed at about the same angle relative to the polar axis 38, be disposed at one or more different angles relative to the polar axis 38. As another example, regarding the distribution 46 of FIG. 3, one or more rows and/or columns of tissue treatments may be disposed, instead, in non-linear or asymmetric arrangements that are, for example, parallel to neither the x-axis 38 nor the y-axis 40.

In certain embodiments, the tissue treatments are applied to portions of both the conjunctiva and/or the sclera. For example, one or more of the tissue treatments can be applied, for example, wholly or partially non-invasively to an underlying layer. In a particular implementation, one or more of the tissue treatments can be applied, wholly or partially non-invasively using, for example, components that focus the treatment energy on or into the underlying sclera rather than on the conjunctiva.

According to a more specific example, ablating optical energy can be focused using optics into the sclera so that a peak concentration of the ablating optical energy occurs within the sclera and a concentration of the optical energy in the conjunctiva is substantially lower or, in one embodiment, below an ablation threshold. Dye enhancing the tissue to be treated can be used, for example, to facilitate one or more of assuring that the treatment energy (e.g., laser energy) penetrates the desired area wherein different colors of dye may be used, assuring that the treatment energy (e.g., laser energy) penetrates to the appropriate pre-determined depth wherein different consistencies and colorations can be used to this end, and allowing for better viewing of the treatment area wherein dyes can be used in conjunction with the appropriate light source for "high lighting" and the background light can be reduced for enhancement. For example, the sclera can be stained with yellow dye allowing for the location of strictures (e.g., ciliary muscles) to be highlighted a darker yellow. In general, regarding dye enhancing of the tissue to be treated according to the present invention, dyes may typically be red, green or dark in nature and can be used to enhance the depth, length or width of the incision of the tissue to be treated. Such methods typically may be combined with treatment energies such as infrared energy. The operating parameter can vary depending on the type of enhancement used, type of tissue, desired depth, length and width, and the spectrum of energy used. Thus, in the context of, for instance, the preceding example, the term "non-invasively" should be interpreted to mean that portions of the conjunctiva penetrated by the treatment energy are not substantially affected (e.g., not ablated), or are affected to a lesser extent than that to which the underlying sclera is affected, by the treatment energy.

As used herein, and not merely in the context of the present example, the term "invasively" should be interpreted to mean that portions of the tissue (e.g., sclera and or any other tissues) penetrated by the treatment energy are substantially affected (e.g., ablated) by the treatment energy. Invasive penetration of tissue by treatment energy may generate, for example, a tissue treatment.

In other examples, one or more of the tissue treatments can be applied to penetrate through the conjunctiva (e.g., to invasively penetrate wherein penetrated portions of the conjunctiva are affected, such as by being ablated) and to treat (e.g., ablate) the sclera.

According to a particular implementation, a collimated beam of ablating optical energy may be directed through both the conjunctiva and through, for example, a majority or more of the thickness of the sclera, whereby tissues of both the conjunctiva and sclera are ablated along the path of the collimated beam. The parameter ranges can, in exemplary embodiments, be dependent upon desired, predetermined or expected wavelengths, lengths, widths and/or heights of incisions, and exemplary tissue parameters/types to be affected can include conjunctival and scleral tissue. In certain implementations, the treatment energy beam can be shaped in the form of a complete tissue treatment (e.g., elongated kerf). A mapping will determine the location, pattern, shape and landscape of the region acquiring the treatment based on rigidity, muscle contraction, accommodation, and ciliary body location. The treatment energy beam can be completed by contact or non-contact of the laser energy in a pulse mode, or continuous mode that is proximal to the treatment area using a fiber based or scanner based delivery system with a predetermined software pattern or template. A beam splitter may be used to disperse energy of the beam in a pattern of the treatment area.

Dye-enhancing the tissue to be treated can, for example, be implemented. Dyes can comprise, for example, red, green or other relatively dark colors and can be used to enhance (e.g., selectively enhance by application to certain areas and/or selective coupling or matching of laser types to tissue and dye types) or otherwise affect the depth, length, width or other characteristic of the incision of the tissue to be treated. For instance, an area can be dyed for pretreatment with a laser having a wavelength that is substantially or highly absorbed by blood, wherein following (or during) the dying the coagulating laser energy can be directed over the dyed tissue treatment areas to cause coagulation or to otherwise affect a propensity of such tissue treatment areas to bleed during subsequent formation of the tissue treatments. In certain embodiments, the tissue treatment markings themselves may be formed as the dyed areas. In other embodiments, the depth, length, width or other characteristic of the incision of the tissue to be treated can be contacted with energy from a laser having a wavelength that is substantially or highly absorbed by blood, wherein following (or during) the contacting the coagulating laser energy can be directed over the tissue treatment areas to cause coagulation or to otherwise affect a propensity of such tissue treatment areas to bleed during subsequent formation of the tissue treatments.

According to typical implementations, steps may be incorporated to ensure that pretreatment coagulating energy or subsequent ablating energy does not adversely affect the retina or other tissues. Such implementations may embody one or more of relatively low energy levels, tissues-type and/or color (using, e.g., dyes) matching with relatively high-absorption wavelengths (e.g., Nd:YAG or Er, Cr:YSGG), and focusing of the energies well in front of the retina.

Any one or more of the preceding methods may be practiced or combined with, for example, application of infrared energy as the treatment-energy, wherein, again, operating parameters can vary depending on one or more of the desired type of enhancement, type of tissue, depth, length, width, other characteristic, and spectrum of energy used.

A dimension (e.g., a cross-sectional shape or area measured in a direction transverse to a direction of propagation of the treatment energy) of a tissue treatment may remain relatively constant through a depth of tissue (e.g., the conjunctiva and/or sclera) or may change with depth. For example, one or more tissue treatments may be formed to have cross-sectional shapes or areas that decrease (or, alternatively, increase) with depth into the sclera, such as would be the case, for example, with a circular tissue treatment having a diameter that decreases with increasing depth into the sclera. In typical implementations, a tissue treatment (e.g., a conically-shaped tissue treatment according to the preceding example) may comprise, for example, a diameter that tapers from about 0.1 to about 100 percent with each 1 percent drop in depth. In a particular example, the diameter may drop by about 1 percent for each 1 to 20 percent drop in depth. In the context of, for example, a tissue treatment (e.g., a conically-shaped tissue treatment) being formed in the sclera, by way of treatment energy being directed non-invasively through the conjunctiva, a tissue treatment dimension (e.g., diameter) may taper within the sclera from about 1 to about 100 percent with each 1 percent drop in depth and, in a particular example, may drop by about 1 to about 20 percent for each 1 percent drop in depth within the sclera.

Removed or affected areas corresponding to tissue treatments may for example be filled-in by a surgeon with any known biocompatible materials, such as, for example, Tisseal, anti-inflammatories or antibiotics. In accordance with one aspect of the invention, removed or affected areas corresponding to tissue treatments are at least partially filled-in by the body (e.g., via the body's natural response) with sub-conjunctiva tissue which may, for example, augment a property of the eye. For example, in the case of the sclera, the new sub-conjunctival collagen-based tissue infiltrating a removed or affected area of the sclera may have a greater elasticity or be more flexible than the original sclera tissue. The body's introduction of sub-conjunctiva tissue into removed or affected areas thus may increase the flexibility of, for example, one or more of the sclera and ciliary muscle and/or cause zonules to increase the lens accommodation. In the example of removed or affected areas in the sclera, new sub-conjunctival tissue in, for example, the sclera may facilitate or enhance a functionality or other property of the underlying ciliary body. Thus, in response to the eye's attempts to see near and far, an accommodation of the ciliary muscle may, in some instances, be increased.

According to typical implementations, the scleral tissue may be treated by directing treatment energy through the conjunctiva over the sclera with use of laser technology, whereby as previously mentioned the sclera may be treated with treatment energy (e.g., laser energy) aimed (e.g., focused) subconjunctivally, leaving the conjunctiva relatively undisrupted. For example, laser energy can be directed to focus or converge on the underlying sclera wherein, for example, the laser energy has a relatively low power density (e.g., a large spot size) on the conjunctiva while at the same time having a relatively high power density (e.g., a relatively small spot size) on the underlying sclera, and wherein the absorption rate is that of sclera tissue so that the laser energy forms a "v" in the sclera that cuts only the sclera tissue. As will be discussed below, the conjunctiva may be rotated or torqued from a different site at varying degrees in order to obtain, for example, better cosmetic effects (e.g., reduced reddening). Tissue treatments (e.g., kerfs) employed in such procedures may be formed in varying shapes as previously mentioned. Typical shapes can include, as examples, "u" and "v" shapes.

The kerfs may also be made wherein the center of the kerf has more tissue than the edges. Generally, a kerf can have a width that varies according to different rigidity factors and scleral thicknesses in different scleras. However, incisional scleral depths of tissue treatments that are greater than 90% may, in certain implementations, remain constant. According to certain embodiments, an ultrasound unit can be used to remove both conjunctival and scleral tissue. In other embodiments, cautery can be used, for example, to improve a clarity of the site where tissue treatments are to be formed and/or to generate the tissue treatments. Moreover, a light having a certain color, such as a black light, may be used to enhance a view of scleral tissue in certain embodiments.

Further, various colors may be placed in a scope (e.g., microscope) to enhance vision (e.g., surgeon discernment of features). For instance, green may allow a user to better see depth of penetration. Additionally, a tonometer may be used to detect pressure of a tissue treatment area, and/or a femtosecond laser can be used to remove or cut tissue of the tissue treatment.

One or more of the tissue treatments may be introduced with the conjunctiva in place, wherein for example the conjunctiva is left in a naturally-occurring orientation over the sclera. In such embodiments, penetration paths through/into the conjunctiva and sclera may be aligned or substantially aligned. For example, a beam of electromagnetic energy may be directed through both the undisturbed conjunctiva and through, for example, a majority or more of the thickness of the sclera. The beam may travel through the conjunctiva in a non-invasive or invasive manner as described above, whereby, in the latter case for example, tissues of both the conjunctiva and sclera may be ablated along the path of the beam of electromagnetic energy.

One or more of the tissue treatments described herein may be introduced with parts or substantially all of the conjunctiva altered (e.g., removed, reconfigured or repositioned such as by rotating the conjunctiva, or separating and/or shifting the conjunctiva, relative to the sclera) before or during introduction of the one or more of the tissue treatments, in any order or sequence of steps. Thus, with any of the implementations described herein, parts of the conjunctiva may, in certain embodiments, be manipulated while other parts are left in a naturally-occurring orientation over the sclera. In other implementations, parts of the conjunctiva above portions of the sclera receiving tissue treatments may be manipulated and/or other parts of the conjunctiva above portions of the sclera receiving tissue treatments may be left in a naturally-occurring orientation over the sclera. Furthermore, with any of the implementations described herein, substantially all of the conjunctiva may be reconfigured or repositioned (e.g., shifted or rotated about center point 36) relative to, for example, the sclera.

Moreover, in addition, or as an alternative, to the present invention's altering of the conjunctiva before or during application of tissue treatments, other aspects of the present invention may comprise introducing one or more of the tissue treatments through the conjunctiva in one or more of the pre- or post-altered states of the conjunctiva. With respect to exemplary embodiments wherein the conjunctiva is repositioned before application of treatment energy and formation of tissue treatments, once the conjunctiva is brought to (or brought back to) assume (or at least to approximate) a naturally-occurring configuration or orientation (or is otherwise brought to a post-treatment configuration or orientation), some or all of the penetration paths through/into the conjunctiva and sclera are not aligned. This lack of alignment between penetration paths of the conjunctiva and sclera, or alternatively the covering-up of penetration paths through the sclera in embodiments wherein, for example, penetration paths are not formed in part or all of the conjunctiva, can serve to provide, for example, one or more of a sealing effect for enhanced healing and structural integrity to the affected layers.

With reference again to FIG. 1, one example of repositioning the conjunctiva can include rotating the conjunctiva, relative to the sclera, before application of the tissue treatments. The conjunctiva can be gripped and rotated an amount, such as, for example about 1 to 2 degrees, or more broadly about 1 to 90 degrees, about the center point 36. In other implementations, the rotation may range from about 1 to about 45 degrees, or more, and/or different portions of the conjunctiva may be rotated, for example, at different points in time, in different directions and/or in different amounts. Following such rotation, the conjunctiva may (or may not) be held in the rotated position, for example, while some or all of the tissue treatments are applied. After application of some or all of the tissue treatments, the conjunctiva can be moved back, to a full or partial extent, to its naturally-occurring orientation and/or can be released so that the conjunctiva moves, to a full or partial extent, back to its naturally-occurring orientation.

In other implementations, after application of some or all of the tissue treatments, the conjunctiva can be rotated in the opposite direction to a greater extent than that to which it was first rotated, such as rotation in the counter-clockwise direction about 1 up to 90 degrees. Following any of the rotations or shifts of the conjunctiva described herein, and/or at any intermediate step, part or all of the conjunctiva being altered may be held using any known temporary or permanent means.

In further implementations, after application of some or all of the tissue treatments, the conjunctiva can be rotated in the opposite direction to a greater extent than that to which it was first rotated, such as rotation in the counter-clockwise direction about 1 up to 90 degrees. Following any of the rotations or shifts of the conjunctiva described herein, and/or at any intermediate step, part or all of the conjunctiva being altered may be held with any known temporary or permanent means as previously mentioned.

In other implementations, following an initial rotation of the conjunctiva, application of one or more tissue treatments (e.g., a tissue treatment in the shape of a radially-extending line or a row of tissue treatments forming the line) can be made through one or more tissue treatments (e.g., elongate kerf(s) or apertures) in the conjunctiva. The conjunctiva can then be rotated in the same direction to a greater extent than that to which it was first rotated. Then, one or more tissue treatments (e.g., a tissue treatment in the shape of a radially-extending line or a row of tissue treatments forming the line) can again be formed in the sclera through the same tissue treatments already formed in the conjunctiva so that the conjunctiva is minimally impacted. The process can be repeated to form additional tissue treatments of, for example, the same shape in the sclera, through the same tissue treatments already formed in the conjunctiva. In this example, the conjunctiva is progressively rotated in one direction with tissue treatments being formed through the same opening(s) in the conjunctiva at each step. In modified embodiments, the conjunctiva can be rotated in the opposite direction (e.g., past the original, naturally-occurring orientation) to various degrees to facilitate formation of one or more tissue treatments (e.g., a tissue treatment in the shape of a radially-extending line or a row of tissue treatments forming the line) in the sclera through the same tissue treatments already formed in the conjunctiva so that the conjunctiva is minimally impacted again. Accordingly, the conjunctiva can be rotated in both directions to facilitate formation of various tissue treatments in the sclera, all through the same opening (e.g., tissue treatment) in the conjunctiva. As a result of the reduced number of tissue treatments being formed in the conjunctiva, redness and/or healing time can be attenuated or eliminated.

FIGS. 5-14 illustrate various implementations of methods for repositioning (e.g., rotating) the conjunctiva relative to the sclera. The tissue treatments in the conjunctiva and/or sclera can comprise, for example, elongated or aperture-shaped tissue treatments such as those shown in the present examples of FIGS. 5-14, and/or may comprise groupings of tissue-treatments as discussed in any of the previously-mentioned examples, or combinations and permutations thereof, in various positions, shapes and patterns (e.g., fewer or greater numbers of elongated tissue treatments, of the same or different lengths as those shown, at for example one or more of 0, 90, 180, and 270 degrees). For instance, one or more (e.g., each) of the shown tissue-treatment elongated shapes may comprise, instead of an elongated kerf as shown, a series of smaller tissue treatments forming the same general shape (cf. grouping 30 or grouping 32 of FIG. 3). Moreover, one or more of the tissue treatments in the conjunctiva may comprise varying (e.g., reduced) sizes relative to the corresponding tissue treatments formed therebeneath in the sclera, as elucidated in the illustrated examples of FIGS. 7-10, 12 and 14.

With particular reference to FIGS. 5a-5e, this sequence depicts a rotation process wherein tissue treatments are marked, for example, at 0, 90, 180, and 270 degrees. In FIG. 5a, locations for formation of tissue treatments are marked on the conjunctiva, and in FIG. 5b the conjunctiva is moved (e.g., rotated or torqued) or shifted in some way or to some degree. The conjunctiva can, for example, be contacted (e.g., gripped) using a conjunctival template device and moved.

FIG. 5c shows that tissue treatments can then be formed in both the conjunctiva and sclera at locations corresponding to the post-movement positions of the markings, and in FIG. 5d the conjunctiva can once again be moved (e.g., rotated, torqued and/or shifted) in some way or to some degree. For example, the conjunctiva can be moved (e.g., rotated, torqued and/or shifted) in some way or to some degree so that the tissue treatments formed in the sclera are at least partially, and in certain embodiments, completely, covered by non-tissue-treatment areas of the conjunctiva. According to certain embodiments, the conjunctiva can be moved back (to the same, lesser or greater extent) in a direction from which it was first moved, but in modified embodiments it may be moved at least in part (to the same, lesser or greater extent) in other directions. As presently embodied, the conjunctiva can be rotated so that the angular locations of the markings are changed from their post-movement angular positions, and in the illustrated example of FIG. 5d the conjunctiva is rotated so that angular locations of the markings are changed back to locations corresponding to the pre-movement positions of the markings corresponding for example to the naturally-occurring orientation of the conjunctiva. The conjunctiva can be moved using for example the conjunctival template device. Following any of the movements of the conjunctiva described herein, and/or at any intermediate step, part or all of the conjunctiva being altered may be held with any herein-described or known temporary or permanent means, such as the conjunctival template device.

In certain embodiments, fluids, including water, sterile water or conditioned fluids, such as described in U.S. Pat. Nos. 5,785,521 and 6,350,123, the contents of which are incorporated herein by reference, may be added to ensure or aid in the cosmetic appeal of the treated tissue and/or to assist with healing time or other properties. For example, fluid (e.g., sterile water) may be applied by way of a small air mister (e.g., from a local or remotely-disposed canister or dropper) affixed, for example, to a device (e.g., an applinator device or output tip), between or, preferably, during application of treatment energies, to thereby attenuate or eliminate charring and/or wash away blood.

As another example, fluid (e.g., sterile water) may be applied by way of a small air mister or sprayer line affixed, for example, to a treatment energy (e.g., laser) device (e.g., handpiece) at or for any of the above-noted times or purposes. The line may comprise, for example, tubing (e.g., clip-on and/or silicone based tubing) secured to an outside or built into the device and a fluid dispensing input disposed on the device. The fluid-dispensing input may be activated, for example, to facilitate manual or powered dispensation of fluid. Manual dispensation may be implemented by way of, for example, a line leading to or integrally formed with a detachable container (e.g., pod) that can be squeezed by a user to dispense fluid (e.g., sterile water pre-packaged into a single-use, disposable pod), and powered dispensation may be implemented by way of a toggle button to initiate a powered output of fluid at, for example, a relatively low flow rate and pressure. An atomized distribution of fluid (e.g., sterile water) particles may be automatically applied to the target tissue during application of treatment energies, for example. In other examples, a drop of the fluid (e.g., sterile water) may be applied before or during application of treatment energies. In still further embodiments, treatment energies and fluid (e.g., sterile water) may be combined to facilitate electromagnetically induced mechanical cutting, as described in the preceding two patents, to enhance cutting attributes. Suction may be applied to any of the foregoing implementations, as well, for removing fluids, debris and/or liquids. For any embodiments employing suction for any purpose described herein, such as to secure a structure to a surface of the eye, specialized surfaces (e.g., relatively nonporous surfaces to facilitate suctional gripping and securement of the structure to the eye) and/or surface treatments (e.g., the above-mentioned Viscasil®) can be employed.

As shown in FIG. 5e, the tissue treatments in the conjunctiva may be closed using techniques known in the art such as sutures, surgical tacks, screws or staples, and/or applinator-style attachments including adhesives. In modified embodiments, one or more of the steps shown in FIGS. 5b and 5d, and/or the closure step of FIG. 5e, for example, may be attenuated, enhanced, or omitted, in whole or in part.

Referring to FIGS. 6a-6e, a rotation process is shown wherein tissue treatment markings are formed on the conjunctiva at the exemplary locations of zero, ninety, one hundred and eighty, and two hundred and seventy degrees. As depicted in FIG. 6a, the locations for generation of tissue treatments can be disposed on the conjunctiva in sets (e.g., pairs). One or more (e.g., all) of the sets can comprise, for example, a plurality of tissue treatments or tissue treatment groupings as described above, wherein the tissue treatments or tissue treatment groupings of one or more of the sets are configured to allow interweaving with one or more of the subsequently formed tissue treatments or tissue treatment groupings in the sclera. In the illustrated embodiment, the tissue treatments or tissue treatment groupings of the sets allow interweaving with the subsequently formed tissue treatments or tissue treatment groupings in the sclera (cf. FIG. 6d, infra). As presently shown, the tissue treatments or tissue treatment groupings of each set are spaced one from the other at different (e.g., greater) distances than for example those shown in FIG. 5a.

In FIG. 6b the conjunctiva is moved (e.g., rotated or torqued) or shifted in some way or to some degree as described above. The conjunctiva can for example be contacted (e.g., gripped) using a conjunctival template device and moved as described above. The conjunctiva can be rotated so that angular locations of the markings are changed from their pre-movement marked angular positions and, as presently illustrated, so that the post-movement angular location(s) of at least one of the markings of each set is disposed between two of the pre-movement locations of the markings of a corresponding set. According to the implementation illustrated in FIG. 6b, the post-movement angular location one of the markings of each set is disposed between two of the pre-movement marking locations of the corresponding set. In FIG. 6c the tissue treatments can be formed in both the conjunctiva and sclera at locations corresponding to the post-movement positions of the markings as described above, and in FIG. 6d the conjunctiva can be moved as described above and the tissue treatments in the conjunctiva closed as discussed above and depicted in FIG. 5e. Modified embodiments similar to those discussed above in connection with FIGS. 5a-5e may be implemented, as well.

Referring to FIGS. 7a-7d, a rotation process is shown wherein tissue treatment markings are formed on the conjunctiva at the exemplary locations of zero, ninety, one hundred and eighty, and two hundred and seventy degrees. As depicted in FIG. 7a, the locations for generation of tissue treatments can be disposed on the conjunctiva in sets (e.g., pairs). One or more (e.g., all) of the sets can comprise, for example, a plurality of tissue treatments or tissue treatment groupings as described above, wherein the tissue treatment markings (and/or tissue treatments) in the conjunctiva comprise reduced sizes relative to the corresponding tissue treatment markings (and/or tissue treatments) of, for example, FIG. 1. According to another aspect, the tissue treatment markings (and/or tissue treatments) in the conjunctiva comprise reduced sizes relative to corresponding tissue treatments that will be formed therebeneath in the sclera, as elucidated in the illustrated examples of FIGS. 7-10, 12 and 14. In the illustrated embodiment, each tissue treatment marking (and/or tissue treatment) comprises a single aperture shape disposed at each angular location (e.g., each post-movement angular location) where a corresponding tissue treatment or tissue treatment grouping will be formed in the sclera.

In FIG. 7b the conjunctiva is moved (e.g., rotated or torqued) or shifted in some way or to some degree as described above. The conjunctiva can for example be contacted (e.g., gripped) using a conjunctival template device and moved as described above. The conjunctiva can be rotated so that angular locations of the markings are changed from their pre-movement marked angular positions. In FIG. 7c the tissue treatments can be formed in both the conjunctiva and sclera at locations corresponding to the post-movement positions of the markings as described above, and in FIG. 7d the conjunctiva can be moved as described above. Subsequently, the tissue treatments in the conjunctiva can be closed as discussed above. Modified embodiments similar to those discussed above in connection with FIGS. 5a-5e may be implemented, as well.

Figure 8A:
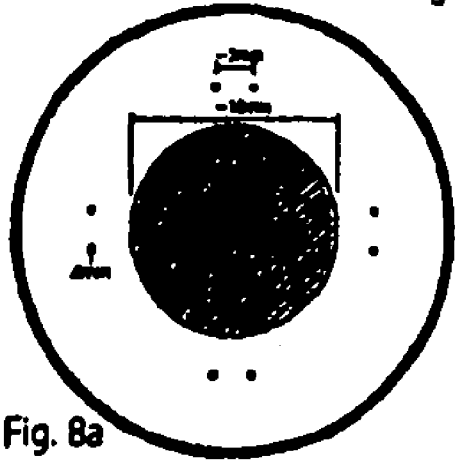
Figure 8B:
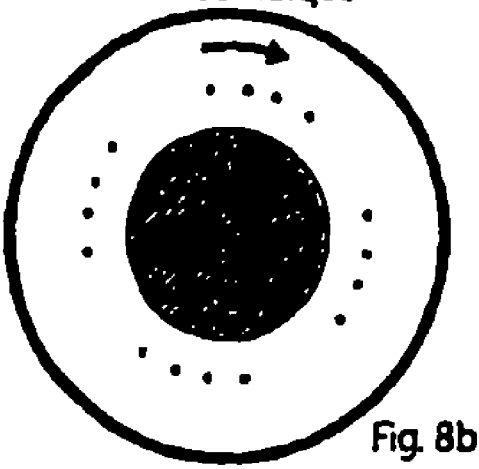
Figure 8C:
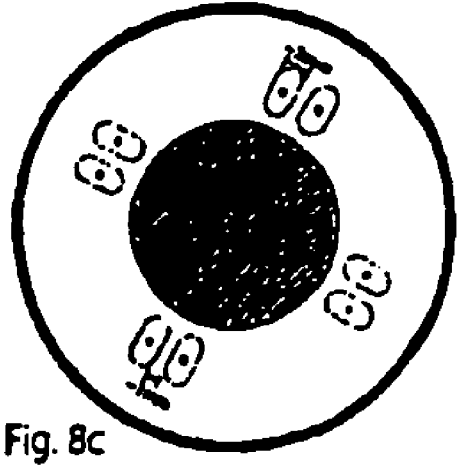
Figure 8D:
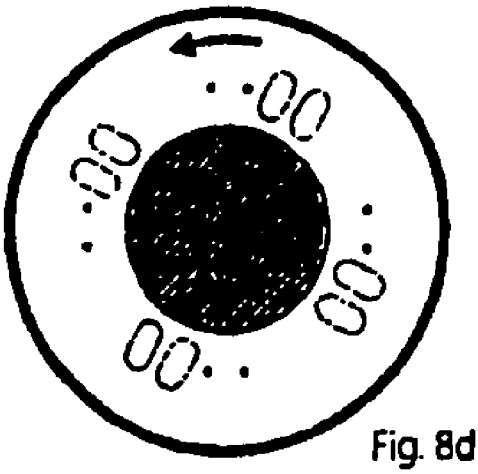

FIGS. 8a-8d depict a particular implementation of the process of FIGS. 7a-7d, wherein a pair of tissue treatment markings is formed on the conjunctiva at zero, ninety, one hundred and eighty, and two hundred and seventy degrees. In the implementation depicted in FIG. 8a, a diameter of the cornea is about 16 mm and the tissue treatment markings of each pair are spaced about 3 microns apart. In FIG. 8b the conjunctiva is rotated or torqued in the clockwise direction about twenty to thirty degrees. In FIG. 8c the tissue treatments are formed in both the conjunctiva and sclera at locations corresponding to the post-movement positions of the markings as described above, wherein the tissue treatments in the conjunctiva comprise apertures disposed at each angular location (e.g., each post-movement angular location) and corresponding tissue treatments in the underlying sclera comprise elongated shapes (e.g., elongated kerfs) extending radially outwardly at constant or substantially constant angular positions. In the illustrated embodiment, the tissue treatments of each pair in the sclera have widths of about 2 mm and are spaced about 1 mm apart. In FIG. 8d the conjunctiva is rotated or torqued in a counter-clockwise direction twenty to thirty degrees back to its naturally-occurring orientation, followed by the tissue treatments in the conjunctiva being closed as discussed above.

Figure 9A:
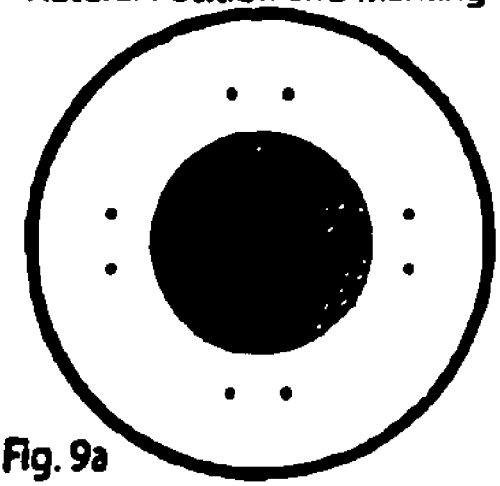

With reference to FIGS. 9a-9d, a rotation process is shown wherein tissue treatment markings are formed on the conjunctiva at exemplary locations of zero, ninety, one hundred and eighty, and two hundred and seventy degrees. As depicted in FIG. 9a, the locations for generation of tissue treatments can be disposed on the conjunctiva in sets (e.g., pairs). One or more (e.g., all) of the sets can comprise, for example, a plurality of tissue treatments or tissue treatment groupings as described above. Similarly to the embodiment of FIGS. 7a-7d, the tissue treatment markings (and/or tissue treatments) on or in the conjunctiva comprise reduced sizes relative to the corresponding tissue treatment markings (and/or tissue treatments) of, for example, FIG. 1. According to one aspect, the tissue treatment markings (and/or tissue treatments) in the conjunctiva comprise reduced sizes relative to corresponding tissue treatments that will be formed therebeneath in the sclera. As presently shown, markings for the tissue treatments or tissue treatment groupings of each set are spaced one from the other at different (e.g., greater) distances than for example those shown in FIG. 5a. In the illustrated embodiment, the tissue treatment markings comprise aperture shapes disposed at each angular location (e.g., each post-movement angular location) where a corresponding tissue treatment or tissue treatment grouping will be formed in the sclera. Furthermore, in exemplary embodiments markings for the tissue treatments or tissue treatment groupings of one or more of the sets are configured to allow interweaving of corresponding tissue treatments or tissue treatment groupings in the conjunctiva with one or more of the subsequently formed tissue treatments or tissue treatment groupings in the sclera. In the illustrated embodiment, markings for the tissue treatments or tissue treatment groupings of each set allow interweaving of tissue treatments or tissue treatment groupings in the conjunctiva with each of the subsequently formed tissue treatments or tissue treatment groupings in the sclera (cf. FIG. 9d, infra).

Figure 9B:
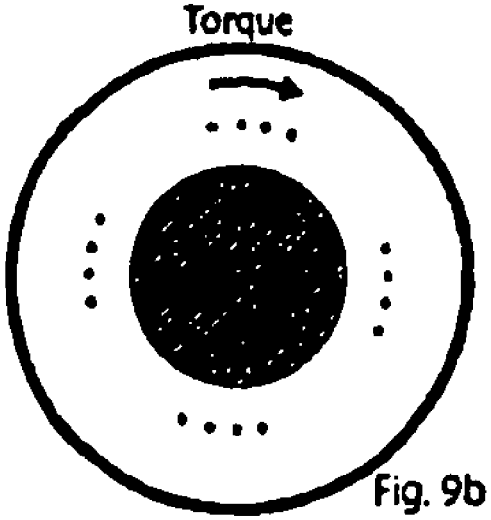
Figure 9C:
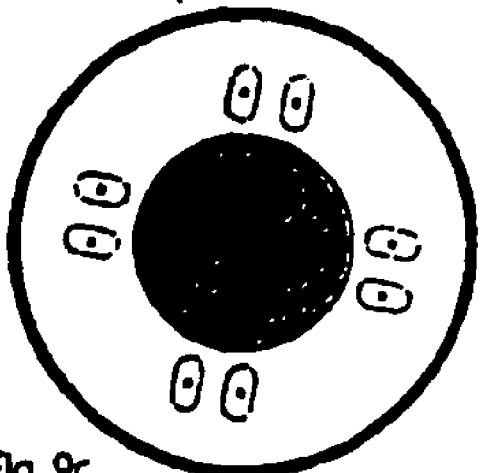
Figure 9D:
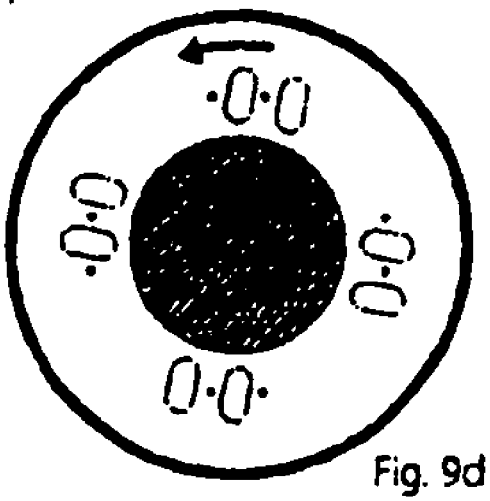

In FIG. 9b the conjunctiva is moved (e.g., rotated or torqued) or shifted in some way or to some degree as described above. The conjunctiva can for example be contacted (e.g., gripped) using a conjunctival template device and moved as described above. The conjunctiva can be rotated so that angular locations of the markings are changed from their pre-movement marked angular positions and, as presently illustrated, so that the post-movement angular location(s) of at least one of the markings of each set is disposed between two of the pre-movement locations of the markings of a corresponding set. According to the implementation illustrated in FIG. 9b, the post-movement angular location of one or more of the markings of each set is disposed between two of the pre-movement marking locations of the corresponding set. In FIG. 9c the tissue treatments can be formed in both the conjunctiva and sclera at locations corresponding to the post-movement positions of the markings as described above. The tissue treatments or tissue treatment groupings can be formed in the conjunctiva to have reduced sizes relative to the corresponding tissue treatments or tissue treatment groupings in the underlying sclera. As presently embodied, the tissue treatments or tissue treatment groupings formed in the conjunctiva comprise reduced sizes (e.g., apertures) and the tissue treatments or tissue treatment groupings in the underlying sclera comprise elongated shapes (e.g., elongated kerfs) extending radially outwardly at constant or substantially constant angular positions. In FIG. 9d the conjunctiva can be moved (e.g., moved back) as described above, after which the tissue treatments in the conjunctiva can be closed as discussed above. Modifications may be implemented similar to those discussed above in connection with FIGS. 5a-5e.

FIGS. 10a-10d depict a particular implementation of the process of FIGS. 9a-9d, wherein a pair of tissue treatment markings is formed on the conjunctiva at zero, ninety, one hundred and eighty, and two hundred and seventy degrees. In the implementation depicted in FIG. 10a, a diameter of the cornea is about 16 mm and the tissue treatment markings of each pair are spaced about 4 microns apart. In FIG. 10b the conjunctiva is rotated or torqued in the clockwise direction about seven to twelve degrees, so that following the procedure tissue treatments in the conjunctiva will be interweaved with subsequently formed tissue treatments in the sclera and the tissue treatments in the sclera will not be exposed.

In FIG. 10c the tissue treatments are formed in both the conjunctiva and sclera at locations corresponding to the post-movement positions of the markings as described above, wherein the tissue treatments in the conjunctiva comprise apertures and corresponding tissue treatments in the underlying sclera comprise elongated shapes (e.g., elongated kerfs) extending radially outwardly. In the illustrated embodiment, the tissue treatments of each pair in the sclera have widths of about 2 mm and are spaced about 2 mm apart. In FIG. 10d the conjunctiva is rotated or torqued in a counter-clockwise direction seven to twelve degrees back to its naturally-occurring orientation, followed by the tissue treatments in the conjunctiva being closed as discussed above.

FIG. 11a is a perspective view of FIG. 5c, and FIG. 11b is a perspective view of FIG. 5d. FIG. 12a is a perspective view of FIG. 7c, and FIG. 12b is a perspective view of FIG. 7d. Regarding the aperture-shaped tissue treatment markings (and/or tissue treatments) on (in) the conjunctiva, the sizes and shapes of these items can be formed, for example, to be as small as possible while still enabling, for example, formation of corresponding tissue treatments or tissue treatment groupings therebeneath in the sclera.

In the illustrated embodiment, the tissue treatment markings on and tissue treatments in the conjunctiva comprise circular shapes approximating the cross-section of (e.g., and formed by) a fiber optic tip that can, in the illustrated embodiment, be used to form the tissue treatments in the underlying sclera. Formation of tissue treatments in the conjunctiva and sclera using a laser as depicted in FIG. 12a can be accomplished using various apparatuses and techniques, exemplary approaches including one or more of: (a) separating the conjunctiva from the sclera by injecting a fluid such as an epinephrine-based fluid therebetween via a needle entry point in a vicinity of the limbus; (b) inserting a fiber optic tip through a tissue treatment located approximately midway along a length of an underlying tissue treatment (e.g., elongated kerf) or tissue treatment grouping (e.g., collection of relatively small tissue treatments approximating, or bounded by, shapes of the illustrated elongated kerfs) and then forming the tissue treatment or tissue treatment grouping in the sclera by, for example, changing an orientation of the fiber optic tip as shown in the cross-sectional view of FIG. 12a; and (c) inserting a fiber optic tip through a tissue treatment located in a vicinity anywhere between (and/or including) the limbus and a point midway along a length of an underlying tissue treatment or tissue treatment grouping.

An exemplary implementation of the (a) approach can comprise a surgeon selecting a minimum amount of anesthesia needed to keep the patient comfortable, with the anesthesia comprising at least one of the following local anesthetics: 1% Tetracaine applied in a circular ring pledget around the ciliary body for five minutes; local subtenon's injection with 2% Lidocaine applied one quadrant at a time; and topical 2% Xylocalne gel applied 20-30 minutes prior to surgery. Topical 1% Proparacaine can be applied 5 minutes before the procedure and periodically during the procedure as deemed appropriate by the surgeon according to the patient's pain response. Topical 1% Tetracaine or 2% Lidocaine can also be used. A peribulbar injection comprising a 50/50 mixture of 2% Lidocaine with 0.75% Marcaine can be administered according to the clinical judgment of the investigator if the patient does not obtain effective anesthesia by any of the above methods. One drop of a topical antibiotic (Vigamox, Ciloxan or Zymar) and one drop of a topical non-steroidal anti-inflammatory (Acular LS or Voltaren) can also be applied. The patient can be prepared according to typical protocols for refractive surgery, with a lid speculum being inserted followed by placement of a cornea protector over the cornea.

Eight inter-muscular limbal markings may then be formed 1:30, 4:30, 7:30, and 10:30 o'clock positions, followed by performance of a formix based peritomy. If needed, cautery may be used for hemostasis. Also, if needed, the surgeon may form one or more of the marks once again to map tissue treatment (e.g., incision) locations in each quadrant. Two radially orientated marks can be formed in a quadrant area 0.75 mm from the limbus (the point where the iris can no longer be seen through the cornea), with each of the two marks being extended approximately 5 mm in length posteriorly over the ciliary body and stopping anteriorly to the pars plana and with a 2.5 mm separation between each mark.

Two corresponding tissue treatments (e.g., incisions) in the marked quadrant area can then be generated, wherein scleral tissue is ablated to about 95% of a total thickness (e.g., approximately 500-550 microns) of the sclera. The incisions can be generated using an Er, Cr:YSGG laser having a frequency of 30 Hz, a wavelength of 2.78 microns, and a spot size of 600 microns. The surgeon can watch for the characteristic dark blue hue of choroid as an endpoint during each ablation process. The above-described steps can be repeated to generate additional pairs of incisions in the remaining three quadrant areas. Subsequently, each of the peritomy sites can be closed with bipolar forceps, sutures or Tisseal glue, followed by placement of 1 drop NSAID and 1 drop antibiotic thereto. An eye patch or patches may be used only if needed, and the patient can be instructed to use his or her eyes for normal near and far vision immediately following surgery.

The (b) approach, with or without inclusion of part or all of the (a) approach, is exemplified in FIGS. 12a and 12b. A typical implementation of the (c) approach, with or without any part of (a) included, can comprise forming a tissue treatment in the conjunctiva at or near the limbus and then advancing a fiber optic tip, and/or other tissue treatment forming device, distally away from the limbus to a distal (i.e., furthest from the limbus) end of the tissue treatment or tissue treatment grouping that subsequently will be formed in the sclera. The fiber optic tip is advanced beneath the conjunctiva, and in the illustrated embodiment is advanced between the conjunctiva and the sclera. Movement of the fiber tip beneath the conjunctiva can follow either or both of the following two methods, at least in part and in any combination or permutation. According to one method, as the fiber tip is advanced distally it can be activated/operated to form the tissue treatment or tissue treatment grouping that is to be formed in the sclera and/or, according to another method, the fiber tip can be advanced (e.g., advanced fully) to the distal end of the tissue treatment or tissue treatment grouping that is to be formed in the sclera and then retracted proximally while being activated/operated to form the tissue treatment or tissue treatment grouping in the sclera.

FIGS. 13a and 13b are perspective views of FIGS. 6c and 6d, respectively; and FIGS. 14a and 14b provide perspective views of FIGS. 9c and 9d, respectively. Regarding the tissue treatment markings and/or tissue treatments on and in the conjunctiva and/or sclera, these items can be formed as described previously in connection with FIG. 12b.

Other examples of repositioning the conjunctiva can include shifting, as distinguished from the above-illustrated examples depicting rotating, all or at least a part of the conjunctiva, relative to the sclera, before application of the tissue treatments. In certain implementations, some or all of the parts of the conjunctiva located above portions of the sclera receiving tissue treatments are shifted rather than, in addition to, and/or using techniques similar, analogous or substantially the same as any one or more of the above-described rotating treatments. With reference to FIG. 3, a part or all of the conjunctiva can be gripped using a conjunctival template device and shifted a slight distance in, for example, the x-axis 40 direction, such as, for example, a distance of up to 90 degrees. In other implementations, the distance may range from about 0 to about 90 degrees, and/or different portions of the conjunctiva may be shifted, for example, at different points in time, in different directions and/or different distances. Following the gripping and shifting of part or all of the conjunctiva a slight distance in the x-axis 40 direction as presently described, the conjunctiva can be held in the shifted position by using the conjunctival template device while some or all of the tissue treatments are applied. After application of some or all of the tissue treatments, the conjunctiva can be moved (e.g., shifted) back, to a full or partial extent, to its naturally-occurring orientation by using a conjunctival template device and/or can be released (e.g., by removal of a gripping or holding device or devices) so that the conjunctiva assumes, in full or in part, its naturally-occurring orientation.

In connection with any of the rotations and/or shifts of the conjunctiva described herein, and/or at any pre-operative or intermediate step, part or all of the conjunctiva being altered may be treated to, for example, control bleeding.

A method that may be used to control bleeding is described in U.S. Provisional Application No. 60/591,934, filed Jul. 27, 2004 and entitled MEDICAL LASER HAVING DUAL-TEMPERATURE FLUID OUTPUT, the entire contents of which are expressly incorporated herein by reference. According to the referenced method, cooled matter (e.g., fluid) may be applied to reduce bleeding by way of an encouragement of constriction of blood vessels. The cooled matter (e.g., air and/or water below room temperature) may be applied to a tissue, for example, to control bleeding, which bleeding may have been caused by cutting, ablating, or other trauma inflicted on the tissue. Such cooled matter (e.g., fluid, gel, ice pack) may be applied, for example, to an eye to slow or stop bleeding following an ablation procedure, such as a cutting procedure performed with a laser. As examples, cooled matter may be applied before, during, or after any of the steps described herein that may cause bleeding. For instance, cooled matter may be applied to the eye in connection with procedures involving rotating or shifting the conjunctiva.

Care may be taken when rotating or shifting the conjunctiva to attenuate tissue damage, such as de-vascularization and/or necrosis, resulting from, for example, excessive movement of the conjunctiva. In certain embodiments, portions of the conjunctiva to be moved may be separated from underlying tissue using known techniques, to thereby facilitate greater movement of the conjunctiva while controlling tissue damage. According to certain implementations, a fluid, such as an epinephrine-based fluid (e.g., anesthetic and/or vasal constrictor) may be introduced (e.g., in a vicinity of a boundary of the conjunctiva and one or more of the cornea, the choroid, and the ciliary muscle) before substantial movement and/or before separation from underlying layers of the conjunctiva. In modified embodiments, the fluid may have a viscosity greater than water. For instance, the fluid may comprise a gel, such as a transparent, water based gel.

Following any of the rotations and/or shifts of the conjunctiva described herein, and/or at any intermediate step, part or all of the conjunctiva being altered may be held with any known temporary or permanent means. For example, following movement back to, or back to and then slightly beyond, its naturally-occurring orientation, sutures, surgical tacks, screws or staples, and/or applinator-style attachments including adhesives may be applied to hold the conjunctiva in place.

Torquing or rotating of the conjunctiva may be possible using any of a variety of methods and devices. While being formed almost entirely of collagen, the conjunctiva is vascular and thus should be handled carefully, for example, to minimize bleeding. The conjunctiva may also be capable of being extensively stretched. Regarding movement of the conjunctiva (cf. FIG. 5b), as presently illustrated, the conjunctiva can be rotated using, for example, a tool, so that the angular locations of the markings are changed from their initial (i.e., pre-movement) marked angular positions. Following such movement (e.g., rotation), the conjunctiva may be held in the post-movement position using, for example, a conjunctival template device while some or all of the tissue treatments are subsequently applied.

Before torquing the conjunctiva, the conjunctiva may be, for example, ballooned with a fluid. For instance, a fluid (e.g., comprising epinephrine) may be inserted beneath the conjunctiva, to thereby separate the conjunctiva from the underlying sclera. According to one aspect of the present invention, a pair of incisions (e.g., top and bottom incisions) may be formed in the conjunctiva, and a tool having a pair of opposing legs may be inserted between the conjunctiva and the sclera. FIGS. 15a and 15b depict an embodiment of such a tool 61 having a pair of opposing legs 63 and 65. FIG. 15a is a side-elevation view of the tool 61, and FIG. 15b provides a top planar view of the tool 61 taken from a perspective of line 15b-15b' of FIG. 15a. The legs 63 and 65 comprise intermediate portions 67 and 69, respectively, and lower portions 71 and 73, respectively.

During use, the lower portions 71 and 73 can be inserted through the incisions of the conjunctiva so that they contact and rest upon the sclera and so that the intermediate portions 67 and 69 remain in and contact sidewalls of the incisions. In typical embodiments, dimensions of the pair of incisions can correspond to cross-sectional shapes of the intermediate portions 67 and 69 so that the intermediate portions 67 and 69 rest snugly within and contact the sidewalls of the incisions, but, on the other hand, so that sizes of the incisions are minimized to avoid unnecessary trauma to the conjunctiva.

As the tool 61 is rotated about a rotational axis 75, the lower portions 71 and 73 slide over (e.g., contacting or not contacting) the sclera and the intermediate portions 67 and 69 contact and apply rotational forces to the sidewalls of the incisions to thereby move (e.g., rotate) the conjunctiva. The tool 61 can thus be used to torque the conjunctiva in a first direction. Incisions can then be lased, for example, on opposite sides of each leg (to thereby form 4 incisions) with the incisions penetrating into and forming tissue treatments in the sclera. The conjunctiva may then be torqued further in the same direction followed by formation of additional tissue treatments in a similar manner, and/or may be torqued in a second direction opposite to the first followed to facilitate formation of additional tissue treatments in a similar manner. The torquing and tissue treatment forming processes may be repeated in any order. In a particular example, bottom and top incisions may be made in the conjunctiva in its original orientation at 90 and 270 degrees (respectively, 6 o'clock and 12 o'clock).

The tool legs 63 and 65 then may be inserted into the bottom and top incisions. The tool 61 then may be used to torque the conjunctiva in a clockwise direction by, for example, 45 degrees. Two kerfs may be lased on either side of each leg, followed by the conjunctiva being torqued 90 degrees about the rotational axis 75 in a counter-clockwise direction opposite to the first direction to a position 45 degrees counter-clockwise from the original orientation of the conjunctiva, whereby two kerfs again may be lased on either side of each leg. The conjunctiva then may be torqued to its original orientation followed by removal of the tool, or the tool may be removed and the conjunctiva allowed to assume its original orientation or some other orientation. When the conjunctiva assumes its original orientation, the procedure just described results in four double kerfs located at 45, 135, 225, and 315 degrees on the polar coordinate system introduced above. That is, four double kerfs are located at northeast, northwest, southwest, and southeast positions of the eye relative to, for example, a pupil that defines an origin for the polar coordinate system and a polar axis (e.g. east or zero degrees) as illustrated by polar axis 38 in FIG. 1.

Figure 16A:
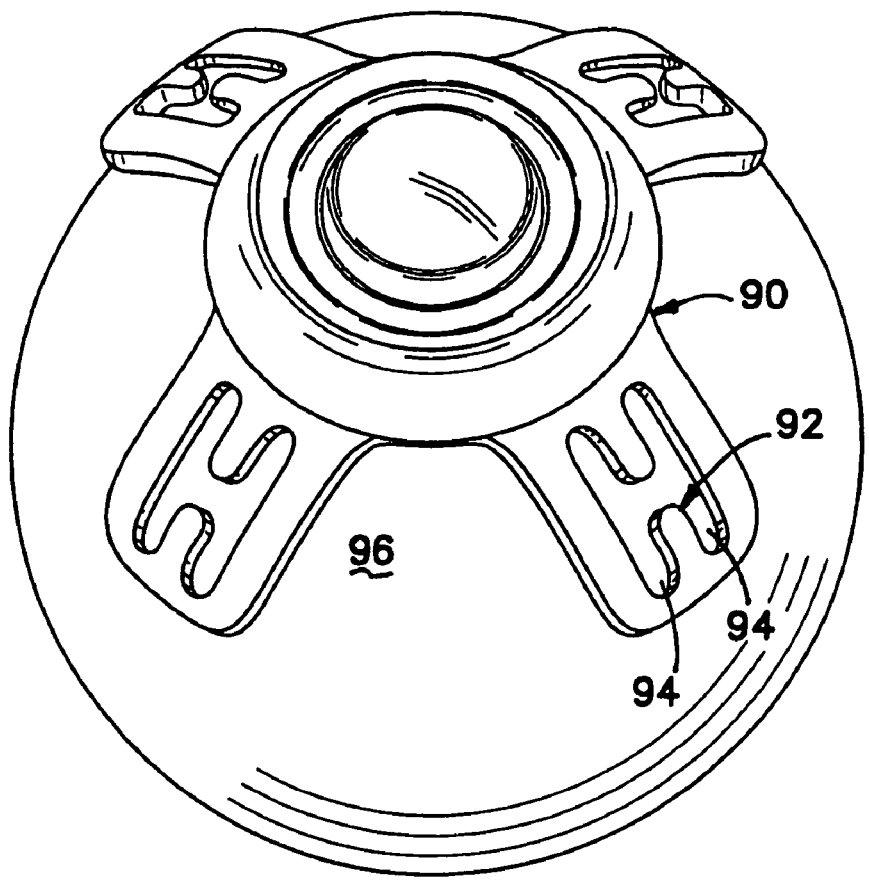
FIGS. 16A-18 are schematic illustrations corresponding to types of procedures that can be implemented to treat an eye according to third aspects of the present invention.
Figure 16B:
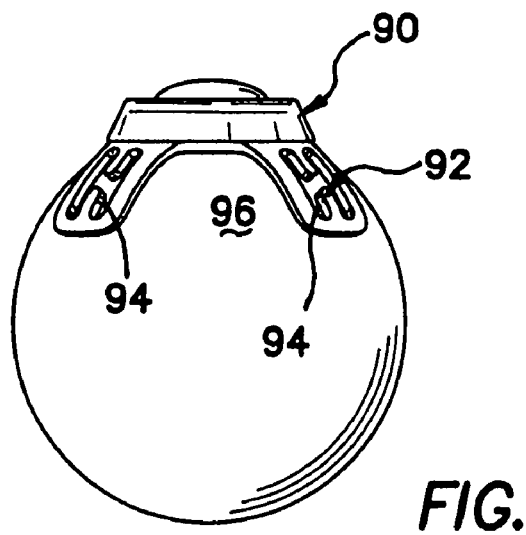

According to implementations of the method just described, a conjunctival template device may be employed to facilitate the formation of tissue treatments under the conjunctiva. FIGS. 16*a* and 16*b* are pictorial diagrams showing, respectively, perspective and side-elevation views of an embodiment of a conjunctival template device 90. The illustrated embodiment of the conjunctival template device 90 may include a built-in template 92 comprising, for example, one or more slots 94 that may be used for positioning the tissue treatments (e.g., incisions) in a region 96 of the conjunctiva and/or sclera.

The built-in template 92 may comprise four arm implements disposed at 0, 90, 180 and 270 degrees, and the slots 94 may comprise one or more slots disposed in each arm implement, such as, for example, two parallel slots disposed in each arm implement or, as shown, an 'H' shape of two slots disposed in each arm implement. Tissue treatments or tissue treatment groupings may be formed under the conjunctiva corresponding to the shapes of the slots, or may have reduced sizes (e.g., formed by an output tip as apertures having sizes that are about the same as a cross-sectional area of the output tip) with the tissue treatments or tissue treatment groupings in the underlying sclera comprising, for example, elongated shapes (e.g., elongated kerfs) extending radially outwardly at constant or substantially constant angular positions (cf. FIGS. 12*a* and 14*a*). Thus, an aperture-shaped tissue treatment may be formed in the conjunctiva under a center region of each slot, and elongated tissue treatments may be formed in the sclera under and corresponding in shape to each slot.

In embodiments wherein the two slots (e.g., parallel slots) in each arm implement are partially connected by a relatively small transverse slot to form an "H-shaped" slot in each arm implement, an output tip, such as a cylindrically-shaped sapphire laser output tip, can be inserted into the transverse slot and through (e.g., via formation of a small incision) the conjunctiva so that the output tip rests, for example, between the conjunctiva and the sclera. To facilitate the insertions of the output tip through the conjunctiva in vicinities of (e.g., between pairs of) treatment areas, tissue treatments (e.g., aperture-shaped tissue treatments having shapes corresponding to a cross-sectional shape of the output tip) may be formed in the conjunctiva corresponding in number and position to the transverse slots. Following placement of the output tip between two parallel slots in a center area of a transverse slot, and through an aperture-shaped tissue treatment of the conjunctiva, the output tip can be moved in a first direction in the transverse direction (e.g., the direction parallel to an elongate axis of the transverse slot) into a first one of the two slots and can be moved in a second direction opposite to the first direction into a second one of the two parallel slots.

According to an aspect of the present invention, the conjunctival template device can be held in a fixed position relative to the eye (e.g., relative to the cornea), so that movement of the output tip in a given direction tends to move the conjunctiva (e.g., a portion of the conjunctiva in a vicinity of the output tip) in the given direction. For example, the conjunctival template device can be held in a fixed position relative to the eye by way of a cornea (and/or limbus) contacting portion of the conjunctival template device engaging a portion of the eye in a vicinity of the cornea to resist rotation of the conjunctival template device. For instance, a structure comprising a template guide, such as a built-in template, can be placed (e.g., secured with suction), for example, to the limbus and contain or provide indications pertaining to one or more of proper locations, sizes and shapes (e.g., lengths) of tissue treatments, and may also contain a depth guide.

Suction may be applied to the contacting portion, wherein the contacting portion may be constructed and operated as described in connection with FIGS. 19*a*-19*c*. In one illustrative example, movement of the output tip from the center area of the transverse slot in the first direction moves the conjunctiva (e.g., a portion of the conjunctiva) in the first direction and movement of the output tip from the center area of the transverse slot in the second direction move the conjunctiva (e.g., a portion of the conjunctiva) in the second direction. According to another illustrative example, movement of the output tip from the center area of the transverse slot in the first direction moves a portion of the conjunctiva a corresponding (e.g., approximately equal) distance in the first direction, and movement of the output tip from the center area of the transverse slot in the second direction moves a portion of the conjunctiva a corresponding (e.g., approximately equal) distance in the second direction. Thus, in accordance with an aspect of the present invention, the conjunctiva can be moved (e.g., rotated or torqued) or shifted in two opposing directions to facilitate formation of two different tissue treatments in the underlying sclera.

In a particular example wherein an output tip is inserted through an aperture-shaped tissue treatment of the conjunctiva beneath a central region of an H-shaped slot, the output tip can be moved (moving a portion of the conjunctiva in the same direction with it) into a first one of two slots forming the H-shaped slot, at which time the output tip can form an elongated tissue treatment as described previously with reference to FIGS. 12a and 14a. The output tip then can be moved back through the central region of the H-shaped slot and then moved (carrying a portion of the conjunctiva in the same direction with it) into the other parallel slot, at which time another elongated tissue treatment can be formed in the same manner as described previously. The output tip then can be moved back to the central region of the H-shaped slot and withdrawn from the aperture-shaped tissue treatment. Subsequently, the single (e.g., circular shaped) tissue treatment in the conjunctiva between the two elongated tissue treatments in the sclera can be closed using, for example, bipolar forceps, sutures and/or glue. In a modified embodiment, coagulating energy may be applied to the tissue treatment regions before or during formations thereof.

Constructions, operations, and modifications, of and to this conjunctival rotating device can be similar at least in part to, substantially the same as, or identical to, that described above. For example, a centrally-disposed contacting portion of the conjunctival rotating device may be constructed and operated as described above so that suction can be applied to hold the contacting portion to the cornea. An output tip can be inserted through an aperture-shaped tissue treatment of the conjunctiva beneath a central region of the window, followed by movement of the output tip in the first direction to the same location as described above and formation of an elongated tissue treatment in the same place and manner as discussed above, followed by movement of the output tip in the second direction to the same region as described above and formation of an elongated tissue treatment in the same manner and position as discussed above.

Figure 17A:
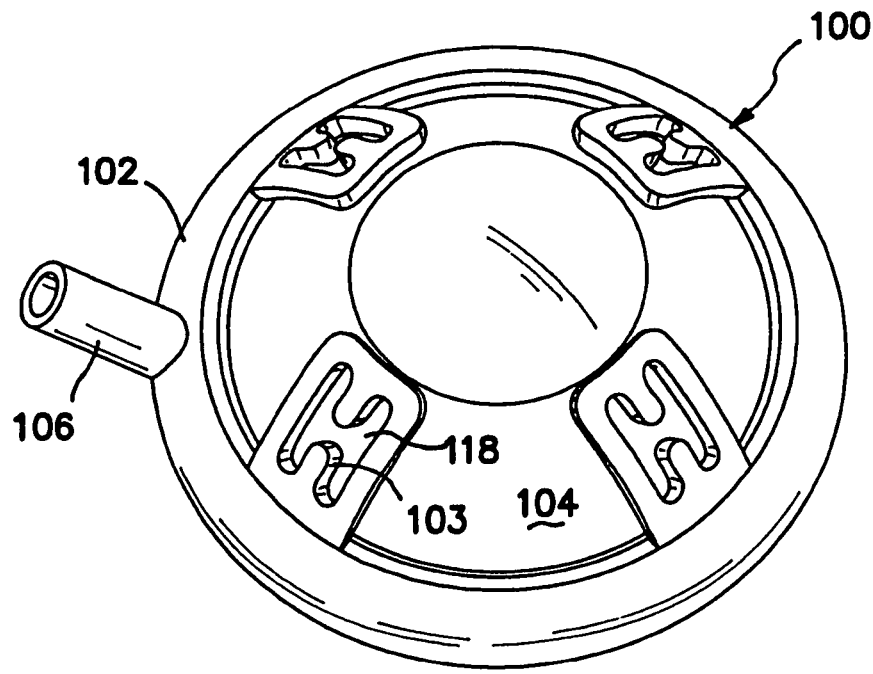
Figure 17B:
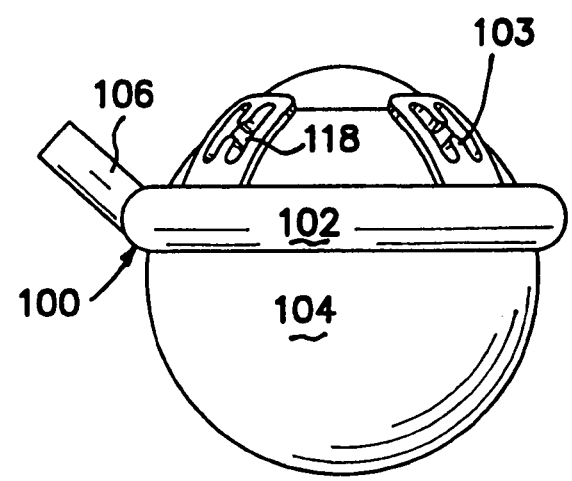
Figure 18:
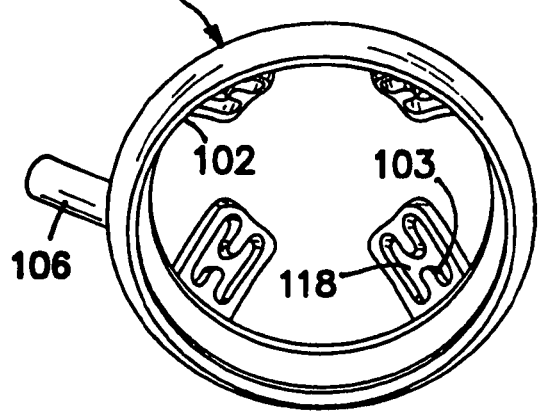

In other embodiments, an applicator device can be placed on a surface of the eye, for example, to drain or force-out blood and/or to attenuate or restrict blood flow. For example, perspective and side-elevation views of an embodiment of an applicator device 100 are shown in FIGS. 17a and 17b, respectively, and an underside perspective view of the applicator device 100 is shown in FIG. 18. The illustrated embodiment of an applicator device 100 may substantially cover and/or seal-off all or part of an area of an eye 104 being treated. The applicator device 100 may comprise a suction ring 102 around a periphery of the applicator device 100, the suction ring 102 acting to provide an effective seal with a surface of the eye 104.

According to one implementation, suction is applied to provide a tourniquet-like effect on the conjunctiva so that pooling of liquids (e.g., blood) is attenuated or eliminated. One implementation comprises positioning an applicator device with suction in a vicinity where the blood vessels come to rest on the eye. The embodiment further comprises a tube 106 being fabricated in the illustrated embodiment as part of the suction ring 102. Blood or other fluids may be held away from a treatment area; and/or blood or other fluids collecting, for example, between the surface of the eye 104 and the applicator device 100 may be drawn off through the tube 106 when suction is applied to the tube 106 from an external source. The applicator device 100 may serve as a guide (e.g., a stencil or template) for the positioning and/or formation of tissue treatments (e.g., incisions), wherein the suction may act, for example, to secure the applicator device 100 to the eye 104 during those procedures.

Alternatively, or additionally, a handle may be used to secure the applicator device 100 to the eye 104 during the same or similar procedures. In modified embodiments, the applicator device may comprise markings and/or may comprise openings for the above-described feet 63 and 65 (FIGS. 15a and 15b). The exemplary configuration of an embodiment of an applicator device 100 illustrated in FIGS. 17a and 17b can comprise a template 103 having slots (e.g., arcuate slots) at the above-described northeast, northwest, southwest, and southeast positions configured for use as described herein. For instance, tissue treatments or tissue treatment groupings may be formed in the conjunctiva corresponding to at least parts of the shapes of the slots, or may have reduced sizes (e.g., formed by an output tip as apertures having sizes that are about the same as a cross-sectional area of the output tip) with the tissue treatments or tissue treatment groupings in the underlying sclera comprising, for example, elongated shapes (e.g., elongated kerfs) extending radially outwardly at constant or substantially constant angular positions. The illustrated embodiment comprises a template 103 incorporating "H-shaped" apertures 118 configured for use as described herein. For example, tissue treatments or tissue treatment groupings may be formed in the conjunctiva corresponding to or reduced in size relative to the shapes of the slots, with the tissue treatments or tissue treatment groupings in the underlying sclera comprising, for example, elongated shapes.

FIGS. 19a-19c depict an embodiment of a conjunctival displacement device 122. Top perspective bottom perspective, and side-elevation views of the conjunctival displacement device 122 are provided in FIGS. 19a, 19b, and 19c, respectively. The conjunctival displacement device 122 may be employed to facilitate, for example, one or more of displacement of the conjunctiva and placement of tissue treatments into the sclera. An illustrated embodiment of the conjunctival displacement device 122 includes a contacting portion 125 and one or more arm implements 127. According to an exemplary embodiment, the contacting portion 125 can be constructed, for example, to contact a central part of the eye such as the cornea and/or limbus, and the one or more arm implements 127 can be constructed for facilitating positioning on a non-central part of the eye such as over the conjunctiva and sclera.

In a modified embodiment, the contacting portion 125 may be, in whole or in part, non-centrally disposed and/or configured not to contact the cornea and limbus. For example, the contacting portion may alternatively or additionally comprise a suction ring and tube, such as the suction ring 102 and tube 106 depicted and described in connection with FIGS. 17a and 17b. Typical implementations of this modified embodiment may still comprise an arm implement or implements constructed to rotate about a central portion of the device (e.g., about a central portion of the eye), but wherein this central portion of the device may or may not necessarily contact the eye as a result of, for example, the suction ring providing a contact. Such typical implementations thus may comprise centrally-disposed portions that are similar to the contacting portion 125, with a difference being that the modified centrally-disposed portions do not contact the cornea or limbus.

Support arms may be provided, for example, extending from the modified centrally-disposed portion to the suction ring to thereby support the centrally-disposed portion above the surface of the eye. One or more support bridges (e.g., two support bridges disposed 180 degrees apart) may be provided, for example. To the extent the support bridges impede optimal (e.g., 180 or 360 degree) rotation of the one or more arm implements, two or more arm implements may be provided and/or templates (infra) may be provided on each of the arm implements. In an embodiment comprising two arm implements, each being disposed, for example, 180 degrees from the other and comprising a template, rotation of the two opposing arm implements can provide an effective or optimal angular range of movement to the arm implement pair.

As presently embodied, the arm implement 127 includes a user aid or guide comprising, for example, at least one template 132 that may be used for positioning tissue treatments (e.g., incisions) in regions of the conjunctiva and/or sclera. As presently embodied, the template 132 may comprise, for example, an "H-shaped" slot, or, as another example, two slots (e.g., parallel slots).

Constructions, operations, and modification, of and to the conjunctival displacement device 122 can, at least in part, be similar to or substantially the same as that described above. For instance, the contacting portion 125 of the conjunctival displacement device 122 may be provided with a tube 135, which may be constructed and operated in whole or in part as described above, with reference to for example tube 106, including application of suction via, for example, tube 135 to facilitate securement or fixation of the contacting portion 125 to the eye. The tube 135 can be fabricated in the illustrated embodiment as a separate or integral part of the contacting portion 125. When the tube 135 is used in combination with the contacting portion 125, and when, for example, suction is applied to the tube 135 from an external source, the combination of tube 135 and contacting portion 125 may facilitate the provision of one or more of the following: resist shifting forces imparted onto the contacting portion 125; resist rotational forces about the center axis 129 that may be imparted onto the contacting portion 125; provide an effective seal with one or more of the cornea and limbus of the eye; hold blood or other fluids away from a treatment area; and draw blood or other fluids off through the tube 135. Alternatively, or additionally, a handle may be used to secure the conjunctival displacement device 122 to the eye during the same or similar procedures.

According to one aspect of the present invention, alignment indicia 141 are disposed on the contacting portion 125 for aiding a user in aligning the conjunctival displacement device 122 and, more particularly, the contacting portion 125 to facilitate placement of tissue treatments. In a typical implementation, the user may align top and bottom alignment indicia 141 with south and north (i.e., 90 and 270 degree) directions of the eye and/or align right and left alignment indicia 141 with east and west (i.e., 0 and 180 degree) directions, or right and left corners, of the eye.

According to another aspect of the present invention, position engagement structure is provided on one or more of the contacting portion 125 and the arm implement 127. As embodied herein, the position engagement structure comprises indentations 144 disposed at predetermined locations on the contacting portion 125 and protuberances 146 disposed on the arm implement wherein the protuberances 146 are sized and shaped for rotation-inhibiting engagement with the indentations 144. The arm implement 127 may be provided as a single arm implement, comprising structure and elements as depicted and/or further comprising position engagement structure as described above, or the arm implement 127 may be provided in combination with a secondary arm implement 128.

Provision of the arm implement 127 as a single implement may be accomplished with or without protuberances being affixed to the arm implement 127 for rotation-locking engagement with corresponding indentations of the contacting portion. Typical embodiments may further comprise a secondary arm implement 128, which may comprise protuberances affixed to the secondary arm implement for rotation-locking engagement with corresponding indentations of the contacting portion. For instance, in certain embodiments, such as illustrated in the drawings, only the secondary arm implement 128 may be provided with protuberances to the exclusion of the arm implement 127. While one or more arm implements 127 may be provided, alone or in combination with one or more secondary arm implements 128, certain illustrated embodiments such as elucidated in the figures can comprises a pair consisting essentially of one arm implement 127 (e.g., without protuberances) and one secondary arm implement 128 (e.g., with protuberances) being provided on each contacting portion 125.

In modified embodiments, two or more arm implements 127 (e.g., without protuberances) may be provided with one secondary arm implement 128 (e.g., with protuberances) on each contacting portion 125. Other embodiments may comprise two or more arm implements 127 (e.g., disposed 180 degrees apart). For instance, two or more arm implements 127 may be provided, without any secondary arm implements 128, on each contacting portion 125, wherein one or more of the arm implements 127 comprises protuberances. In particular implementations, a single one, or both, of the arm implements 127 may be provided with protuberances.

When, for example, the contacting portion 125 comprises a centrally-disposed contacting portion 125, the arm implement 127 may be rotatable, or removable and securable in different angular positions, about the centrally-disposed contacting portion 125. In typical embodiments, the arm implement 127 may be constructed, using any material and structure known to those skilled in the art to be suitable or operable for such purposes, to be rotatable about a center axis 129 of the contacting portion 125.

Embodiments comprising one or more arm implements 127 and one or more secondary arm implements 128 may comprise connecting structure coupled between one or more of the arm implements 127 and one or more secondary arm implements 128. In an example, the connecting structure can comprise a connecting ring 131, disposed concentrically about the center axis and linking rotational movement of the arm implement 127 to rotational movement of the secondary arm implement 128. In a particular example, the connecting ring 131 fixes rotational movement of the arm implement 127 to rotational movement of the secondary arm implement 128, so that rotational movement of either one of the arm implement 127 and the secondary arm implement 128 results in corresponding (e.g., identical) rotational movement of the other of the arm implement 127 and the secondary arm implement 128. Thus, in this example, the arm implement 127, the secondary arm implement 128, and the connecting structure (e.g., connecting ring 131) are all connected and together can be rotated, relative to the contacting portion 125. In other embodiments, connecting structure is omitted, in whole or in part, so that one or more of the arm implements 127 is not coupled to one or more of the secondary arm implements 128.

In exemplary embodiments, rotation of the arm implement 127, relative to the contacting portion 125 that is fixed onto the eye, facilitates rotation or movement of the conjunctiva. At least one conjunctiva tongue can be positioned, for example, on each arm implement for gripping and moving at least a local portion of the conjunctiva according to typical embodiments. In the illustrated embodiment, two conjunctiva tongues 138 can be positioned on the arm implement 127, and further can be positioned on opposing sides of the arm implement 127 as depicted, for example, in FIG. 19b.

In use, a gripping incision (not shown) can be formed in the conjunctiva to accommodate either one of the conjunctiva tongues 138. A size and shape of the gripping incision can be predetermined or varied according to a size and shape of the conjunctiva tongue or tongues. For example, in an embodiment as shown in FIG. 19a wherein the conjunctiva tongue 138 has an edge with a length, as measured in a direction d1, of about 6 mm, the gripping incision may be formed in the conjunctiva to have a complementary or accommodating shape with a length of about 10 mm as measured in a direction parallel to the direction d1.

The one of the two tongues that is disposed on a leading edge of the arm implement 127, when the arm implement 127 is rotated in a clockwise direction, can be inserted into a gripping incision followed by rotation in the clockwise direction of the arm implement by a predetermined angular amount whereby the movement invokes a corresponding movement of the conjunctiva in the same direction to the same or a lesser degree. For example, the arm implement 127 may be rotated (e.g., about 45 degrees) in the clockwise direction until a protuberance on the secondary arm implement 128 lockingly engages with a corresponding indentation 144 in the contacting portion 125, at which time one or more tissue treatments may be formed as described above.

The two proximal ends (i.e., located closest to the tube 135) may then be pinched or otherwise moved toward one another (e.g., pinched together) to release the protuberance 146 from engagement within the indentation 144 and to facilitate additional rotation. For example, the additional rotation may comprise a rotation (e.g., about 45 degrees) in the opposite (e.g., counter-clockwise) direction until the one tongue can be removed from the gripping incision and the other one of the two tongues can be inserted into the same gripping incision, followed by continued rotation in the counter-clockwise direction of the arm implement by a predetermined angular amount whereby the movement invokes a corresponding movement of the conjunctiva in the same direction to the same or a lesser degree.

For example, the continued rotation of the arm implement 127 in the counter-clockwise direction may comprise a continued rotation of about 45 degrees until a protuberance on the secondary arm implement 128 lockingly engages with a corresponding indentation 144 in the contacting portion 125, at which time one or more tissue treatments may be formed as described above. The two proximal ends (i.e., located closest to the tube 135) may again be moved toward one another to release the protuberance 146 from engagement within the indentation 144 and optionally to facilitate additional rotation. At this point, tissue treatments may have been formed, for example, in southwest and southeast quadrants of the sclera. In a similar manner, tissue treatments may further be formed in northeast and northwest quadrants of the sclera.

In accordance with one aspect of the present invention, one or more conjunctiva catches can be provided on the arm implement. Each conjunctive catch may comprise, in typical embodiments, a conjunctiva collecting ridge 148. In modified embodiments, other embodiments (e.g., of different shapes, sizes and locations on the arm implement) of conjunctiva catches may be formed, alone or in combination with the illustrated, or modified, conjunctiva collecting ridges. Moreover, the one or more conjunctiva catches can be provided on corresponding arm implements alone or in combination with the one or more conjunctiva tongues.

As presently embodied, the number of conjunctiva catches provided corresponds to the number of conjunctiva tongues disposed on each arm implement. According to typical embodiments, each conjunctiva catch is disposed between a conjunctiva tongue and a template of a corresponding arm implement to catch and/or carry portions of the conjunctiva as the arm implement is rotated. For instance, a conjunctiva collecting ridge can prevent conjunctival tissue from moving up and over into the template as the arm implement is rotated.

Regarding anti-rotational structures or properties of the contacting portion, according to certain aspects of the present invention, one or more paws (not shown) may be provided to reach back in a direction measured from the cornea to the retina and to contact a gripping region of the eye for facilitating a securement of the contacting portion. The securement may operate to resist or prevent shifting or rotational movement of the contacting portion. Embodiments incorporating one or more paws may be implemented alone or in combination with embodiments wherein suction (e.g., via a tube) is employed to facilitate securement of the contacting portion. Each paw may comprise a size tailored to fit a size of the patient's eye and/or may comprise, for example, a polymer such as polymethylmethacrylate (PMMA). Each paw further may be provided as part of an arm implement or a secondary arm implement or may be formed to extend individually back to the gripping region. Shapes of paws may take on various forms such as wedge shapes, and surfaces of paws may comprise tiny cleats, barbs, corrugations, ribs, suction cups, adhesives, or other devices for producing a gripping action between a surface or layer of the eye and the paw as known to those skilled in the art.

In certain embodiments, a paw, such as, for example, an inter-layer paw, may be secured between two layers of the eye, such as between the conjunctiva and the sclera. The inter-layer paw may have any of the structures and functions discussed previously, such as a wedge shape, and further may comprise, for example, an expandable material that can facilitate an increase or change in size along at least one dimension of the inter-layer paw after positioning thereof in a gripping region. In one example, the paw may comprise an inflatable wedge, which can be inserted or otherwise positioned in a vicinity of a gripping region and then pumped (e.g., via a line and/or reservoir that can be squeezed by a hand of a user to direct fluid into the paw, with, for example, one squeezable line being provided for each paw) with water or air for purchase. A regulator or release valve may be provided to prevent over inflation of the paw. In other embodiments, rather than being inflatable, one or more of the paws may comprise an expandable material, such as an expandable foam that may be flattened or otherwise reduced in size before insertion, wherein following insertion (e.g., 10-15 seconds following insertion) and positioning in a gripping region, the paw expands under its own memory and returns to an original size. For any embodiments employing a paw, it may be advantageous to have at least one of the surfaces of the paw configured as a low-friction surface to facilitate insertion and/or positioning of the paw and, subsequently, to have at least one surface of the paw configured as a relatively high-friction surface to facilitate gripping of the paw to the eye. To this end, specialized surfaces (e.g., relatively nonporous surfaces that are lubricated using, for example, Viscasil®, to facilitate relatively low-friction insertion and that subsequently, as a consequence of being relatively nonporous for example, become relatively high-friction surfaces) may be implemented as are known to those skilled in the art.

In accordance with other configurations of the present invention, template or slot locations can comprise "stops" that physically or visually provide or facilitate stopping indications or functions to the upper portions 77 and 79 and/or to a surgeon's torquing and/or tissue-treatment forming actions. For instance, the stops may operate to limit torquing movement by the tool 61 to plus or minus 45 degree ranges of motion.

The applicator device can be fabricated, for example, as part of a speculum. In one embodiment, the applicator device may be constructed with a plurality of hook-like members, which members may operate to provide the functionality of a speculum.

Suction may be provided, as well, by operation of the applinator device. In exemplary implementations, the applinator device may be constructed (e.g., at a time of manufacture or via manipulation or configuration of the applinator device at a time of application to the eye) to provide suction in a vicinity of connective tissue of the eye.

Connective tissue is determined by the placement of the muscles and the tissue that is attached to the muscles. It is believed that the connective tissue is located at the superior formix of the conjunctiva, so that application of suction using a suction ring may reduce the supply of blood to the conjunctival tissue. Suction may be provided on the underside of the applinator device in typical embodiments, wherein for example a contacting portion of the applinator device is fixed and provides the suction, and wherein for example a template portion of the applinator device can be rotated. A piezoelectric or other motor device can be provided in certain implementations to automatically facilitate application of cuts along, for example, each template or slot and/or to automatically move the applinator device through predetermined ranges of motion for positioning and/or provision of tissue treatments. In certain implementations, such suction may be implemented to contact and facilitate movement and/or separation (e.g., lifting) of the conjunctiva from the sclera.

Figure 24A:
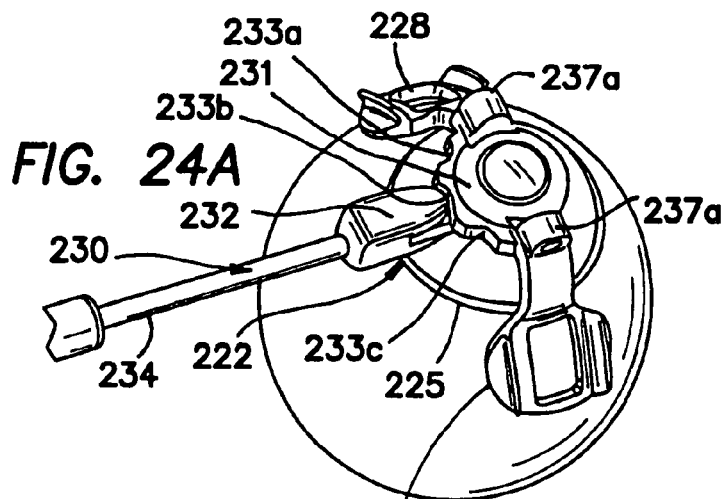
FIGS. 24A-24C are schematic illustrations corresponding to types of structures and corresponding processes that can be implemented to treat an eye according to sixth aspects of the present invention.
Figure 24B:
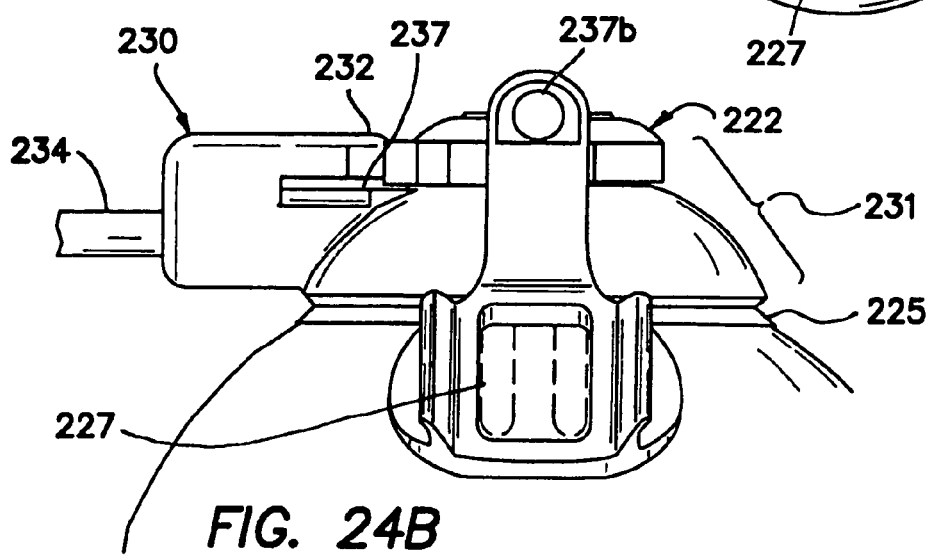
Figure 24C:
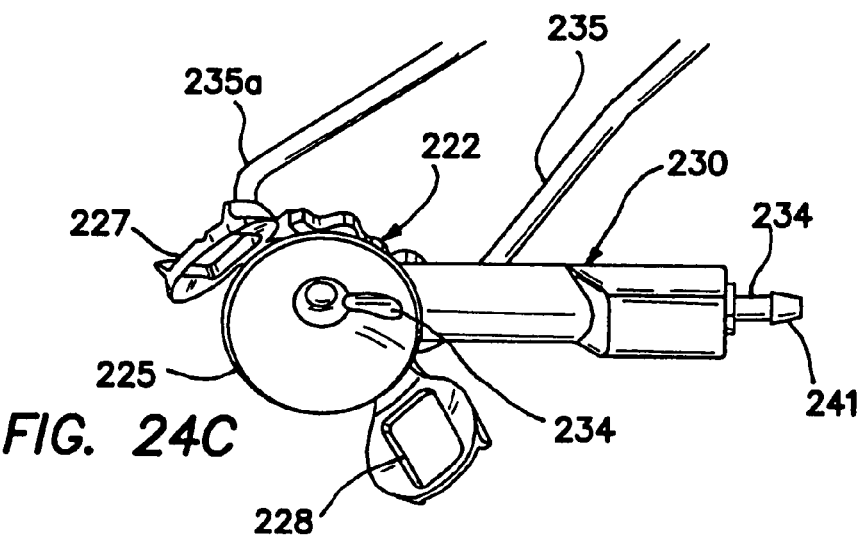

In other embodiments and implementations, the conjunctival displacement device 122 (FIGS. 19a-19c), or any previous device such as the conjunctival template device 90 (FIG. 16a-16b), can be constructed so that the two slots (e.g., parallel slots) in each arm implement are substantially entirely connected by a relatively large slot (e.g., having the same length as that of the two parallel slots) to thereby form a single rectangular-shaped slot or window in each arm implement, as shown, for example, in FIGS. 24a-24c.

Figure 20:
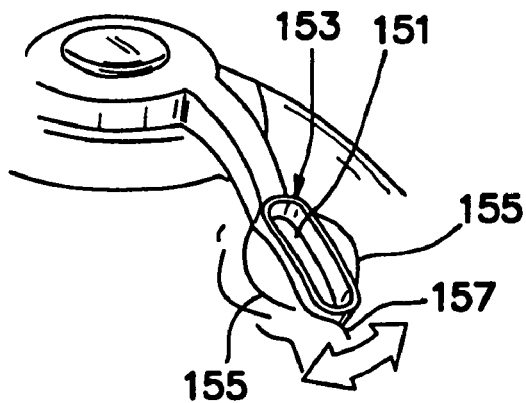

In other embodiments, the single rectangular-shaped window in each arm implement can have the same or a greater length than the two parallel slots but a reduced width, such as shown in FIG. 20, wherein a single narrow channel is formed in each arm implement or in a single arm implement if only one is used. With reference to that figure, the narrow channel 151 can provide a greater and/or different visibility of areas surrounding a procedural site. In accordance with another aspect, the arm implement 153 may be operated with a smaller footprint on the conjunctiva than other devices. For example, the arm implement 153 can be provided with two conjunctiva tongues 155 positioned on, for example, opposing sides of the arm implement 153, for fitting into a single-slot incision 157 rather than two incisions or an enlarged I-shaped incision (cf. FIG. 28, infra).

One of the conjunctiva tongues 155 can be placed into the single-slot incision during the formation of each of two tissue treatments, or both of the conjunctiva tongues 155 can be placed into a single-slot incision at the same time for the formation of each corresponding tissue treatment. According to one aspect of the present invention, each tissue treatment may be formed in the conjunctiva corresponding to the shape of the narrow channel, or may have a reduced size (e.g., formed by a fiber optic tip as an aperture having a size that is about the same as a cross-sectional area of the fiber optic tip) with the tissue treatment in the underlying sclera comprising an elongated shape (e.g., elongated kerf) extending radially outwardly at a substantially constant angular position and approximating the shape of the narrow channel 151. In this embodiment or any of the embodiments described herein, the mentioned aperture which can be formed in the conjunctiva may be formed in a location corresponding to the posterior part of the window, slot, or narrow channel, so that, for example, a patient's eyelid will be more likely to cover the fiber-optic-tip entry point (i.e., the mentioned aperture) following the procedure.

Regarding the referenced FIGS. 24a, 24b and 24c, a conjunctival displacement device 222 is provided with a contacting portion 225 (e.g., a cornea suction cup formed of silicon) and a handle 230, which can serve as a positioning tool or stem. Typical implementations of this embodiment may comprise a first arm implement 227 and a second arm implement 228, each being disposed, for example, 180 degrees from the other and comprising a template, wherein rotation of the two opposing arm implements can provide an effective or optimal angular range of movement to the arm implement pair.

An upper, rotatable portion 231 of the conjunctival displacement device 222 is fixed to the first arm implement 227 and the second arm implement 228. The handle 230, on the other hand, is fixed (e.g., integrally molded into the cup of the contacting portion 225) to the contacting portion 225. A nub 232 of the handle 230 fits into three indentations 233a, 233b and 233c formed by rounded teeth, which three indentations correspond to the three orientations assumable by the handle 230.

In modified embodiments, the nub may comprise a shape of a cylinder, which is oriented, for example, to have its longitudinal axis generally parallel with a rotational axis of the upper, rotatable portion 231, so that an arcuate surface of the cylinder fits into complimentary-shaped surfaces of the three indentations 233a, 233b and 233c. The cylinder or other similar structure may be referred to as an indexing detent, which, as with the nub 232 embodiment, can be integrally molded into the contacting portion 225.

The first arm implement 227 and the second arm implement 228 may each be referred to as a laser guide paddle, which pivots between and locks in three positions each separated by 45 degrees as presently embodied. Also, the templates of the first arm implement 227 and the second arm implement 228 may be referred to as swivel-lock templates.

Referring to FIG. 24b, a gap 237 permits the nub 232 to be deflected as it swivel-indexes the teeth. This figure also depicts in phantom the locations of two tissue treatments to be formed beneath the conjunctiva in the sclera according to an outline of the window of the first arm implement 227.

The handle 230 may be coupled to the upper, rotatable portion 231 of the conjunctival displacement device 222 at various angular orientations. For instance, as illustrated with particular reference to FIG. 24a, the handle 230 can be secured at a central orientation, as shown, and can also be secured at two secondary orientations angularly disposed at plus or minus 45 degree orientations from the central orientation.

Being fixed to the contacting portion 225, movement of the handle 230 to either of the two secondary orientations results in corresponding rotational movement of the first arm implement 227 and the second arm implement 228.

In one favored implementation, the handle 230 is not fixed to the upper, rotatable portion 231 of the conjunctival displacement device 222. Instead, part or all of the handle 230 is fixed (e.g., integrally molded) into the contacting portion 225, or is removably secured thereto. Here, the rounded teeth forming the three indentations 233a, 233b and 233c, can be integrally formed with or otherwise affixed to (i.e., rotationally fixed relative to) the upper, rotatable portion 231. Also, the nub, cylinder or other similar structure 232 can be integrally molded into the contacting portion 225.

The handle 230 may optionally be constructed to comprise a vacuum tube 234, which may be constructed and operated in whole or in part as described above, with reference, for example, to tube 106 or tube 235. The vacuum tube 234 can be disposed within the handle 230, wherein the handle can lead to and be coupled to a caliper mount.

In one implementation, the handle 230 is formed with two large fingers (c.f. left side of FIG. 30) for attaching to calipers. Also, the vacuum tube 234 can comprise a vacuum tube fitting 241 as shown in FIG. 24*c*. The perspective underside view of the conjunctival displacement device 222 depicted in FIG. 24*c* elucidates an opening of the vacuum tube 234, which may be referred to as a vacuum port and which is formed to generate a flush-surface opening on an inner surface of the contacting portion 225.

According to embodiments comprising a vacuum tube 234, the cornea suction cup of the contacting portion 225 can be formed of an elastomeric material and can be mounted to the cornea via an application of vacuum pressure from the vacuum tube 234. In this and other embodiments comprising a source of vacuum, the source of vacuum can serve as an aspiration source for removing unwanted fluids which may accumulate during a procedure.

In addition to the handle 230, a twist tool 235 may be provided in the form of, for example, a rigid or semi-rigid loop. Ends of the twist tool 235 can be removably inserted into two twist-tool receptacles 237*a* and 237*b*, for enabling application of rotational forces to the upper, rotatable portion 231. In particular, a first end of the twist tool 235 fits into a first twist-tool receptacle 237*a*, and a second end of the twist tool 235 fits into a second twist-tool receptacle 237*b*.

Other implementations may omit the twist tool, nub, indentations, and/or related structure, such as, for example, embodiments wherein a conjunctival displacement device is provided with a contacting portion that is coupled to a first arm implement, a second arm implement, a third arm implement and a fourth arm implement. One or more (e.g., preferably all) of the first arm implement, second arm implement, third arm implement and fourth arm implement may be rotationally fixed, relative to the contacting portion.

The first arm implement, second arm implement, third arm implement and fourth arm implement may be angularly spaced, one from another, evenly (e.g., having center points separated one from another by 90 degrees), and may be referred to collectively as a four quadrant template/laser guide.

With reference, for example, back to FIG. 19*c*, any of the arm implements described herein can be configured to be disposed on (e.g., in contact with) or within (e.g., by way of one or more conjunctiva tongues) an incision of the conjunctiva. In other embodiments, with reference, for example, to the side-elevation view of FIG. 31*b*, infra, any of the arm implements described herein can additionally, or alternatively, be configured to be disposed a relatively small distance above the conjunctiva and/or sclera surfaces, such as, for example, a distance of about 1.5 mm. This distance can allow for ballooning of the conjunctiva above the sclera, as shown in FIG. 31*b*.

In accordance with one implementation of the invention, a tool and/or technique can be provided for placement into contact with the conjunctiva, for example, in the center of a template or window of an arm implement, after which the tool can move (e.g., by suction-gripping and lifting) the conjunctiva away from the sclera, along with filling of the space created between the conjunctiva and sclera with fluid, followed by or coupled with a securing of an eyelet or other spreader implement, described infra, to the conjunctiva (e.g., an eyelet can be secured with conjunctiva tongues in a neutral or central portion of the window).

Any of these types of arm-implement embodiments can be used with or without conjunctiva tongues. In particular implementations, wherein conjunctiva tongues are not formed on the arm implements or are formed but not used, and wherein the arm implements are configured either to contact or to hover above the eye surface, eyelets may be constructed and used within the windows (e.g., templates) formed by the arm implements.

Figure 25:
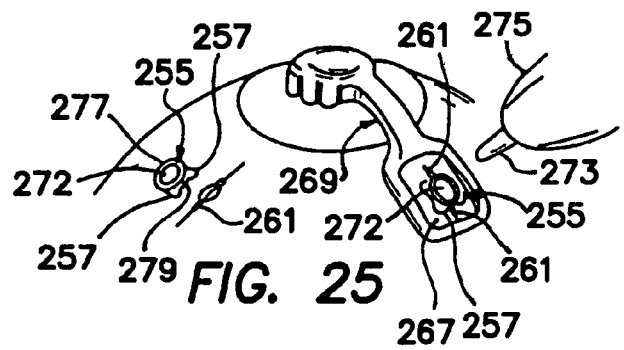
FIGS. 25-28B are schematic illustrations corresponding to types of devices and methods that can be implemented to treat an eye according to seventh aspects of the present invention.

While the eyelets of the present invention may be operated with any window or template configuration, and any corresponding arm-implement structure disclosed herein, one particular implementation is elucidated with reference to FIG. 25. In that figure, a rectangular-shaped window 267 is provided in an arm implement 269. In accordance with one aspect, the arm implement 269 may be sequentially positioned in four tissue-treatment site quadrants, and in accordance with another aspect two matching arm implements may be provided with the combined structure being rotatable to assume two positions so that all of the four quadrants may be covered by the two arm implements. In yet another embodiment, four arm implements may be provided as disclosed herein.

Figure 26B:
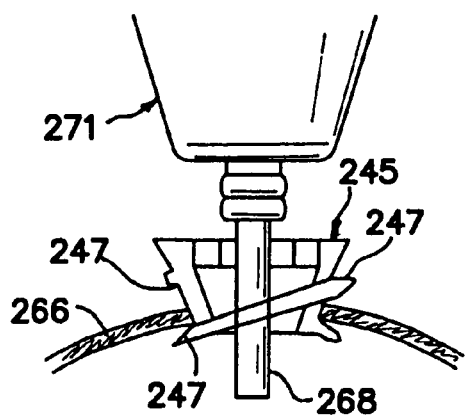
Figure 26A:
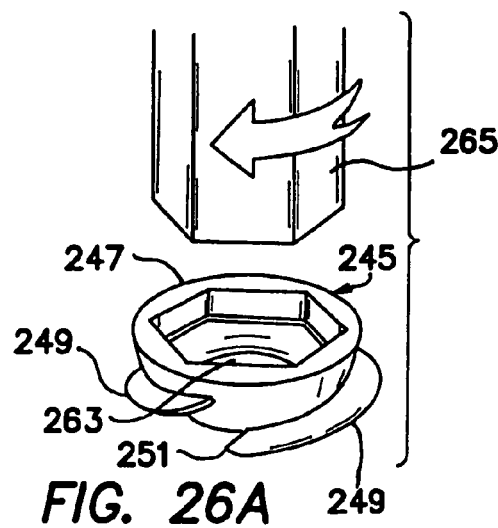

FIG. 26*a* depicts an eyelet 245 for use within a window of an arm implement. A body 247 of the eyelet 245 can comprise an aperture 263 or other torque-application structure, which, in turn, can accommodate a rotational device 265. In the illustrated embodiment, the aperture 263 comprises a hexagonal inner wall, and the rotational device 265 comprises a complementary hexagonal shaft. FIG. 26*b* provides a cross sectional view of the eyelet 245 of FIG. 26*a*, after the eyelet 245 has been inserted and secured within the conjunctiva 266. Following insertion of the eyelet through the conjunctiva 266, and securing (e.g., sealing and/or conjunctiva-tongue expanding) thereof within the conjunctiva 266, the rotational device 265 can be removed from its operative torque-applying position within the aperture 263 leaving the eyelet 245 in place. In other embodiments, the aperture 263 may be formed to have different shapes, such as circular, oval (e.g., to match a profile of the output tip of FIG. 22), or otherwise. Similarly, the rotational device 265 may be formed to have different shapes, complementary or not, or may be omitted altogether.

The eyelet 245 comprises one or more conjunctiva tongues 249. In the illustrated embodiment, the conjunctiva tongue 249 comprises a continuous spiral shape with a penetrating (e.g., piercing and cutting) leading edge 251. The leading edge and/or other parts of the conjunctiva tongue 249 (e.g., all edges) are preferably sharpened. The conjunctiva tongue 249 can be formed to have other configurations, such as, for example, tabs, as depicted in FIG. 25. In FIG. 25, an eyelet 255 is formed with four equally-spaced, rounded tabs for insertion into a gripping incision 261 formed in the conjunctiva.

During a procedure, at any given point in time, one or more of the rounded-tab conjunctiva tongues 257 can be inserted (e.g., fastened) into a gripping incision. Thus, one, two, or, preferably, all of the rounded-tab conjunctiva tongues 257 can be inserted into a gripping incision 261 prior to a lasing step of a procedure. Similarly, the conjunctiva tongue 249 of FIG. 26*a* can be inserted into a gripping incision of, or can self-tap a gripping incision and be inserted into, the conjunctiva.

Prior to, commensurate in time with, or immediately following, insertion of the eyelet 255 into the gripping incision 261, portions of the conjunctiva likely to be affected (e.g., with excess bleeding) may be treated with, for example, an electro-surgery laser having green or yellow wavelengths, a vasoconstrictor, or electro-pinchers. The eyelet 255 may comprise, for example, one or more (e.g., four) conjunctiva tongues 249 that can be folded, bent, or otherwise brought into a low-profile configuration to thereby facilitate insertion of the eyelet 255 through a gripping incision 261. Furthermore, the conjunctiva tongues 249 may in typical implementations be brought to, or returned to, by way of, for example, unfolding or unbending, a higher-profile configuration after the eyelet 255 has been inserted within, or otherwise secured to, the conjunctiva.

In one embodiment, the eyelet 255 can comprise a generally circular shape as shown in FIG. 25, and can be formed of a stretchable or bendable material which enables the eyelet 255 to be pinched or otherwise deformed into a lower-profile (e.g., oval) shape, while not collapsing, for facilitation of an insertion (e.g., and/or tucking) of the conjunctiva tongues 257 into the gripping incision 261. Pinching of the eyelet 255 may be accomplished by, for example, positioning the eyelet 255 over the gripping incision 261 such that a plane of the eyelet 255 is generally parallel to a surface of the conjunctiva at the gripping incision (i.e., in the orientation depicted in the figure), and then contacting two opposing points 277 and 279 of the body 247, and/or of the conjunctiva tongue(s) 257, of the eyelet 255. A distance between the forceps can then be reduced to generate a reduction in the distance between the two opposing points 277 and 279. Reduction of the distance between the two opposing points 277 and 279 results, in turn, in deformation of the eyelet 255 and, more particularly, results in a corresponding change in the profile of the eyelet 255 so that the insertion profile of the eyelet 255 more closely corresponds to a profile of the gripping incision 261.

The ensuing insertion of the eyelet 255 into the gripping incision 261 may thus be performed in a manner less disruptive to the conjunctival tissue or in a manner requiring a smaller gripping incision 261. Following such insertion of the eyelet 255 into the gripping incision 261, the eyelet pinching or deformation force can be removed from the eyelet 255 (e.g., from the two opposing points 277 and 279), thereby enabling the eyelet 255 to return to its former (e.g., circular) shape, whereby an added level of fixation is thus provided to the eyelet 255 within the gripping incision 261 as the conjunctiva tongue(s) 257, which in some embodiments may comprise fewer or more continuous or discontinuous tongues encircling the eyelet 255, expand beneath the surface of the conjunctiva.

With the aperture 263 of the eyelet 245 free from the presence of any rotational device 265 (e.g., to the extent used) following removal thereof, and with the conjunctiva tongue 249 securing the eyelet 245 to the conjunctiva 266, the aperture 263 of eyelet 245 can accommodate a fiber optic tip 268 of a laser handpiece 271 as depicted in FIG. 26b. Similarly, with reference to FIG. 25, after the eyelet 255 has been secured to the conjunctiva, the aperture 272 of the eyelet 255 can accommodate a fiber optic tip 273 of a laser handpiece 275. In certain implementations, the aperture 263 or the aperture 272 can be formed to accommodate one or more of the output tips depicted in FIGS. 21, 22 and 23, wherein such output tips may be formed of different components, proportions, or dimensions, and may be formed with or without barbs 163, but wherein, according to certain embodiments, the outer shape of a given output tip (e.g., or fiber optic tip) complementarily matches an internal profile of the corresponding aperture (e.g., 263 or 272).

In accordance with an aspect of the present invention, the open aperture 263 or 272 can serve as a portal for ablating procedures on the underlying sclera, and can also serve as a portal for visualizing (e.g., by way of a fiber optic camera) or other monitoring of the procedure or site (e.g., tissue treatment site) beneath the conjunctiva. Upon an initial insertion of, for example, a fiber optic tip within the aperture 263 or 272, the aperture may or may not extend in an unobstructed fashion (e.g., not obstructed by parts defining the gripping incision) through the conjunctiva. To the extent it does not, laser or mechanical energy or forces may be applied to open the aperture to a degree which is suitable for the application at hand. The aperture 263 or 272 can also serve as a portal for interfacing with the windows or templates of arm implements during ablating procedures on the underlying sclera, so that relatively accurate and consistent tissue treatments can be generated. Furthermore, the aperture 263 or 272, when accommodating a fiber optic tip or output tip therein, in addition to providing a portal for tissue-treatment formation and viewing of the tissue-treatment formation (e.g., by way of a fiber optic camera as disclosed herein), can also serve as a portal for providing blood aspiration (e.g., by way of an aspiration source coupled to the fiber optic tip or output tip, such as one of the tips disclosed in FIG. 21, 22 or 23), all within a minimally sized incision (e.g., gripping incision) in the conjunctiva.

By way of placement and operation of the output tip or, preferably, the fiber optic tip, of a laser handpiece within the aperture 263 or 272 of the eyelet 245 or 255, while the eyelet is secured to the conjunctiva, movement forces can be applied to the eyelet 245 or 255. These movement forces can be provided by way of, for example, pressure being applied to internal walls of the aperture 263 or 272 by the fiber optic tip. Movement of the fiber optic tip can thus result in varying magnitudes and directions of forces (e.g., pressure) being applied to the eyelet 245 or 255, resulting in movement forces that can move the eyelet 245 or 255. A user thus can tailor the movement forces to direct the eyelet 245 or 255 over one or more predetermined patterns, such as an H-shaped pattern or the pattern shown in phantom in FIG. 24b, within a window or template of an arm implement. Since the eyelet 245 or 255 is attached to the conjunctiva, movements of the eyelet 245 or 255 will result in commensurate movements of the gripping incision formed within the conjunctiva. Consequently, one or a plurality of relatively large tissue treatments can be formed beneath a minimally-sized gripping incision in the conjunctiva (e.g., as the conjunctiva adjacent to the gripping incision is stretched and compressed) within a given template or window of an arm implement. A fiber optic tip thus can be placed within the aperture of an eyelet secured to a conjunctiva (e.g., centered within an arm-implement window), and the fiber optic tip can then be traced over a pattern (e.g., moved along guide edges of the window) to form one or more tissue treatments, bringing the eyelet and conjunctiva along with it through the pattern tracing.

Regarding movements of the conjunctiva, the conjunctiva tongues 249 and 257 can be disposed on the corresponding eyelets 245 and 255, respectively, for gripping and moving at least a local portion (e.g., a portion within an arm-implement widow within which the eyelet is secured) of the conjunctiva according to typical embodiments. In use, a location (e.g., a gripping incision 261 location) can be identified for placement of the eyelet. The location can be, for example, in a neutral or central location of the arm-implement window so that pulling and distorting of the conjunctiva (e.g., in an H-shaped pattern) results in relatively uniform distortion of the conjunctiva in the different relevant directions). The identified location can correspond to a subsequently-placed gripping incision, formed either before or commensurate in time with insertion of the eyelet into the conjunctiva.

Various shapes and sizes of gripping incisions can be formed in the conjunctiva to accommodate various forms of conjunctiva tongues. For example, a size and shape of the gripping incision can be predetermined or varied according to, for example, a size and shape of the conjunctiva tongue or tongues. For instance, in an embodiment as shown in FIG. 25, wherein a the eyelet may have a diameter of, for example, about 3 mm, a pair of the conjunctiva tongues 257 may be formed to have a similar or, preferably, a slightly larger maximum dimension, such as about 3.5 mm. In this example, the gripping incision may be pre-formed in the conjunctiva to have a complementary or accommodating shape (e.g., a straight, linear incision) with a maximum dimension (e.g., length) of about 7 mm, or in other embodiments, may be formed in a straight-line shape of about 4 mm (e.g., for insertion of just two of the tabs or parts of the tongue(s) corresponding to about half of less of the eyelet circumference), or in another embodiment, formed in a semicircle shape (cf. incision of FIG. 31a) with a length measured in a straight-line from beginning to end of the incision of about 3.5 mm (e.g., for insertion of just two of the tabs or parts of the tongue(s) corresponding to about half of less of the eyelet circumference).

In another embodiment, the eyelet may have a diameter of, for example, about 1.25 mm, a pair of the conjunctiva tongues may be formed to have a similar or, preferably, a slightly larger maximum dimension, such as about 1.5 mm, and the gripping incision may be pre-formed in the conjunctiva to have a complementary or accommodating shape (e.g., a straight, linear incision) with a maximum dimension (e.g., length) of about 2.5 mm, or in other embodiments, may be formed in a straight-line shape of about 2.0 mm (e.g., for insertion of just two of the tabs or parts of the tongue(s) corresponding to about half of less of the eyelet circumference), or in another embodiment, formed in a semicircle shape with a length measured in a straight-line from beginning to end of the incision of about 1.75 mm (e.g., for insertion of just two of the tabs or parts of the tongue(s) corresponding to about half of less of the eyelet circumference).

Figure 27A:
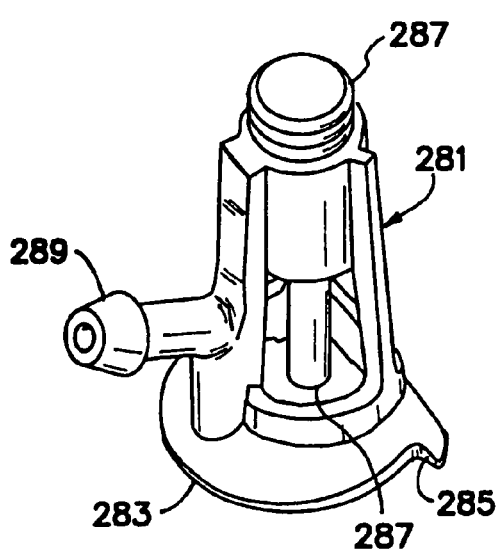
Figure 27B:
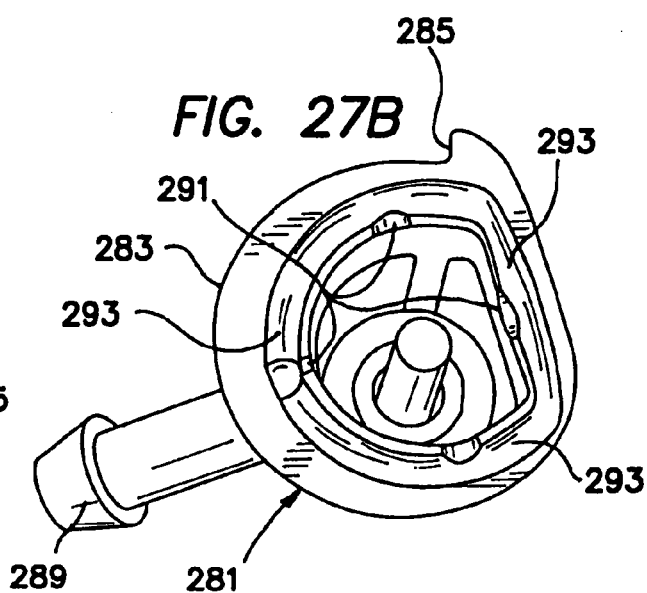

FIGS. 27a and 27b show another embodiment of an eyelet 281 with a three-post design, comprising a conjunctiva tongue 283 having a sharp leading edge 285. An optical fiber tip 287 can be inserted through a center portion of the eyelet 281, and the eyelet 281 can further comprise a vacuum tube fitting 289. The perspective underside view of the eyelet shown in FIG. 27b depicts openings 291 that are in fluid communication with the vacuum tube fitting 289. The openings 291 can be formed to generate a flush-surface opening, coupled with a fluid passage path 293, on an undersurface of the eyelet 281. In certain implementations, the structure 283 may function, in whole or in part, as an eye-surface suction cup to be mounted to the eye via an application of vacuum pressure from the openings 291 alone or in combination with the structure 283 being inserted into a gripping incision within the conjunctiva. In accordance with modified implementations, the eyelet 281 can be provided with an enlarged size and/or operated without arm-implement windows or templates.

Figure 28A:
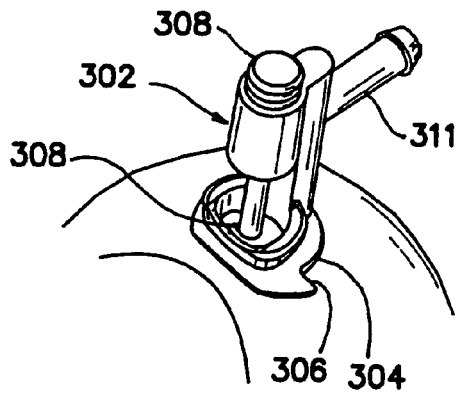
Figure 28B:
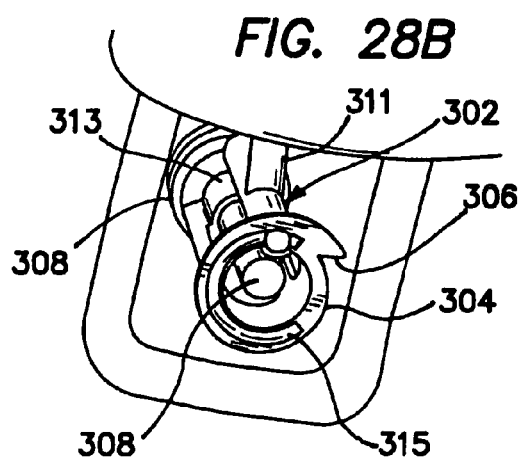

FIGS. 28a and 28b show a single-post embodiment of an eyelet 302, comprising a conjunctiva tongue (or, alternatively/additionally, eye-surface suction cup structure) 304 which may comprise a sharpened leading edge 306. An optical fiber tip 308 can be inserted through a center portion of the eyelet 302, and the eyelet 302 can further comprise a vacuum tube fitting 311. The perspective underside view of the eyelet 302 shown in FIG. 28b depicts an opening 313 that is in fluid communication with the vacuum tube fitting 311. The opening 313 can be coupled with a fluid passage path 315 on an undersurface of the eyelet 302.

Figure 29A:
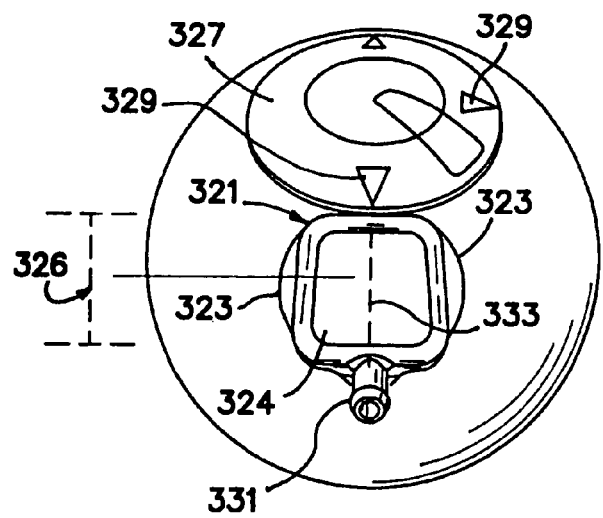
FIGS. 29A and 29B are schematic illustrations corresponding to types of structures and corresponding processes that can be implemented to treat an eye according to eighth aspects of the present invention.
Figure 29B:
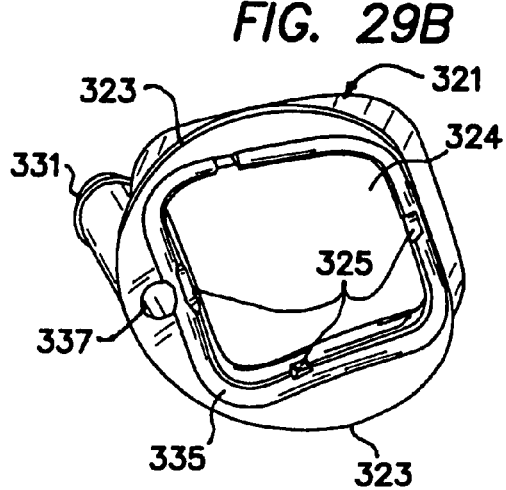

FIGS. 29a and 29b show an embodiment of an incision spreader 321 having a single-post design and, in one implementation, comprising at least one conjunctiva tongue 323. The incision spreader 321 can serve as a convenient laser guide paddle or arm implement. In an illustrated embodiment, two conjunctiva tongues 323 may be provided on opposing sides of the incision spreader 321. The incision spreader 321 thus may comprise, as shown, two conjunctiva tongues 323, with each of the conjunctiva tongues 323 having a relatively sharp leading edge for fitting into, for example, a gripping incision formed within the conjunctiva. The incision spreader 321 can further comprise a vacuum tube fitting 331 for supplying negative pressure via a single-post aspiration tube to openings 325. In preferred implementations, the structure containing the elements 323 may function, in whole or in part, as an eye-surface suction cup or mechanism to be mounted to the surface of the eye via an application of vacuum pressure from the openings 325 disposed on an underside of the incision spreader 321.

Following securing of the incision spreader 321, by way of, for example, conjunctiva tongues 323 and/or suction provided by way of the vacuum tube fitting 331 to the openings 325, an optical fiber tip and/or eyelet (not shown) can be used to perform operations within the template or window 324 of the incision spreader 321. In accordance with certain embodiments, the incision spreader 321 can be provided with an enlarged size and, preferably, is operated without any other arm-implement windows or templates besides that 324 provided by its own structure. In the illustrated example, a cornea contacting cup 327 can be provided with indicia 329 disposed thereon for providing incision locations or reference axes 333. Incisions, such as, for example, gripping incisions as discussed herein, or, in other implementations, I-beam incisions 326 such as illustrated in the figure, may be disposed in the conjunctiva at a location or locations corresponding to the indicia 329.

Figure 30:
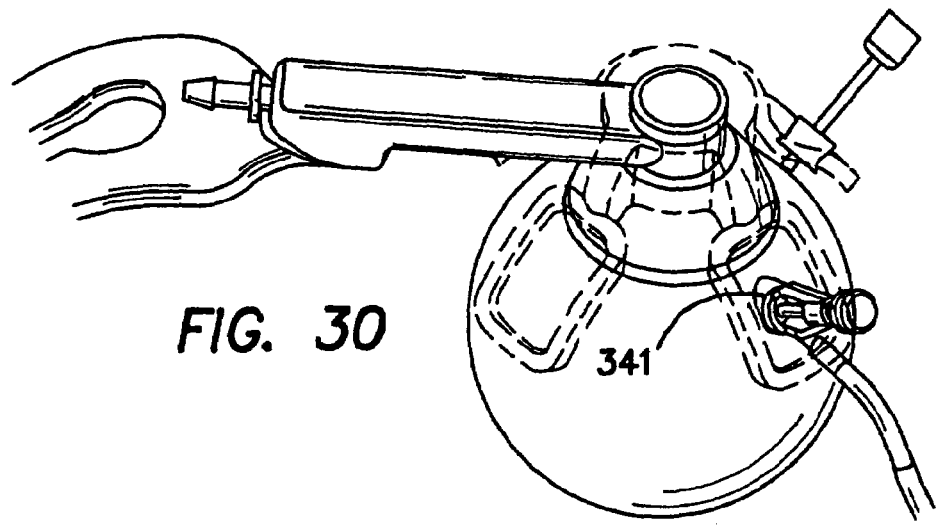
FIGS. 30-31B are schematic illustrations corresponding to types of structures and corresponding processes that can be implemented to treat an eye according to ninth aspects of the present invention.
Figure 31A:
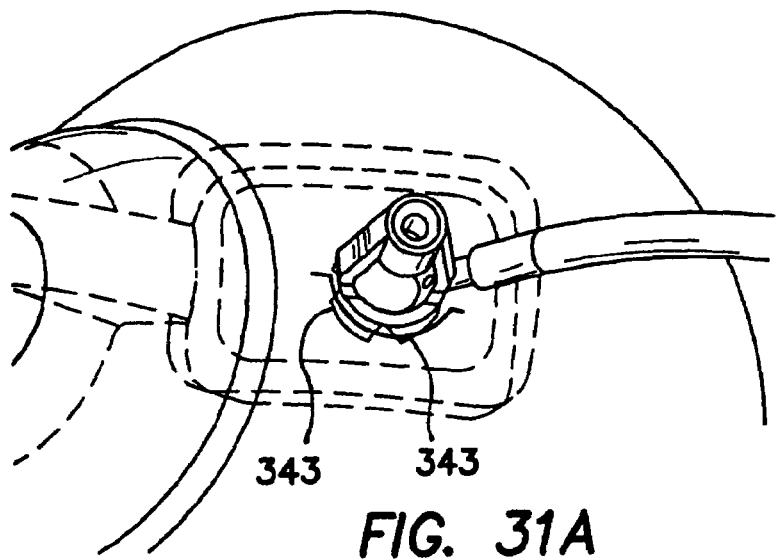
Figure 31B:
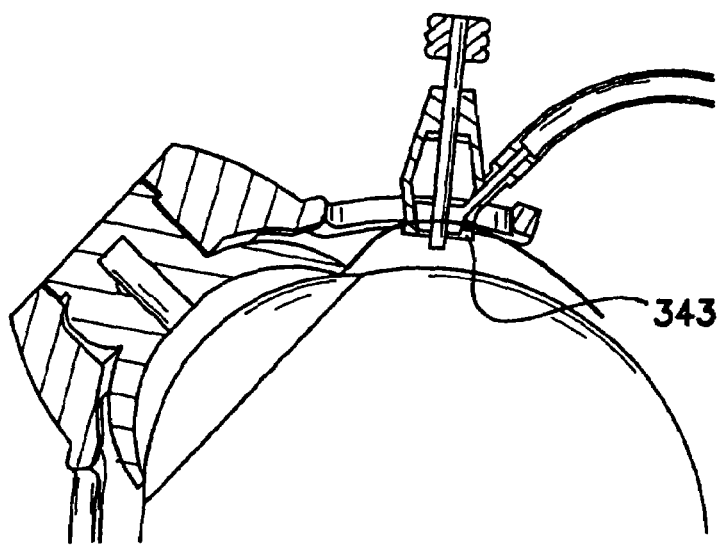

FIG. 30 shows a modified embodiment of the three-post design depicted in FIGS. 27a and 27b, wherein a single conjunctiva tongue 341 can be provided, and FIGS. 31a and 31b illustrate an embodiment of the three post-design having four conjunctiva tongues 343 resembling those of FIG. 25. Spaces between the conjunctiva tongues 343 can serve as vents, which may, for example, prevent the eyelet from adhering to the sclera under relatively high (e.g., momentarily high) vacuum forces which may be generated during a procedure.

FIGS. 32a and 32b show an embodiment of a wound spreader 341, which may comprise structures similar to and which may operate similarly to the incision spreader 321. For example, the wound spreader 341 may comprise a single-post design, a pair of opposing conjunctiva tongues (and/or eye-surface suction cup structure) 343, and a template or window 345 within which, for example, an optical fiber tip and/or eyelet (not shown) can be used to perform operations allowing the wound spreader 341 to operate as a laser guide paddle or arm implement. The wound spreader 341 can be formed (e.g., molded) of a material (e.g., porex) that wicks liquids (e.g., blood) in the directions of the arrows A1 and A2 up into a stem or handle portion 348 of the wound spreader 341 to thereby facilitate a relatively blood-free work site for impartation of tissue treatments. Thus, the wound spreader 341 may be constructed without a vacuum tube fitting.

An incision spreader 351 as depicted in FIGS. 33a and 33b can comprise or correspond to any one or more of the elements provided in the embodiments of FIGS. 29a, 29b, 32a or 32b, with a primary element of this construction being an open-front 353 design of the template or window 355. The open-front 353 can provide additional working space and visibility.

According to modified embodiments, groupings of tissue treatments of the present invention may be disposed around cuts (e.g., kerfs) to the sclera implemented in accordance with other technologies. In other modified embodiments, as an alternative or addition to any of the embodiments described herein, tissue treatments may be arranged to approximate or resemble prior-art surgical-formation shapes. For instance, tissue treatments may be applied to resemble, or in combination with, correctional patterns as described in U.S. Pat. No. 6,263,879, the contents of which are expressly incorporated herein by reference. In implementations wherein tissue treatments of the present invention are applied in combination with one or more of the patterns or ablation patterns disclosed in the aforementioned patent, the tissue treatments can be disposed for example along part or all of the boundary(ies) of the linear ablation pattern(s) with or without the ablation pattern(s) being formed as well. In modified embodiments, any of the above tissue treatments may be applied in combination with any other eye treatments to the extent compatible, or modifiable to be compatible, by one skilled in the art, with the present tissue treatments. For instance, the presently-described alterations (e.g., rotations and/or shifts) to the conjunctiva in connection with the formation of tissue treatments in the sclera may be modified and/or combined with other technologies (e.g., such as described in the aforementioned patent) involving applications or formations of treatments (e.g., ablations) to the sclera.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, it is intended that the present invention not be limited by the disclosed embodiments, but be defined by reference to the appended additional disclosure in claims format.

What is claimed is:

1. A method for treating an eye in need of one or more of a physiological and a vision correction, comprising directing treatment energy through a conjunctiva and onto a sclera, an intersection of the treatment energy and the conjunctiva having a first shape and a first area, and an intersection of the treatment energy and the sclera having a first reference shape and a first reference area, wherein the directing is characterized by one or more of the following non-equivalent and non-interchangeable features: (a) a maximum dimension of the first shape is greater than a maximum dimension of the first reference shape, (b) the first area is greater than the first reference area, and (c) a maximum concentration or intensity of treatment energy in the first area is less than a maximum concentration or intensity of treatment energy in the first reference area.

2. The method as set forth in claim 1, wherein a characteristic or measurable parameter of the treatment energy tapers within the sclera from about 1 to about 100 percent with each 1 percent drop in depth within the sclera.

3. The method as set forth in claim 2, wherein the characteristic or measurable parameter is a dimension of the treatment energy.

4. The method as set forth in claim 3, wherein the dimension is a diameter of the treatment energy.

5. The method as set forth in claim 4, wherein a profile of the treatment energy has one or more of a conical and a "V" shape.

6. The method as set forth in claim 1, wherein a characteristic or measurable parameter of the treatment energy drops by about 1 to about 20 percent for each 1 percent drop in depth within the sclera.

7. The method as set forth in claim 6, wherein the characteristic or measurable parameter is a dimension of the treatment energy.

8. The method as set forth in claim 7, wherein the dimension is a diameter of the treatment energy.

9. The method as set forth in claim 8, wherein a profile of the treatment energy has one or more of a conical and a "V" shape.

10. The method as set forth in claim 1, wherein a maximum dimension of the first shape is greater than a maximum dimension of the first reference shape.

11. The method as set forth in claim 1, wherein the first area is greater than the first reference area.

12. The method as set forth in claim 1, wherein a maximum concentration or intensity of treatment energy in the first area is less than a maximum concentration or intensity of treatment energy in the first reference area.

13. The method as set forth in claim 1, wherein the treatment energy has a focal point, which is on or in the sclera.

14. The method as set forth in claim 1, wherein the treatment energy is focused on or into the sclera more so than on the conjunctiva.

15. The method as set forth in claim 1, wherein the treatment energy is focused on or into the sclera to an extent, which is greater than an extent to which the treatment energy is focused on or into the conjunctiva.

16. The method as set forth in claim 1, wherein treatment energy is focused on or inside the sclera rather than on the conjunctiva.

17. The method as set forth in claim 1, wherein portions of the conjunctiva penetrated by the treatment energy are not substantially affected by the treatment energy.

18. The method as set forth in claim 1, wherein portions of the conjunctiva penetrated by the treatment energy are not substantially ablated by the treatment energy.

19. The method as set forth in claim 1, wherein portions of the conjunctiva penetrated by the treatment energy are affected to a lesser extent than the extent to which the sclera is affected by the treatment energy.

20. The method as set forth in claim 1, wherein the treatment energy is directed non-invasively through the conjunctiva.

21. The method as set forth in claim 1, wherein the treatment energy comprises a beam of electromagnetic energy.

22. The method as set forth in claim 1, wherein the treatment energy is a beam of electromagnetic energy.

23. The method as set forth in claim 1, wherein the treatment energy is a beam of laser light.

24. The method as set forth in claim 1, wherein the treatment energy is directed through the conjunctiva in a manner so that the intersection of the treatment energy and the conjunctiva has the shape of a spot.

25. The method as set forth in claim 1, wherein the treatment energy forms a pattern in the sclera that is smaller than a pattern formed in the conjunctiva by the treatment energy.

26. The method as set forth in claim 1, wherein the sclera, but not the conjunctiva, is ablated.

27. The method as set forth in claim 26, wherein a portion of the conjunctiva is rotated or shifted, relative to the sclera, from a first configuration to a second configuration, before the sclera is ablated.

28. The method as set forth in claim 27, wherein the ablating of the sclera is followed by rotating or shifting at least part of the portion in a direction back to the first configuration.

29. The method as set forth in claim 1, wherein:
the treatment energy comprises a beam of treatment energy;
the beam is directed through the conjunctiva in a manner so that the intersection of the beam and the conjunctiva has the shape of a spot; and
the beam forms one or more of a plurality of adjacent radial lines and a plurality of substantially parallel lines.

30. The method as set forth in claim 1, wherein the treatment energy comprises a first beam of treatment energy and the method further comprises directing a second beam of treatment energy through the conjunctiva and onto a sclera, wherein an intersection of the second beam and the conjunctiva has a second shape and a second area, an intersection of the second beam and the sclera having a second reference shape and a second reference area, and wherein the directing is characterized by one or more of the following non-equivalent and non-interchangeable features: (a) a maximum dimension of the second shape is greater than a maximum dimension of the second reference shape, (b) the second area is greater than the second reference area, and (c) a maximum concentration or intensity of treatment energy in the second area is less than a maximum concentration or intensity of treatment energy in the second reference area.

31. The method as set forth in claim 30, wherein the method further comprises directing a third beam of treatment energy through the conjunctiva and onto a sclera, wherein an intersection of the third beam and the conjunctiva has a third shape and a third area, an intersection of the third beam and the sclera having a third reference shape and a third reference area, and wherein the directing is characterized by one or more of the following non-equivalent and non-interchangeable features: (a) a maximum dimension of the third shape is greater than a maximum dimension of the third reference shape, (b) the third area is greater than the third reference area, and (c) a maximum concentration or intensity of treatment energy in the third area is less than a maximum concentration or intensity of treatment energy in the third reference area.

32. The method as set forth in claim 31, wherein:
the directing of each of the second beam and the third beam comprises rotating or shifting a portion of the conjunctiva, relative to the sclera, from a first configuration to a second configuration; and
the directing of each of the second beam and the third beam is followed by rotating or shifting at least part of the portion in a direction back to the first configuration.

33. The method as set forth in claim 32, wherein:
the second and third beams are directed through the conjunctiva in manners so that the intersection of each and the conjunctiva has the shape of a spot;
the beam forms one or more of a plurality of adjacent radial lines and a plurality of substantially parallel lines; and
each of the second beam and the third beam forms one or more of a plurality of adjacent radial lines and a plurality of substantially parallel lines.

34. The method as set forth in claim 1, wherein the treatment energy is directed invasively on or into the sclera.

* * * * *